US012054724B2

(12) United States Patent
Maguire et al.

(10) Patent No.: US 12,054,724 B2
(45) Date of Patent: Aug. 6, 2024

(54) AAV VECTORS ENCODING CLARIN-1 OR GJB2 AND USES THEREOF

(71) Applicants: President and Fellows of Harvard College, Cambridge, MA (US); The General Hospital Corporation, Boston, MA (US)

(72) Inventors: Casey A. Maguire, Arlington, MA (US); David P. Corey, Cambridge, MA (US); Bence Gyorgy, Cambridge, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 946 days.

(21) Appl. No.: 17/046,487

(22) PCT Filed: Apr. 10, 2019

(86) PCT No.: PCT/US2019/026852
§ 371 (c)(1),
(2) Date: Oct. 9, 2020

(87) PCT Pub. No.: WO2019/200016
PCT Pub. Date: Oct. 17, 2019

(65) Prior Publication Data
US 2021/0079406 A1 Mar. 18, 2021

Related U.S. Application Data

(60) Provisional application No. 62/655,745, filed on Apr. 10, 2018.

(51) Int. Cl.
C12N 15/70 (2006.01)
A61K 9/00 (2006.01)
A61K 48/00 (2006.01)
C07K 14/05 (2006.01)
C07K 14/705 (2006.01)
C12N 7/00 (2006.01)
A61K 38/00 (2006.01)

(52) U.S. Cl.
CPC .......... *C12N 15/70* (2013.01); *A61K 9/0019* (2013.01); *A61K 9/0046* (2013.01); *A61K 48/0008* (2013.01); *C07K 14/705* (2013.01); *C12N 7/00* (2013.01); *A61K 38/00* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | |
|---|---|---|
| 5,399,363 A | 3/1995 | Liversidge et al. |
| 5,478,745 A | 12/1995 | Samulski et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,641,515 A | 6/1997 | Ramtoola |
| 5,738,868 A | 4/1998 | Shinkarenko |
| 5,741,516 A | 4/1998 | Webb et al. |
| 5,795,587 A | 8/1998 | Gao et al. |
| 6,001,650 A | 12/1999 | Colosi |
| 6,156,303 A | 12/2000 | Russell et al. |
| 7,198,951 B2 | 4/2007 | Gao et al. |
| 9,102,949 B2 | 8/2015 | Gao et al. |
| 9,585,971 B2 | 3/2017 | Deverman et al. |
| 9,920,317 B2 * | 3/2018 | Lee ............... C12N 15/113 |
| 11,149,256 B2 | 10/2021 | Gradinaru et al. |
| 2003/0138772 A1 | 7/2003 | Gao et al. |
| 2003/0194721 A1 | 10/2003 | Mikita et al. |
| 2004/0214272 A1 | 10/2004 | La Rosa et al. |
| 2007/0020624 A1 | 1/2007 | Rubenfield et al. |
| 2008/0311627 A1 | 12/2008 | Tetzner et al. |
| 2009/0270480 A1 | 10/2009 | Amegadzie et al. |
| 2012/0164205 A1 | 6/2012 | Baum et al. |
| 2014/0336245 A1 | 11/2014 | Mingozzi et al. |
| 2017/0021038 A1 | 1/2017 | Pan et al. |
| 2017/0166926 A1 | 6/2017 | Deverman et al. |
| 2017/0183647 A1 | 6/2017 | Chavez et al. |
| 2017/0240885 A1 | 8/2017 | Deverman et al. |

(Continued)

FOREIGN PATENT DOCUMENTS

| | | |
|---|---|---|
| CN | 101883859 A | 11/2010 |
| CN | 109207520 A | 1/2019 |

(Continued)

OTHER PUBLICATIONS

Dinculescu et al. (PLOS, Feb. 16, 2016, p. 1-15).*
International Search Report and Written Opinion for Application No. PCT/US2019/026852, mailed Jul. 10, 2019.
International Preliminary Report on Patentability for Application No. PCT/US2019/026852, mailed Oct. 22, 2020.
Abelson et al., Methods in Enzymology. 2004. Academic Press, Eds.
Boshart et al., A very strong enhancer is located upstream of an immediate early gene of human cytomegalovirus. Cell. Jun. 1985;41(2):521-30. doi: 10.1016/s0092-8674(85)80025-8.
Chan et al., Engineered AAVs for efficient noninvasive gene delivery to the central and peripheral nervous systems. Nat Neurosci. Aug. 2017; 20(8): 1172-1179. doi:10.1038/nn.4593.

(Continued)

*Primary Examiner* — Agnieszka Boesen
(74) *Attorney, Agent, or Firm* — Wolf, Greenfield & Sacks, P.C.

(57) ABSTRACT

Aspects of the disclosure relate to compositions and methods useful for treating hereditary hearing loss, for example, Usher syndrome type 3A or nonsyndromic hearing loss and deafness (DFNB1). In some embodiments, the disclosure provides isolated nucleic acids, vectors, and rAAV.9.PHP.B comprising a transgene encoding a Clarin-1 or a GJB2, and methods of treating hearing loss using the same.

19 Claims, 18 Drawing Sheets

Specification includes a Sequence Listing.

(56) References Cited

U.S. PATENT DOCUMENTS

| | | |
|---|---|---|
| 2018/0187213 A1 | 7/2018 | High et al. |
| 2018/0282382 A1 | 10/2018 | Alagramam |
| 2022/0119475 A1 | 4/2022 | Corey et al. |
| 2022/0195458 A1 | 6/2022 | Maguire et al. |
| 2023/0340038 A1 | 10/2023 | Corey et al. |

FOREIGN PATENT DOCUMENTS

| | | |
|---|---|---|
| JP | 2008-263851 A | 11/2008 |
| WO | WO 1998/00041 A1 | 1/1998 |
| WO | WO 1998/010088 A1 | 3/1998 |
| WO | WO 2003/097685 A1 | 11/2003 |
| WO | WO 2006/119432 A2 | 11/2006 |
| WO | WO 2015/038958 A1 | 3/2015 |
| WO | WO 2015/130840 A2 | 9/2015 |
| WO | WO 2017/100791 A1 | 6/2017 |
| WO | WO 2017/136536 A1 | 8/2017 |
| WO | WO 2018/022608 A2 | 2/2018 |
| WO | WO 2019/028306 A2 | 2/2019 |
| WO | WO 2019/046069 A1 | 3/2019 |
| WO | WO 2019/200016 A1 | 10/2019 |
| WO | WO 2020/014471 A1 | 1/2020 |
| WO | WO 2020/077295 A1 | 4/2020 |
| WO | WO 2020/097372 A1 | 5/2020 |
| WO | WO 2020/198737 A1 | 10/2020 |
| WO | WO 2021/067448 A1 | 4/2021 |
| WO | WO 2022/232327 A2 | 11/2022 |

OTHER PUBLICATIONS

Chow et al., Inducible Cre Recombinase Activity in Mouse Cerebellar Granule Cell Precursors and Inner Ear Hair Cells. Dev Dyn. Nov. 2006;235(11):2991-8. doi: 10.1002/dvdy.20948.

Chu et al., SV40 DNA transfection of cells in suspension: analysis of efficiency of transcription and translation of T-antigen. Gene. Mar. 1981;13(2):197-202. doi: 10.1016/0378-1119(81)90008-1.

De Felipe et al., Tricistronic and tetracistronic retroviral vectors for gene transfer. Hum Gene Ther. Sep. 1, 2000;11(13):1921-31. doi: 10.1089/10430340050129530.

De Felipe et al., Use of the 2A sequence from foot-and-mouth disease virus in the generation of retroviral vectors for gene therapy. Gene Ther. Feb. 1999;6(2):198-208. doi: 10.1038/sj.gt.3300811.

Deverman et al., Cre-dependent selection yields AAV variants for widespread gene transfer to the adult brain. Nat Biotechnol. Feb. 2016;34(2):204-9.

Fields et al., Usher syndrome type III: revised genomic structure of the USH3 gene and identification of novel mutations. Am J Hum Genet. Sep. 2002;71(3):607-17. doi: 10.1086/342098. Epub Jul. 16, 2002.

Fisher et al., Transduction with recombinant adeno-associated virus for gene therapy is limited by leading-strand synthesis. J Virol. Jan. 1996;70(1):520-32. doi: 10.1128/JVI.70.1.520-532.1996.

Furler et al., Recombinant AAV vectors containing the foot and mouth disease virus 2A sequence confer efficient bicistronic gene expression in cultured cells and rat substantia nigra neurons. Gene Ther. Jun. 2001;8(11):864-73. doi: 10.1038/sj.gt.3301469.

Geng et al., Modeling and Preventing Progressive Hearing Loss in Usher Syndrome III. Sci Rep. Oct. 18, 2017;7(1):13480. doi: 10.1038/s41598-017-13620-9.

Gossen et al., Tight control of gene expression in mammalian cells by tetracycline-responsive promoters. Proc Natl Acad Sci U S A. Jun. 15, 1992;89(12):5547-51. doi: 10.1073/pnas.89.12.5547.

Gossen et al., Transcriptional activation by tetracyclines in mammalian cells. Science. Jun. 23, 1995;268(5218):1766-9. doi: 10.1126/science.7792603.

Graham et al., A new technique for the assay of infectivity of human adenovirus 5 DNA. Virology. Apr. 1973;52(2):456-67. doi: 10.1016/0042-6822(73)90341-3.

György et al., An AAV9 capsid variant efficiently transduces inner ear hair cells in mice and non-human primates and rescues hearing in a mouse model of human deafness. Mol Ther Methods Clin Dev. Nov. 20, 2018;13:1-13. doi: 10.1016/j.omtm.2018.11.003. eCollection Jun. 14, 2019.

György et al., Rescue of Hearing by Gene Delivery to Inner-Ear Hair Cells Using Exosome-Associated AAV. Mol Ther. Feb. 1, 2017;25(2):379-391.

Halpin et al., Self-processing 2A-polyproteins—a system for co-ordinate expression of multiple proteins in transgenic plants. Plant J. Feb. 1999;17(4):453-9. doi: 10.1046/j.1365-313x.1999.00394.x.

Harvey et al., Inducible control of gene expression: prospects for gene therapy. Curr Opin Chem Biol. Aug. 1998;2(4):512-8. doi: 10.1016/s1367-5931(98)80128-2.

Hordeaux et al., The Neurotropic Properties of AAV-PHP.B Are Limited to C57BL/6J Mice. Mol Ther. Mar. 7, 2018;26(3):664-668. doi: 10.1016/j.ymthe.2018.01.018. Epub Feb. 2, 2018.

Klump et al., Retroviral vector-mediated expression of HoxB4 in hematopoietic cells using a novel coexpression strategy. Gene Ther. May 2001;8(10):811-7. doi: 10.1038/sj.gt.3301447.

Landegger et al., A synthetic AAV vector enables safe and efficient gene transfer to the mammalian inner ear. Nat Biotechnol. Mar. 2017;35(3):280-284.

Magari et al., Pharmacologic control of a humanized gene therapy system implanted into nude mice. J Clin Invest. Dec. 1, 1997;100(11):2865-72. doi: 10.1172/JCI119835.

Maguire et al., AAV9-PHP.B for cochlear hair cell gene delivery. Harvard Medical School. 28 Pages.

Matsuzaki et al., Intravenous administration of the adeno-associated virus-PHP.B capsid fails to upregulate transduction efficiency in the marmoset brain. Neurosci Lett. Feb. 5, 2018;665:182-188. doi: 10.1016/j.neulet.2017.11.049. Epub Nov. 24, 2017.

Mattion et al., Foot-and-mouth disease virus 2A protease mediates cleavage in attenuated Sabin 3 poliovirus vectors engineered for delivery of foreign antigens. J Virol. Nov. 1996;70(11):8124-7. doi: 10.1128/JVI.70.11.8124-8127.1996.

McCarthy, Self-complementary AAV vectors; advances and applications. Mol Ther. Oct. 2008;16(10):1648-56. doi: 10.1038/mt.2008.171. Epub Aug. 5, 2008.

Ross, Comments on the article "Persistent confusion of total entropy and chemical system entropy in chemical thermodynamics" [(1996) Proc. Natl. Acad. Sci. USA 93, 7452-7453]. Proc Natl Acad Sci U S A. Dec. 10, 1996;93(25):14314; discussion 14315.

Ryan et al., Foot-and-mouth disease virus 2A oligopeptide mediated cleavage of an artificial polyprotein. Embo J. Feb. 15, 1994;13(4):928-33.

Sacheli et al., Gene transfer in inner ear cells: a challenging race. Gene Ther. Mar. 2013;20(3):237-47. doi: 10.1038/gt.2012.51. Epub Jun. 28, 2012.

Shu et al., Identification of Adeno-Associated Viral Vectors That Target Neonatal and Adult Mammalian Inner Ear Cell Subtypes. Hum Gene Ther. Sep. 2016;27(9):687-99. doi: 10.1089/hum.2016.053. Epub Jun. 24, 2016.

Wang et al., Ligand-inducible and liver-specific target gene expression in transgenic mice. Nat Biotechnol. Mar. 1997;15(3):239-43. doi: 10.1038/nbt0397-239.

Wang et al., Positive and negative regulation of gene expression in eukaryotic cells with an inducible transcriptional regulator. Gene Ther. May 1997;4(5):432-41. doi: 10.1038/sj.gt.3300402.

Wright et al., Identification of factors that contribute to recombinant AAV2 particle aggregation and methods to prevent its occurrence during vector purification and formulation. Mol Ther. Jul. 2005;12(1):171-8. doi: 10.1016/j.ymthe.2005.02.021.

Zallocchi et al., Localization and expression of clarin-1, the Clrn1 gene product, in auditory hair cells and photoreceptors. Hear Res. Sep. 2009;255(1-2):109-20. doi: 10.1016/j.heares.2009.06.006. Epub Jun. 16, 2009.

Zhang et al., Cochlear Gene Therapy for Sensorineural Hearing Loss: Current Status and Major Remaining Hurdles for Translational Success. Front Mol Neurosci. Jun. 26, 2018;11:221. doi: 10.3389/fnmol.2018.00221. eCollection 2018.

Extended European Search Report for Application No. EP 19785415.1, mailed Dec. 15, 2021.

International Search Report and Written Opinion for Application No. PCT/US2021/050205, mailed Dec. 20, 2021.

(56) References Cited

OTHER PUBLICATIONS

International Preliminary Report on Patentability for Application No. PCT/US2021/050205, mailed Mar. 23, 2023.
Partial European Search Report for Application No. EP 20779113.8, mailed Nov. 23, 2022.
Extended European Search Report for Application No. EP 20779113.8, mailed Apr. 18, 2023.
Invitation to Pay Additional Fees for Application No. PCT/US2022/026608, mailed Aug. 15, 2022.
International Search Report and Written Opinion for Application No. PCT/US2022/026608, mailed Oct. 12, 2022.
International Preliminary Report on Patentability for Application No. PCT/US2022/026608, mailed Nov. 9, 2023.
International Search Report and Written Opinion for Application No. PCT/US2020/025720, mailed Jul. 27, 2020.
International Preliminary Report on Patentability for Application No. PCT/US2020/025720, mailed Oct. 7, 2021.
Chinese Office Action for Application No. 202080038934.8, mailed Aug. 26, 2023.
Russian Office Action for Application No. 2021131423, mailed Aug. 8, 2023.
Singapore Office Action for Application No. 11202110165X, mailed Aug. 16, 2023.
Ahmad et al., Mutations of the protocadherin gene PCDH15 cause Usher syndrome type 1F. Am J Hum Genet. Jul. 2001;69(1):25-34. doi: 10.1086/321277. Epub Jun. 7, 2001.
Ahmad et al., PCDH15 is expressed in the neurosensory epithelium of the eye and ear and mutant alleles are responsible for both USH1F and DFNB23. Hum Mol Genet. Dec. 15, 2003;12(24):3215-23. doi: 10.1093/hmg/ddg358. Epub Oct. 21, 2003.
Ahmad et al., Restoration of connexin26 protein level in the cochlea completely rescues hearing in a mouse model of human connexin30-linked deafness. Proc Natl Acad Sci U S A. Jan. 23, 2007;104(4):1337-41. doi: 10.1073/pnas.0606855104. Epub Jan. 16, 2007.
Akil et al., Dual AAV-mediated gene therapy restores hearing in a DFNB9 mouse model. Proc Natl Acad Sci U S A. Mar. 5, 2019;116(10):4496-4501. doi: 10.1073/pnas.1817537116. Epub Feb. 19, 2019.
Akil et al., Restoration of hearing in the VGLUT3 knockout mouse using virally mediated gene therapy. Neuron. Jul. 26, 2012;75(2):283-93. doi: 10.1016/j.neuron.2012.05.019.
Alagramam et al., Mutations in protocadherin 15 and cadherin 23 affect tip links and mechanotransduction in mammalian sensory hair cells. PLOS One. Apr. 21, 2011;6(4):e19183. doi: 10.1371/journal.pone.0019183.
Al-Moyed et al., A dual-AAV approach restores fast exocytosis and partially rescues auditory function in deaf otoferlin knock-out mice. EMBO Mol Med. Jan. 2019;11(1):e9396. doi: 10.15252/emmm.201809396.
Al-Zaidy et al., AVXS-101 (Onasemnogene Abeparvovec) for SMA1: Comparative Study with a Prospective Natural History Cohort. J Neuromuscul Dis. 2019;6(3):307-317. doi: 10.3233/JND-190403.
Angueyra et al., Leveraging Zebrafish to Study Retinal Degeneration. Front Cell Dev Biol. Sep. 19, 2018;6:110. doi: 10.3389/fcell.2018.00110. eCollection 2018.
Araya-Secchi et al., An elastic element in the protocadherin-15 tip link of the inner ear. Nat Commun. Nov. 18, 2016;7:13458. doi: 10.1038/ncomms13458.
Assad et al., An active motor model for adaptation by vertebrate hair cells. J Neurosci. Sep. 1992;12(9):3291-309. doi: 10.1523/JNEUROSCI.12-09-03291.1992.
Assad et al., Tip-link integrity and mechanical transduction in vertebrate hair cells. Neuron. Dec. 1991;7(6):985-94. doi: 10.1016/0896-6273(91)90343-x.
Aurnhammer et al., Universal real-time PCR for the detection and quantification of adeno-associated virus serotype 2-derived inverted terminal repeat sequences. Hum Gene Ther Methods. Feb. 2012;23(1):18-28. doi: 10.1089/hgtb.2011.034.
Azaiez et al., Genomic Landscape and Mutational Signatures of Deafness-Associated Genes. Am J Hum Genet. Oct. 4, 2018;103(4):484-497. doi: 10.1016/j.ajhg.2018.08.006. Epub Sep. 20, 2018.
Azaiez et al., GJB2: the spectrum of deafness-causing allele variants and their phenotype. Hum Mutat. Oct. 2004;24(4):305-11. doi: 10.1002/humu.20084.
Ben-Yosef et al., A mutation of PCDH15 among Ashkenazi Jews with the type 1 Usher syndrome. N Engl J Med. Apr. 24, 2003;348(17):1664-70. doi: 10.1056/NEJMoa021502.
Berry et al., Cellular transduction mechanisms of adeno-associated viral vectors. Curr Opin Virol. Curr Opin Virol. Dec. 2016;21:54-60. doi: 10.1016/j.coviro.2016.08.001. Epub Aug. 18, 2016.
Boulay et al., Hearing is normal without connexin30. J Neurosci. Jan. 9, 2013;33(2):430-4. doi: 10.1523/JNEUROSCI.4240-12.2013.
Brownstein et al., 2004. The R245X mutation of PCDH15 in Ashkenazi Jewish children diagnosed with nonsyndromic hearing loss foreshadows retinitis pigmentosa. Pediatr Res. 2004; 55: 995-1000.
Buenrostro et al., Transposition of native chromatin for fast and sensitive epigenomic profiling of open chromatin, DNA-binding proteins and nucleosome position. Nat Methods. Dec. 2013;10(12):1213-8. doi: 10.1038/nmeth.2688. Epub Oct. 6, 2013.
Caron et al., Potent and sustained huntingtin lowering via AAV5 encoding miRNA preserves striatal vol. and cognitive function in a humanized mouse model of Huntington disease. Nucleic Acids Res. Jan. 10, 2020;48(1):36-54. doi: 10.1093/nar/gkz976.
Cehajic-Kapetanovic et al., Initial results from a first-in-human gene therapy trial on X-linked retinitis pigmentosa caused by mutations in RPGR. Nat Med. Mar. 2020;26(3):354-359. doi: 10.1038/s41591-020-0763-1. Epub Feb. 24, 2020.
Chamberlain et al., Progress toward Gene Therapy for Duchenne Muscular Dystrophy. Mol Ther. 2017;25:1125-31.
Chang et al., Functional studies reveal new mechanisms for deafness caused by connexin mutations. Otol Neurotol. Feb. 2009;30(2):237-40. doi: 10.1097/MAO.0b013e318194f774.
Chang et al., Gap junction mediated intercellular metabolite transfer in the cochlea is compromised in connexin30 null mice. PloS one. 2008;3(12):e4088. doi: 10.1371/journal.pone.0004088. Epub Dec. 31, 2008.
Chang et al., Timed conditional null of connexin26 in mice reveals temporary requirements of connexin26 in key cochlear developmental events before the onset of hearing. Neurobiol Dis. Jan. 2015;73:418-27. doi: 10.1016/j.nbd.2014.09.005. Epub Sep. 22, 2014.
Chen et al., Characterization of a knock-in mouse model of the homozygous p.V37I variant in Gjb2. Sci Rep. Sep. 13, 2016;6:33279. doi: 10.1038/srep33279.
Chen et al., Developmental abnormalities in supporting cell phalangeal processes and cytoskeleton in the Gjb2 knockdown mouse model. Dis Model Mech. Feb. 26, 2018;11(2):dmm033019. doi: 10.1242/dmm.033019.
Chen et al., Down regulated connexin26 at different postnatal stage displayed different types of cellular degeneration and formation of organ of Corti. Biochem Biophys Res Commun. Feb. 28, 2014;445(1):71-7. doi: 10.1016/j.bbrc.2014.01.154. Epub Jan. 31, 2014.
Chen et al., Engineered AAVs for efficient noninvasive gene delivery to the central and peripheral nervous systems. Nat Neurosci. Author manuscript; available in PMC Dec. 26, 2017. Published in final edited form as: Nat Neurosci. Aug. 2017;20(8): 1172-1179. Published online Jun. 26, 2017. doi: 10.1038/nn.4593.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Cheung et al., Ca2+ changes the force sensitivity of the hair-cell transduction channel. Biophys J. Jan. 1, 2006;90(1):124-39. doi: 10.1529/biophysj.105.061226. Epub Oct. 7, 2005.
Christensen et al., TRP channels in mechanosensation : Direct or indirect activation? Nat Rev Neurosci. Jul. 2007;8(7):510-21. doi: 10.1038/nrn2149.

(56) References Cited

OTHER PUBLICATIONS

Christine et al., Magnetic resonance imaging-guided phase 1 trial of putaminal AADC gene therapy for Parkinson's disease. Ann Neurol. May 2019;85(5):704-714. doi: 10.1002/ana.25450. Epub Mar. 26, 2019.

Cohen-Salmon et al., Targeted ablation of connexin26 in the inner ear epithelial gap junction network causes hearing impairment and cell death. Curr Biol. Jul. 9, 2002;12(13):1106-11. doi: 10.1016/s0960-9822(02)00904-1.

Corey et al., Kinetics of the receptor current in bullfrog saccular hair cells. J Neurosci. May 1983;3(5):962-76. doi: 10.1523/JNEUROSCI.03-05-00962.1983.

Corey et al., TRPA1 is a candidate for the mechanosensitive transduction channel of vertebrate hair cells. Nature. Dec. 9, 2004;432(7018):723-30. doi: 10.1038/nature03066. Epub Oct. 13, 2004.

Creyghton et al., Histone H3K27ac separates active from poised enhancers and predicts developmental state. Proc Natl Acad Sci U S A. Dec. 14, 2010;107(50):21931-6. doi: 10.1073/pnas.1016071107. Epub Nov. 24, 2010.

Crispino et al., BAAV mediated GJB2 gene transfer restores gap junction coupling in cochlear organotypic cultures from deaf Cx26Sox10Cre mice. PloS one. 2011;6(8):e23279. doi: 10.1371/journal.pone.0023279. Epub Aug. 18, 2011.

Crispino et al., In vivo genetic manipulation of inner ear connexin expression by bovine adeno-associated viral vectors. Sci Rep. Aug. 4, 2017;7(1):6567. doi: 10.1038/s41598-017-06759-y.

Dai et al., Rhesus Cochlear and Vestibular Functions Are Preserved After Inner Ear Injection of Saline Volume Sufficient for Gene Therapy Delivery. J Assoc Res Otolaryngol. Aug. 2017;18(4):601-617. doi: 10.1007/s10162-017-0628-6. Epub Jun. 23, 2017.

Darcy et al., Dual adeno-associated viral Anc80 vector efficiently transduces inner ear cells in non-human primates. ARO Abstract 691. 2020; 43: 447-48.

Dashkoff et al., Tailored transgene expression to specific cell types in the central nervous system after peripheral injection with AAV9. Mol Ther Methods Clin Dev. Dec. 7, 2016;3:16081. doi: 10.1038/mtm.2016.81. eCollection 2016.

D'Costa et al., Practical utilization of recombinant AAV vector reference standards: focus on vector genomes titration by free ITR qPCR. Mol Ther Methods Clin Dev. Mar. 30, 2016;5:16019. doi: 10.1038/mtm.2016.19. eCollection 2016.

Degen et al., Connexin32 can restore hearing in connexin26 deficient mice. Eur J Cell Biol. Oct. 2011;90(10):817-24. doi: 10.1016/j.ejcb.2011.05.001. Epub Aug. 2, 2011.

Del Castillo et al., A novel deletion involving the connexin-30 gene, del(GJB6-d13s1854), found in trans with mutations in the GJB2 gene (connexin-26) in subjects with DFNB1 non-syndromic hearing impairment. J Med Genet. Jul. 2005;42(7):588-94. doi: 10.1136/jmg.2004.028324.

Del Castillo et al., DFNB1 Non-syndromic Hearing Impairment: Diversity of Mutations and Associated Phenotypes. Front Mol Neurosci. Dec. 22, 2017;10:428. doi: 10.3389/fnmol.2017.00428. eCollection 2017.

Delmaghani et al., Inner ear gene therapies take off: current promises and future challenges. J Clin Med. Jul. 21, 2020;9(7):2309. doi: 10.3390/jcm9072309.

Derby et al., Gene transfer into the mammalian inner ear using HSV-1 and vaccinia virus vectors. Hear Res. Aug. 1999;134(1-2):1-8. doi: 10.1016/s0378-5955(99)00045-3.

Dinh et al., Diverse deafness mechanisms of connexin mutations revealed by studies using in vitro approaches and mouse models. Brain Res. Jun. 24, 2009;1277:52-69. doi: 10.1016/j.brainres.2009.02.008. Epub Feb. 20, 2009.

Doane et al., Regulatory elements in molecular networks. Wiley Interdiscip Rev Syst Biol Med. May 2017;9(3):10.1002/wsbm.1374. doi: 10.1002/wsbm.1374. Epub Jan. 17, 2017.

Doucette et al., Profound, prelingual nonsyndromic deafness maps to chromosome 10q21 and is caused by a novel missense mutation in the Usher syndrome type IF gene PCDH15. Eur J Hum Genet. May 2009;17(5):554-64. doi: 10.1038/ejhg.2008.231. Epub Dec. 24, 2008.

Duan, Systemic AAV Micro-dystrophin Gene Therapy for Duchenne Muscular Dystrophy. Mol Ther. Oct. 3, 2018;26(10):2337-2356. doi: 10.1016/j.ymthe.2018.07.011. Epub Jul. 17, 2018.

Dulon et al., Clarin-1 gene transfer rescues auditory synaptopathy in model of Usher syndrome, J Clin Invest. Aug. 1, 2018;128(8):3382-3401. doi: 10.1172/JCI94351. Epub Jul. 9, 2018.

Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.

Eichler et al., Hematopoietic Stem-Cell Gene Therapy for Cerebral Adrenoleukodystrophy. N Engl J Med. Oct. 26, 2017;377(17):1630-1638. doi: 10.1056/NEJMoa1700554. Epub Oct. 4, 2017.

Ellis et al., A survey of ex vivo/in vitro transduction efficiency of mammalian primary cells and cell lines with Nine natural adeno-associated virus (AAV1-9) and one engineered adeno-associated virus serotype. Virol J. Mar. 6, 2013;10:74. doi: 10.1186/1743-422X-10-74.

Feigenspan et al., Expression of connexin36 in cone pedicles and OFF-cone bipolar cells of the mouse retina. J Neurosci. Mar. 31, 2004;24(13):3325-34. doi: 10.1523/JNEUROSCI.5598-03.2004.

Fetoni et al., Cx26 partial loss causes accelerated presbycusis by redox imbalance and dysregulation of Nfr2 pathway. Redox Biol. Oct. 2018;19:301-317. doi: 10.1016/j.redox.2018.08.002. Epub Aug. 7, 2018.

Forge et al., Gap junctions and connexin expression in the inner ear. Novartis Found Symp. 1999;219:134-50; discussion 151-6. doi: 10.1002/9780470515587.ch9.

Forge et al., Gap junctions in the inner ear: comparison of distribution patterns in different vertebrates and assessement of connexin composition in mammals. J Comp Neurol. Dec. 8, 2003;467(2):207-31. doi: 10.1002/cne.10916.

Garcia et al., Localization of myosin-Iβ near both ends of tip links in frog saccular hair cells. J Neurosci. Nov. 1, 1998;18(21):8637-47. doi: 10.1523/JNEUROSCI.18-21-08637.1998.

Gaudelli et al., Programmable base editing of A*T to G*C in genomic DNA without DNA cleavage. Nature. Nov. 23, 2017;551(7681):464-471. doi: 10.1038/nature24644. Epub Oct. 25, 2017.

Ge et al., Structure of mouse protocadherin 15 of the stereocilia tip link in complex with LHFPL5. Elife. Aug. 2, 2018;7:e38770. doi: 10.7554/eLife.38770.

Genbank Submission. NCBI; Accession No. AAM88774, version AAM88774.1. clarin-1 [Homo sapiens]. Adato et al.; Aug. 5, 2002.

Genbank Submission. NCBI; Accession No. NM_004004, version NM_004004.6. Homo sapiens gap junction protein beta 2 (GJB2), mRNA. Kausar et al.; Dec. 20, 2021.

Genbank Submission. NCBI; Accession No. NP_001182723, version NP_001182723.1. clarin-1 isoform d [Homo sapiens]. Luck et al.; Oct. 11, 2020.

Genbank Submission. NCBI; Accession No. NP_001243748, version NP_001243748.1. clarin-1 isoform e [Homo sapiens]. Luck et al.; Dec. 13, 2020.

Genbank Submission. NCBI; Accession No. NP_443721, version NP_443721.1. clarin-1 isoform c [Homo sapiens]. Luck et al.; Oct. 10, 2020.

Genbank Submission. NCBI; Accession No. NP_700433, version NP_700433.1. clarin-1 isoform 1 [Mus musculus]. Dulon et al.; Oct. 7, 2020.

Genbank Submission. NCBI; Accession No. NP_700434, version NP_700434.1. clarin-1 isoform 2 [Mus musculus]. Dulon et al.; Oct. 9, 2020.

Genbank Submission. NCBI; Accession No. NP_700435, version NP_700435.1. clarin-1 isoform 3 [Mus musculus]. Dulon et al.; Oct. 10, 2020.

Genbank Submission. NCBI; Accession No. NP_777367, version NP_777367.1. clarin-1 isoform a [Homo sapiens]. Luck et al.; Dec. 14, 2020.

(56) References Cited

OTHER PUBLICATIONS

Gong et al., Adenoassociated virus serotype 9-mediated gene therapy for X-linked adrenoleukodystrophy. Mol Ther. May 2015;23(5):824-834. doi: 10.1038/mt.2015.6. Epub Jan. 16, 2015.

Gray et al., Directed evolution of a novel adeno-associated virus (AAV) vector that crosses the seizure-compromised blood-brain barrier (BBB). Mol Ther. Mar. 2010; 18(3):570-8. doi: 10.1038/mt.2009.292. Epub Dec. 29, 2009.

Gray et al., Vector design and considerations for CNS applications. Gene Vector Design and Application to Treat Nervous System Disorders. Gene Therapy Center at the University of North Carolina at Chapel Hill. 2011. pp. 9-15.

Gregorevic et al., rAAV6-microdystrophin preserves muscle function and extends lifespan in severely dystrophic mice. Nat Med. Jul. 2006;12(7):787-9. doi: 10.1038/nm1439. Epub Jul. 2, 2006.

Griciuc et al., Alzheimer's disease risk gene CD33 inhibits microglial uptake of amyloid beta. Neuron. May 22, 2013;78(4):631-43. doi: 10.1016/j.neuron.2013.04.014. Epub Apr. 25, 2013.

Grimm et al., In vitro and in vivo gene therapy vector evolution via multispecies interbreeding and retargeting of adeno-associated viruses. J Virol. Jun. 2008;82(12):5887-911. doi: 10.1128/JVI.00254-08. Epub Apr. 9, 2008.

György et al., Allele-specific gene editing prevents deafness in a model of dominant progressive hearing loss. Nat Med. Jul. 2019;25(7):1123-1130. doi: 10.1038/s41591-019-0500-9. Epub Jul. 3, 2019.

György et al., Gene Transfer with AAV9-PHP.B Rescues Hearing in a Mouse Model of Usher Syndrome 3A and Transduces Hair Cells in a Non-human Primate. Mol Ther Methods Clin Dev. Nov. 20, 2018;13:1-13. doi: 10.1016/j.omtm.2018.11.003. eCollection Jun. 14, 2019.

Hanlon et al., AAV-S: A novel AAV vector selected in brain transduces the inner ear with high efficiency. ASGCT poster. Harvard Medical School. Apr. 28, 2020. 1 page.

Hanlon et al., Selection of an Efficient AAV Vector for Robust CNS Transgene Expression. Mol Ther Methods Clin Dev. Oct. 23, 2019;15:320-332. doi: 10.1016/j.omtm.2019.10.007. eCollection Dec. 13, 2019.

Hasson et al., Unconventional myosins in inner-ear sensory epithelia J Cell Biol. Jun. 16, 1997;137(6):1287-307. doi: 10.1083/jcb.137.6.1287.

Hinderer et al., Severe Toxicity in Nonhuman Primates and Piglets Following High-Dose Intravenous Administration of an Adeno-Associated Virus Vector Expressing Human SMN. Hum Gene Ther. Mar. 2018;29(3):285-298. doi: 10.1089/hum.2018.015. Epub Feb. 12, 2018.

Hirsch et al., Delivering Transgenic DNA Exceeding the Carrying Capacity of AAV Vectors. Methods Mol Biol. 2016;1382:21-39. doi: 10.1007/978-1-4939-3271-9_2.

Holt et al., A chemical-genetic strategy demonstrates myosin 1c mediates sensory adaptation in hair cells. Cell. Feb. 8, 2002;108(3):371-81. doi: 10.1016/s0092-8674(02)00629-3.

Holt et al., Functional expression of exogenous proteins in mammalian sensory hair cells infected with adenoviral vectors. J Neurophysiol. Apr. 1999;81(4):1881-8. doi: 10.1152/jn.1999.81.4.1881.

Hordeaux et al., The GPI-Linked Protein LY6A Drives AAV-PHP.B Transport across the Blood-Brain Barrier. Mol Ther. May 8, 2019;27(5):912-921. doi: 10.1016/j.ymthe.2019.02.013. Epub Feb. 20, 2019.

Hrvatin et al., Single-cell analysis of experience-dependent transcriptomic states in the mouse visual cortex. Nat Neurosci. Jan. 2018;21(1):120-129. doi: 10.1038/s41593-017-0029-5. Epub Dec. 11, 2017.

Huang et al., Role of the hepatitis B virus posttranscriptional regulatory element in export of intronless transcripts. Mol Cell Biol. 1995;15(7):3864-3869. doi: 10.1128/MCB.15.7.3864.

Hudry et al., Exosome-associated AAV vector as a robust and convenient neuroscience tool. Gene Ther. Apr. 2016;23(4):380-92. doi: 10.1038/gt.2016.11. Epub Feb. 2, 2016.

Hughes et al., AAV9 intracerebroventricular gene therapy improves lifespan, locomotor function and pathology in a mouse model of Niemann-Pick type C1 disease. Hum Mol Genet. Sep. 1, 2018;27(17):3079-3098. doi: 10.1093/hmg/ddy212.

Iizuka et al., Perinatal Gjb2 gene transfer rescues hearing in a mouse model of hereditary deafness. Hum Mol Genet. Jul. 1, 2015;24(13):3651-61. doi: 10.1093/hmg/ddv109. Epub Mar. 23, 2015.

Indzhykulian et al., Molecular remodeling of tip links underlies mechanosensory regeneration in auditory hair cells. PLoS Biol. 2013;11(6):e1001583. doi: 10.1371/journal.pbio. 1001583. Epub Jun. 11, 2013.

Iossa et al., GJB2 Gene Mutations in Syndromic Skin Diseases with Sensorineural Hearing Loss. Curr Genomics. Nov. 2011;12(7):475-785. doi: 10.2174/138920211797904098.

Isgrig et al., AAV2.7m8 is a powerful viral vector for inner ear gene therapy. Nat Commun. Jan. 25, 2019;10(1):427. doi: 10.1038/s41467-018-08243-1.

Isgrig et al., Gene Therapy Restores Balance and Auditory Functions in a Mouse Model of Usher Syndrome. Mol Ther. Mar. 1, 2017;25(3):780-791. doi: 10.1016/j.ymthe.2017.01.007. Epub Feb. 21, 2017.

Ivanchenko et al., AAV-S: A versatile capsid variant for transduction of mouse and primate inner ear. Mol Ther Methods Clin Dev. Mar. 29, 2021;21:382-398. doi: 10.1016/j.omtm.2021.03.019. eCollection Jun. 11, 2021.

Ivanchenko et al., Preclinical testing of AAV9-PHP.B for transgene expression in the non-human primate cochlea. Hear Res. Sep. 1, 2020;394:107930. doi: 10.1016/j.heares.2020.107930. Epub Feb. 26, 2020.

Johnson et al., Connexin-Mediated Signaling in Nonsensory Cells Is Crucial for the Development of Sensory Inner Hair Cells in the Mouse Cochlea. J Neurosci. Jan. 11, 2017;37(2):258-268. doi: 10.1523/JNEUROSCI.2251-16.2016.

Jovičić et al., Comprehensive Expression Analyses of Neural Cell-Type-Specific miRNAs Identify New Determinants of the Specification and Maintenance of Neuronal Phenotypes. J Neurosci. Mar. 20, 2013;33(12):5127-37. doi: 10.1523/JNEUROSCI.0600-12.2013.

Kamiya et al., Assembly of the cochlear gap junction macromolecular complex requires connexin 26. J Clin Invest. Apr. 2014;124(4):1598-607. doi: 10.1172/JCI67621. Epub Mar. 3, 2014.

Kazmierczak et al., Cadherin 23 and protocadherin 15 interact to form tip-link filaments in sensory hair cells. Nature. Sep. 6, 2007;449(7158):87-91. doi: 10.1038/nature06091.

Kelsell et al., Connexin 26 mutations in hereditary non-syndromic sensorineural deafness. Nature. May 1, 1997;387(6628):80-3. doi: 10.1038/387080a0.

Kenna et al., Audiologic phenotype and progression in GJB2 (Connexin 26) hearing loss. Arch Otolaryngol Head Neck Surg. Jan. 2010;136(1):81-7. doi: 10.1001/archoto.2009.202.

Keppeler et al., Ultrafast optogenetic stimulation of the auditory pathway by targeting- optimized Chronos. EMBO J. Dec. 14, 2018;37(24):e99649. doi: 10.15252/embj.201899649. Epub Nov. 5, 2018.

Keskin et al., AAV5-miHTT Lowers Huntingtin mRNA and Protein without Off-Target Effects in Patient-Derived Neuronal Cultures and Astrocytes. Mol Ther Methods Clin Dev. Oct. 4, 2019;15:275-284. doi: 10.1016/j.omtm.2019.09.010. eCollection Dec. 13, 2019.

Kiang et al., Upstream genomic sequence of the human connexin26 gene. Gene. Oct. 15, 1997;199(1-2):165-71. doi: 10.1016/s0378-1119(97)00365-x.

Kikuchi et al., Gap junction systems in the mammalian cochlea. Brain Res Brain Res Rev. Apr. 2000;32(1):163-6. doi: 10.1016/s0165-0173(99)00076-4.).

Kikuchi et al., Gap junctions in the rat cochlea: immunohistochemical and ultrastructural analysis. Anat Embryol (Berl). Feb. 1995;191(2):101-18. doi: 10.1007/BF00186783.

Kodippili et al., Dual AAV Gene Therapy for Duchenne Muscular Dystrophy with a 7-kb Mini-Dystrophin Gene in the Canine Model. Hum Gene Ther. Mar. 2018;29(3):299-311. doi: 10.1089/hum.2017.095. Epub Aug. 4, 2017.

(56) References Cited

OTHER PUBLICATIONS

Koehler et al., Generation of inner ear organoids containing functional hair cells from human pluripotent stem cells. Nat Biotechnol. Jun. 2017;35(6):583-589. doi: 10.1038/nbt.3840. Epub May 1, 2017.
Koerber et al., Construction of diverse adeno-associated viral libraries for directed evolution of enhanced gene delivery vehicles. Nat Protoc. 2006;1(2):701-6. doi: 10.1038/nprot.2006.93.
Kohrman et al., Gene therapy for deafness. Gene Ther. Dec. 2013;20(12):1119-23. doi: 10.1038/gt.2013.39. Epub Jul. 18, 2013.
Korbelin et al., Pulmonary Targeting of Adeno-associated Viral Vectors by Next-generation Sequencing-guided Screening of Random Capsid Displayed Peptide Libraries. Mol Ther. Jun. 2016;24(6):1050-1061. doi: 10.1038/mt.2016.62. Epub Mar. 28, 2016.
Kwan et al., TRPA1 contributes to cold, mechanical, and chemical nociception but is not essential for hair-cell transduction. Neuron. Apr. 20, 2006;50(2):277-89. doi: 10.1016/j.neuron.2006.03.042.
Lang et al., Effects of chronic furosemide treatment and age on cell division in the adult gerbil inner ear. J Assoc Res Otolaryngol. Jun. 2003;4(2):164-75. doi: 10.1007/s10162-002-2056-4.
Lee et al., Efficient viral transduction in mouse inner ear hair cells with utricle injection and AAV9-PHP.B. Hear Res. Sep. 1, 2020;394:107882. doi: 10.1016/j.heares.2020.107882. Epub Jan. 13, 2020.
Lee et al., Mice with conditional deletion of Cx26 exhibit No. vestibular phenotype despite secondary loss of Cx30 in the vestibular end organs. Hearing Res. Oct. 2015;328:102-12. doi: 10.1016/j.heares.2015.07.018. Epub Jul. 29, 2015.
Leone et al., Long-term follow-up after gene therapy for canavan disease. Sci Transl Med. Dec. 19, 2012;4(165):165ra163. doi: 10.1126/scitranslmed.3003454.
Levy et al., Cytosine and adenine base editing of the brain, liver, retina, heart and skeletal muscle of mice via adeno-associated viruses. Nat Biomed Eng. Jan. 2020;4(1):97-110. doi: 10.1038/s41551-019-0501-5. Epub Jan. 14, 2020.
Li et al., Characterization of slow-cycling cells in the mouse cochlear lateral wall. PloS one. Jun. 20, 2017;12(6):e0179293. doi: 10.1371/journal.pone.0179293. eCollection 2017.
Li et al., Engineering adeno-associated virus vectors for gene therapy. Nat Rev Genet. Apr. 2020;21(4):255-272. doi: 10.1038/s41576-019-0205-4. Epub Feb. 10, 2020.
Li et al., MicroRNAs in hair cell development and deafness. Curr Opin Otolaryngol Head Neck Surg. Oct. 2010;18(5):459-65. doi: 10.1097/MOO.0b013e32833e0601.
Li et al., Notch inhibition induces mitotically generated hair cells in mammalian cochleae via activating the Wnt pathway. Proc Natl Acad Sci U S A. Jan. 6, 2015;112(1):166-71. doi: 10.1073/pnas.1415901112. Epub Dec. 22, 2014.
Lin et al., Hearing loss and incident dementia. Arch Neurol. Feb. 2011;68(2):214-20. doi: 10.1001/archneurol.2010.362.
Lin et al., Hearing loss prevalence in the United States. Arch Intern Med. Nov. 14, 2011;171(20):1851-2. doi: 10.1001/archinternmed.2011.506.
Lopes et al., Gene Therapy for the Retinal Degeneration of Usher Syndrome Caused by Mutations in MYO7A. Cold Spring Harb Perspect Med. Jan. 20, 2015;5(6):a017319. doi: 10.1101/cshperspect.a017319.
Lukashkina et al., Amplification mode differs along the length of the mouse cochlea as revealed by connexin 26 deletion from specific gap junctions. Sci Rep. Jul. 12, 2017;7(1):5185. doi: 10.1038/s41598-017-04279-3.
Lustig et al.,, Cochlear Gene Therapy. Cold Spring Harb Perspect Med. Sep. 3, 2019;9(9):a033191. doi: 10.1101/cshperspect.a033191.
Ma et al., Connexin 26 in mature ears influences survival of hair cells and neurons. ARO Abstract 404. 2020; 43:258-9.
Maguire et al., Efficacy, Safety, and Durability of Voretigene Neparvovec-rzyl in RPE65 Mutation-Associated Inherited Retinal Dystrophy: Results of Phase 1 and 3 Trials. Ophthalmology. Sep. 2019;126(9):1273-1285. doi: 10.1016/j.ophtha.2019.06.017. Epub Jun. 22, 2019.
Maguire et al., Microvesicle-associated AAV vector as a novel gene delivery system. Mol Ther. May 2012;20(5):960-71. doi: 10.1038/mt.2011.303. Epub Feb. 7, 2012.
Mahendrasingam et al., Subcellular distribution and relative expression of fibrocyte markers in the CD/1 mouse cochlea assessed by semiquantitative immunogold electron microscopy. J Histochem Cytochem. Nov. 2011;59(11):984-1000. doi: 10.1369/0022155411421801.
Mammano, Inner Ear Connexin Channels: Roles in Development and Maintenance of Cochlear Function. Cold Spring Harb Perspect Med. Jul. 1, 2019;9(7):a033233. doi: 10.1101/cshperspect.a033233.
Manno et al., Successful transduction of liver in hemophilia by AAV-Factor IX and limitations imposed by the host immune response. Nat Med. Mar. 2006;12(3):342-7. doi: 10.1038/nm1358. Epub Feb. 12, 2006.
Mason et al., Universal infant hearing screening by automated auditory brainstem response measurement. Pediatrics. Feb. 1998;101(2):221-8. doi: 10.1542/peds.101.2.221.
Matsuzaki et al., Neurotropic Properties of AAV-PHP.B Are Shared among Diverse Inbred Strains of Mice. Mol Ther. Apr. 10, 2019;27(4):700-704. doi: 10.1016/j.ymthe.2019.02.016. Epub Feb. 28, 2019.
McLean et al., GREAT improves functional interpretation of cis-regulatory regions. Nat Biotechnol. May 2010;28(5):495-501. doi: 10.1038/nbt.1630. Epub May 2, 2010.
Mei et al., A deafness mechanism of digenic Cx26 (GJB2) and Cx30 (GJB6) mutations: Reduction of endocochlear potential by impairment of heterogeneous gap junctional function in the cochlear lateral wall. Neurobiol Dis. Dec. 2017;108:195-203. doi: 10.1016/j.nbd.2017.08.002. Epub Aug. 17, 2017.
Mendell et al., Single-Dose Gene-Replacement Therapy for Spinal Muscular Atrophy. N Engl J Med. Nov. 2, 2017;377(18):1713-1722. doi: 10.1056/NEJMoa1706198.
Millington-Ward et al., Suppression and replacement gene therapy for autosomal dominant disease in a murine model of dominant retinitis pigmentosa. Mol Ther. Apr. 2011;19(4):642-9. doi: 10.1038/mt.2010.293. Epub Jan. 11, 2011.
Mookherjee et al., Long-term rescue of cone photoreceptor degeneration in retinitis pigmentosa 2 (RP2)-knockout mice by gene replacement therapy. Hum Mol Genet. Nov. 15, 2015;24(22):6446-58. doi: 10.1093/hmg/ddv354. Epub Sep. 10, 2015.
Multiple Authors Listed, ASGCT abstracts. Molecular Therapy. Apr. 28, 2020; 28(4S1): 2, 76, and 77.
Mutai et al., Mitotic activity and specification of fibrocyte subtypes in the developing rat cochlear lateral wall. Neuroscience. Nov. 10, 2009;163(4):1255-63. doi: 10.1016/j.neuroscience.2009.07.059. Epub Aug. 4, 2009.
Narui et al., Tuning Inner-Ear Tip-Link Affinity Through Alternatively Spliced Variants of Protocadherin-15. Biochemistry. Mar. 20, 2018;57(11):1702-1710. doi: 10.1021/acs.biochem.7b01075. Epub Mar. 6, 2018.
Nathwani, Gene therapy for hemophilia. Hematology Am Soc Hematol Educ Program. Dec. 6, 2019;2019(1):1-8. doi: 10.1182/hematology.2019000007.
Nickel et al., Gap junctions and connexins in the inner ear: their roles in homeostasis and deafness. Curr Opin Otolaryngol Head Neck Surg. Oct. 2008;16(5):452-7. doi: 10.1097/MOO.0b013e32830e20b0.
Nist-Lund et al., Improved TMC1 gene therapy restores hearing and balance in mice with genetic inner ear disorders. Nat Commun. Jan. 22, 2019;10(1):236. doi: 10.1038/s41467-018-08264-w.
Niwa et al., In vitro polyadenylation is stimulated by the presence of an upstream intron. Genes Dev. Sep. 1990;4(9):1552-9. doi: 10.1101/gad.4.9.1552.
No Author Listed, Disclosure of Inventions. Harvard Medical School. May 2020. 5 pages.
No Author Listed, GenBank Accession No. KAA0147029.1. hypothetical protein FNF29_07656 [Cafeteria roenbergensis]. Sep. 9, 2019.

(56) References Cited

OTHER PUBLICATIONS

No et al., Ecdysone-inducible gene expression in mammalian cells and transgenic mice. Proc Natl Acad Sci U S A. Apr. 16, 1996; 93(8): 3346-3351.

Nonnenmacher et al., High capsid-genome correlation facilitates creation of AAV libraries for directed evolution. Mol Ther. Apr. 2015;23(4):675-82. doi: 10.1038/mt.2015.3. Epub Jan. 14, 2015.

Olson et al., Post-translational tools expand the scope of synthetic biology. Curr Opin Chem Biol. Aug. 2012;16(3-4):300-6. doi: 10.1016/j.cbpa.2012.06.003. Epub Jul. 4, 2012.

Pan et al., Gene therapy restores auditory and vestibular function in a mouse model of Usher syndrome type 1c. Nat Biotechnol. Mar. 2017;35(3):264-272. doi: 10.1038/nbt.3801. Epub Feb. 6, 2017.

Park et al., Generation of transgenic marmosets expressing genetically encoded calcium indicators. Sci Rep. Oct. 11, 2016;6:34931. doi: 10.1038/srep34931.

Paulk et al., Bioengineered AAV Capsids with Combined High Human Liver Transduction In Vivo and Unique Humoral Seroreactivity. Mol Ther. Jan. 3, 2018;26(1):289-303. doi: 10.1016/j.ymthe.2017.09.021. Epub Sep. 25, 2017.

Paulk et al., Bioengineered Viral Platform for Intramuscular Passive Vaccine Delivery to Human Skeletal Muscle. Mol Ther Methods Clin Dev. Jul. 24, 2018;10:144-155. doi: 10.1016/j.omtm.2018.06.001. eCollection Sep. 21, 2018.

Pepermans et al., The CD2 isoform of protocadherin-15 is an essential component of the tip-link complex in mature auditory hair cells. EMBO Mol Med. Jul. 2014;6(7):984-92. doi: 10.15252/emmm.201403976.

Powers et al., A Partial Calcium-Free Linker Confers Flexibility to Inner-Ear Protocadherin-15. Structure. Mar. 7, 2017;25(3):482-495. doi: 10.1016/j.str.2017.01.014. Epub Feb. 23, 2017.

Pulicherla et al., Engineering liver-detargeted AAV9 vectors for cardiac and musculoskeletal gene transfer. Mol Ther. Jun. 2011;19(6):1070-8. doi: 10.1038/mt.2011.22. Epub Mar. 1, 2011.

Rada-Iglesias et al., A unique chromatin signature uncovers early developmental enhancers in humans. Nature. Feb. 10, 2011;470(7333):279-83. doi: 10.1038/nature09692. Epub Dec. 15, 2010.

Rees et al., Base editing: precision chemistry on the genome and transcriptome of living cells. Nat Rev Genet. Dec. 2018;19(12):770-788. doi: 10.1038/s41576-018-0059-1.

Remes et al., AAV-mediated TIMP-1 overexpression in aortic tissue reduces the severity of allograft vasculopathy in mice. J Heart Lung Transplant. Apr. 2020;39(4):389-398. doi: 10.1016/j.healun.2020.01.1338. Epub Jan. 30, 2020.

Rodriguez-Paris et al., Comparative functional characterization of novel non-syndromic GJB2 gene variant p.Gly45Arg and lethal syndromic variant p.Gly45Glu. PeerJ. Oct. 11, 2016;4:e2494. doi: 10.7717/peerj.2494. eCollection 2016.

Sallach et al., Tropism-modified AAV vectors overcome barriers to successful cutaneous therapy. Mol Ther. May 2014;22(5):929-39. doi: 10.1038/mt.2014.14. Epub Jan. 28, 2014.

Sasaki et al., Generation of transgenic non-human primates with germline transmission. Nature. May 28, 2009;459(7246):523-7. doi: 10.1038/nature08090.

Scheffer et al., Gene expression profiling identifies Hes6 as a transcriptional target of ATOH1 in cochlear hair cells. FEBS Lett. Oct. 2, 2007;581(24):4651-6. doi: 10.1016/j.febslet.2007.08.059. Epub Sep. 4, 2007.

Scheffer et al., The alpha1 subunit of nicotinic acetylcholine receptors in the inner ear: transcriptional regulation by ATOH1 and co-expression with the gamma subunit in hair cells. J Neurochem. Dec. 2007;103(6):2651-64. doi: 10.1111/j.1471-4159.2007.04980.x.

Scheffer et al., XIRP2, an actin-binding protein essential for inner ear hair-cell stereocilia. Cell Rep. Mar. 24, 2015;10(11):1811-8. doi: 10.1016/j.celrep.2015.02.042. Epub Mar. 12, 2015.

Senis et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014.

Shepherd et al., The extent of adaptation in bullfrog saccular hair cells. J Neurosci. Oct. 1994;14(10):6217-29. doi: 10.1523/JNEUROSCI.14-10-06217.1994.

Solc et al., Molecular cloning of myosins from the bullfrog saccular macula: A candidate for the adaptation motor. Auditory Neurosci. 1994; 1:63-75.

Sotomayor et al., In search of the hair-cell gating spring: Elastic properties of ankyrin and cadherin repeats. Structure. Apr. 2005;13(4):669-82. doi: 10.1016/j.str.2005.03.001.

Sotomayor et al., Structural determinants of cadherin-23 function in hearing and deafness. Neuron. Apr. 15, 2010;66(1):85-100. doi: 10.1016/j.neuron.2010.03.028.

Sotomayor et al., Structure of a force-conveying cadherin bond essential for inner-ear mechanotransduction. Nature. Dec. 6;492(7427):128-32. doi: 10.1038/nature11590. Epub Nov. 7, 2012.

Srinivas et al., Human diseases associated with connexin mutations. Biochim Biophys Acta Biomembr. Jan. 2018;1860(1):192-201. doi: 10.1016/j.bbamem.2017.04.024. Epub Apr. 27, 2017.

Sun et al., Connexin30 null and conditional connexin26 null mice display distinct pattern and time course of cellular degeneration in the cochlea. J Comp Neurol. Oct. 20, 2009;516(6):569-79. doi: 10.1002/cne.22117.

Suzuki et al., Cochlear gene therapy with ancestral AAV in adult mice: complete transduction of inner hair cells without cochlear dysfunction. Sci Rep. Apr. 3, 2017;7:45524. doi: 10.1038/srep45524.

Takada et al., Connexin 26 null mice exhibit spiral ganglion degeneration that can be blocked by BDNF gene therapy. Hearing Res. Mar. 2014;309:124-35. doi: 10.1016/j.heares.2013.11.009. Epub Dec. 12, 2013.

Tan et al., AAV-ie enables safe and efficient gene transfer to inner ear cells. Nat Commun. Aug. 19, 2019;10(1):3733. doi: 10.1038/s41467-019-11687-8.

Tao et al., Delivery of adeno-associated virus vectors in adult mammalian inner-ear cell subtypes without auditory dysfunction. Hum Gene Ther. Apr. 2018;29(4):492-506. doi: 10.1089/hum.2017.120. Epub Jan. 22, 2018.

Trapani et al., Effective delivery of large genes to the retina by dual AAV vectors. EMBO Mol Med. Feb. 2014;6(2):194-211. doi: 10.1002/emmm.201302948. Epub Dec. 15, 2013.

Trapani et al., Seeing the Light after 25 Years of Retinal Gene Therapy. Trends Mol Med. Aug. 2018;24(8):669-681. doi: 10.1016/j.molmed.2018.06.006. Epub Jul. 5, 2018.

Trapani, Dual AAV Vectors for Stargardt Disease. Methods Mol Biol. 2018; 1715:153-175. doi: 10.1007/978-1-4939-7522-8_11.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Tse et al., Structure-guided evolution of antigenically distinct adeno-associated virus variants for immune evasion. Proc Natl Acad Sci U S A. Jun. 13, 2017;114(24):E4812-E4821. doi: 10.1073/pnas.1704766114. Epub May 30, 2017.

Tu et al., Mapping and characterization of the basal promoter of the human connexin26 gene. Biochim Biophys Acta. Nov. 26, 1998;1443(1-2):169-81. doi: 10.1016/s0167-4781(98)00212-7.

Västinsalo et al., Alternative splice variants of the USH3A gene Clarin 1 (CLRN1). Eur J Hum Genet. Jan. 2011;19(1):30-5. doi: 10.1038/ejhg.2010.140. Epub Aug. 18, 2010.

Vogl et al., Tryptophan-rich basic protein (WRB) mediates insertion of the tail-anchored protein otoferlin and is required for hair cell exocytosis and hearing. EMBO J. Dec. 1, 2016;35(23):2536-2552. doi: 10.15252/embj.201593565. Epub Jul. 25, 2016.

Wan et al., Efficacy and Safety of rAAV2-ND4 Treatment for Leber's Hereditary Optic Neuropathy. Sci Rep. Feb. 19, 2016;6:21587. doi: 10.1038/srep21587.

Wan et al., Inner ear supporting cells: Rethinking the silent majority. Semin Cell Dev Biol. May 2013;24(5):448-59. doi: 10.1016/j.semcdb.2013.03.009. Epub Mar. 29, 2013.

(56) References Cited

OTHER PUBLICATIONS

Wang et al., A Rationally Engineered Capsid Variant of AAV9 for Systemic CNS-Directed and Peripheral Tissue-Detargeted Gene Delivery in Neonates. Mol Ther Methods Clin Dev. Mar. 1, 20186;9:234-246. doi: 10.1016/j.omtm.2018.03.004. eCollection Jun. 15, 2018.

Wang et al., Targeted connexin26 ablation arrests postnatal development of the organ of Corti. Biochem Biophys Res Commun. Jul. 17, 2009;385(1):33-7. doi: 10.1016/j.bbrc.2009.05.023. Epub May 9, 2009.

Wassmer et al., Exosome-associated AAV2 vector mediates robust gene delivery into the murine retina upon intravitreal injection. Sci Rep. Mar. 31, 2017;7:45329. doi: 10.1038/srep45329.

Watanabe et al., Expression of the Sox10 gene during mouse inner ear development. Brain Res Mol Brain Res. Dec. 8, 2000;84(1-2):141-5. doi: 10.1016/s0169-328x(00)00236-9.

Watters et al., Identification and dynamic regulation of tight junction protein expression in human neural stem cells. Stem Cells Dev. Jun. 15, 2015;24(12):1377-89. doi: 10.1089/scd.2014.0497.

Wilch et al., A novel DFNB1 deletion allele supports the existence of a distant cis-regulatory region that controls GJB2 and GJB6 expression. Clin Genet. Sep. 2010;78(3):267-74. doi: 10.1111/j.1399-0004.2010.01387.x. Epub Mar. 1, 2010.

Wingard et al., Cellular and Deafness Mechanisms Underlying Connexin Mutation-Induced Hearing Loss—A Common Hereditary Deafness. Front Cell Neurosci. May 29, 2015;9:202. doi: 10.3389/fncel.2015.00202. eCollection 2015.

Wise et al., The effect of deafness duration on neurotrophin gene therapy for spiral ganglion neuron protection. Hearing Res. Aug. 2011;278(1-2):69-76. doi: 10.1016/j.heares.2011.04.010. Epub May 1, 2011.

Wu et al., Hair-cell mechanotransduction persists in TRP channel knockout mice. PloS One. May 19, 2016;11(5):e0155577. doi: 10.1371/journal.pone.0155577. eCollection 2016.

Xia et al., Expression of connexin 26 and Na,K-ATPase in the developing mouse cochlear lateral wall: functional implications. Brain Res. Oct. 30, 1999;846(1):106-11. doi: 10.1016/s0006-8993(99)01996-4.

Xu et al., A combination of mutations enhances the neurotropism of AAV-2. Virology. Oct. 25, 2005;341(2):203-14. doi: 10.1016/j.virol.2005.06.051. Epub Aug. 15, 2005.

Yang et al., Gfi1-Cre knock-in mouse line: A tool for inner ear hair cell-specific gene deletion. Genesis. Jun. 2010;48(6):400-6. doi: 10.1002/dvg.20632.

Yang et al., Long-term outcomes of gene therapy for the treatment of Leber's hereditary optic neuropathy. EBioMedicine. Aug. 2016;10:258-68. doi: 10.1016/j.ebiom.2016.07.002. Epub Jul. 6, 2016.

Yeh et al., 2020. In vivo base editing rescues hearing in a mouse model of recessive deafness. ARO Abstract 172. 2020;43:96-7.

Yeh et al., In vivo base editing of post-mitotic sensory cells. Nature Commun. Jun. 5, 2018;9(1):2184. doi: 10.1038/s41467-018-04580-3.

Yu et al., Nrl knockdown by AAV-delivered CRISPR/Cas9 prevents retinal degeneration in mice. Nat Commun. Mar. 14, 2017;8:14716. doi: 10.1038/ncomms14716.

Yu et al., Supplementary Figure 2 to: Virally expressed connexin26 restores gap junction function in the cochlea of conditional Gjb2 knockout mice. Gene Ther. Nov. 2013. 1 page.

Yu et al., Virally expressed connexin26 restores gap junction function in the cochlea of conditional Gjb2 knockout mice. Gene Ther. Jan. 2014;21(1):71-80. doi: 10.1038/gt.2013.59. Epub Nov. 14, 2013.

Zelante et al., Connexin26 mutations associated with the most common form of non-syndromic neurosensory autosomal recessive deafness (DFNB1) in Mediterraneans. Hum Mol Genet. Sep. 1997;6(9):1605-9. doi: 10.1093/hmg/6.9.1605.

Zhu et al., Active cochlear amplification is dependent on supporting cell gap junctions. Nature Commun. 2013;4:1786. doi: 10.1038/ncomms2806.

* cited by examiner

Red: OHCs, Green: IHC

SEQUENCE LISTING

```
<160> NUMBER OF SEQ ID NOS: 11

<210> SEQ ID NO 1
<211> LENGTH: 232
<212> TYPE: PRT
<213> ORGANISM: Homo sapiens

<400> SEQUENCE: 1

Met Pro Ser Gln Gln Lys Lys Ile Ile Phe Cys Met Ala Gly Val Leu
1               5                   10                  15

Ser Phe Leu Cys Ala Leu Gly Val Val Thr Ala Val Gly Thr Pro Leu
            20                  25                  30

Trp Val Lys Ala Thr Ile Leu Cys Lys Thr Gly Ala Leu Leu Val Asn
        35                  40                  45

Ala Ser Gly Lys Glu Leu Asp Lys Phe Met Gly Glu Met Gln Tyr Gly
    50                  55                  60

Leu Phe His Gly Glu Gly Val Arg Gln Cys Gly Leu Gly Ala Arg Pro
65                  70                  75                  80

Phe Arg Phe Ser Phe Phe Pro Asp Leu Val Gln Ala Ile Pro Val Ser
                85                  90                  95

Ile His Ile Asn Ile Ile Leu Phe Ser Met Ile Leu Val Val Leu Thr
            100                 105                 110

Met Val Gly Thr Ala Phe Phe Met Tyr Asn Ala Phe Gly Lys Pro Phe
        115                 120                 125

Glu Thr Leu His Gly Pro Leu Gly Leu Tyr Leu Val Ser Phe Ile Ser
    130                 135                 140

Gly Ser Cys Gly Cys Leu Val Met Ile Leu Phe Ala Ser Glu Val Lys
145                 150                 155                 160

Val His Arg Leu Ser Glu Lys Ile Ala Asn Phe Lys Glu Gly Thr Tyr
                165                 170                 175

Ala Tyr Arg Thr Gln Asn Glu Asn Tyr Thr Thr Ser Phe Trp Val Val
            180                 185                 190

Phe Ile Cys Phe Phe Val His Phe Leu Asn Gly Leu Leu Ile Arg Leu
        195                 200                 205

Ala Gly Phe Gln Phe Pro Phe Thr Lys Ser Lys Glu Thr Glu Thr Thr
    210                 215                 220

Asn Val Ala Ser Asp Leu Met Tyr
225                 230

<210> SEQ ID NO 2
<211> LENGTH: 699
<212> TYPE: DNA
<213> ORGANISM: Homo sapiens

<400> SEQUENCE: 2
```

```
atgccaagcc agcagaagaa gatcatcttt tgcatggctg gcgtactgag ctttctctgt    60
gctcttggag tggtgacagc agtgggcacc ccactgtggg ttaaagccac tatcctctgc   120
aaaacagggg ctctgcttgt caacgcgtca gggaaggagc tggacaagtt catgggcgag   180
atgcagtatg gccttttcca cggagaaggc gtaaggcaat gtgggttagg agcaaggcct   240
ttccggttct cattcttccc agatttggtc aagccatcc ccgtaagcat ccacatcaat   300
attattctct tctccatgat tcttgtcgtc ttaaccatgg tggggacagc cttcttcatg   360
tacaatgctt ttggcaagcc ctttgaaact cttcatggac cactggggct ctatctggtc   420
agcttcattt caggctcctg tggctgtctt gtcatgatat tgtttgcctc tgaagtgaaa   480
gtccaccgcc tttcagagaa aattgcaaat tttaagaag ggacctatgc ctacagaaca   540
caaaacgaaa actataccac ctcattctgg gttgttttca tttgcttttt tgttcatttt   600
ttgaatgggc tcctgatacg acttgctgga tttcagttcc ctttcacaaa atctaaagaa   660
acagagacca ctaatgtagc ttcagattta atgtactga                          699
```

```
<210> SEQ ID NO 3
<211> LENGTH: 225
<212> TYPE: PRT
<213> ORGANISM: Homo sapiens

<400> SEQUENCE: 3

Met Asp Trp Gly Thr Leu Gln Thr Ile Leu Gly Gly Val Asn Lys His
1               5                   10                  15

Ser Thr Ser Ile Gly Lys Ile Trp Leu Thr Val Leu Phe Ile Phe Arg
            20                  25                  30

Ile Met Ile Leu Val Val Ala Ala Lys Glu Val Trp Gly Asp Glu Gln
        35                  40                  45

Ala Asp Phe Val Cys Asn Thr Leu Gln Pro Gly Cys Lys Asn Val Cys
    50                  55                  60

Tyr Asp His Tyr Phe Pro Ile Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Arg Arg His Glu Lys Arg Lys Phe Ile Lys Gly Glu Ile Lys Ser
            100                 105                 110

Glu Phe Lys Asp Ile Glu Glu Ile Lys Thr Gln Lys Val Arg Ile Glu
        115                 120                 125

Gly Ser Leu Trp Trp Thr Tyr Thr Ser Ser Ile Phe Phe Arg Val Ile
    130                 135                 140

Phe Glu Ala Ala Phe Met Tyr Val Phe Tyr Val Met Tyr Asp Gly Phe
145                 150                 155                 160

Ser Met Gln Arg Leu Val Lys Cys Asn Ala Trp Pro Cys Pro Asn Thr
                165                 170                 175

Val Asp Cys Phe Val Ser Arg Pro Thr Glu Lys Thr Val Phe Thr Val
            180                 185                 190

Phe Met Ile Ala Val Ser Gly Ile Cys Ile Leu Leu Asn Val Thr Glu
        195                 200                 205

Leu Cys Tyr Leu Leu Ile Arg Tyr Cys Ser Gly Lys Ser Lys Lys Pro
    210                 215                 220

Val
225
```

<210> SEQ ID NO 4
<211> LENGTH: 678
<212> TYPE: DNA
<213> ORGANISM: Homo sapiens

<400> SEQUENCE: 4

```
atggattggg gcacgctgca gacgatcctg gggggtgtga acaaacactc caccagcatt      60
ggaaagatct ggctcaccgt cctcttcatt tttcgcatta tgatcctcgt tgtggctgca     120
aaggaggtgt ggggagatga gcaggccgac tttgtctgca cacccctgca gccaggctgc     180
aagaacgtgt gctacgatca ctacttcccc atctcccaca tccggctatg ggccctgcag     240
ctgatcttcg tgtccacgcc agcgctccta gtggccatgc acgtggccta ccggagacat     300
gagaagaaga ggaagttcat caaggggag ataaagagtg aatttaagga catcgaggag      360
atcaaaaccc agaaggtccg catcgaaggc tccctgtggt ggacctacac aagcagcatc     420
ttcttccggg tcatcttcga agccgccttc atgtacgtct ctatgtcat gtacgacggc      480
ttctccatgc agcggctggt gaagtgcaac gcctggcctt gtcccaacac tgtggactgc     540
tttgtgtccc ggcccacgga aagactgtc ttcacagtgt tcatgattgc agtgtctgga      600
atttgcatcc tgctgaatgt cactgaattg tgttatttgc taattagata ttgttctggg     660
aagtcaaaaa agccagtt                                                   678
```

<210> SEQ ID NO 5
<211> LENGTH: 226
<212> TYPE: PRT
<213> ORGANISM: Mus musculus

<400> SEQUENCE: 5

Met Asp Trp Gly Thr Leu Gln Ser Ile Leu Gly Gly Val Asn Lys His
1               5                   10                  15

Ser Thr Ser Ile Gly Lys Ile Trp Leu Thr Val Leu Phe Ile Phe Arg
            20                  25                  30

Ile Met Ile Leu Val Val Ala Ala Lys Glu Val Trp Gly Asp Glu Gln
        35                  40                  45

Ala Asp Phe Val Cys Asn Thr Leu Gln Pro Gly Cys Lys Asn Val Cys
    50                  55                  60

Tyr Asp His His Phe Pro Ile Ser His Ile Arg Leu Trp Ala Leu Gln
65                  70                  75                  80

Leu Ile Met Val Ser Thr Pro Ala Leu Leu Val Ala Met His Val Ala
                85                  90                  95

Tyr Arg Arg His Glu Lys Lys Arg Lys Phe Met Lys Gly Glu Ile Lys
            100                 105                 110

Asn Glu Phe Lys Asp Ile Glu Glu Ile Lys Thr Gln Lys Val Arg Ile
        115                 120                 125

Glu Gly Ser Leu Trp Trp Thr Tyr Thr Thr Ser Ile Phe Phe Arg Val
    130                 135                 140

Ile Phe Glu Ala Val Phe Met Tyr Val Phe Tyr Ile Met Tyr Asn Gly
145                 150                 155                 160

Phe Phe Met Gln Arg Leu Val Lys Cys Asn Ala Trp Pro Cys Pro Asn
                165                 170                 175

Thr Val Asp Cys Phe Ile Ser Arg Pro Thr Glu Lys Thr Val Phe Thr
            180                 185                 190

Val Phe Met Ile Ser Val Ser Gly Ile Cys Ile Leu Leu Asn Ile Thr
        195                 200                 205

Glu Leu Cys Tyr Leu Phe Val Arg Tyr Cys Ser Gly Lys Ser Lys Arg

Pro Val
225

<210> SEQ ID NO 6
<211> LENGTH: 684
<212> TYPE: DNA
<213> ORGANISM: Mus musculus

<400> SEQUENCE: 6

```
gacaagatgg attggggcac actccagagc atcctcgggg gtgtcaacaa acactccacc      60
agcattggaa agatctggct cacggtcctc ttcatcttcc gcatcatgat cctcgtggtg     120
gctgcaaagg aggtgtgggg agatgagcaa gccgattttg tctgcaacac gctccagcct     180
ggctgcaaga atgtatgcta cgaccaccac ttccccatct ctcacatccg gctctgggct     240
ctgcagctga tcatggtgtc cacgccagcc ctcctggtag ctatgcatgt ggcctaccgg     300
agacatgaaa agaaacggaa gttcatgaag ggagagataa agaacgagtt taaggacatc     360
gaagagatca aacccagaa ggtccgtatc gaagggtccc tgtggtggac ctacaccacc     420
agcatcttct tccgggtcat ctttgaagcc gtcttcatgt acgtcttta catcatgtac     480
aatggcttct tcatgcaacg tctggtgaaa tgcaacgctt ggccctgccc caatacagtg     540
gactgcttca tttccaggcc cacagaaaag actgtcttca ccgtgtttat gatttctgtg     600
tctggaattt gcattctgct aaatatcaca gagctgtgct atttgttcgt taggtattgc     660
tcaggaaagt ccaaaagacc agtc                                            684
```

<210> SEQ ID NO 7
<211> LENGTH: 743
<212> TYPE: PRT
<213> ORGANISM: Artificial Sequence
<220> FEATURE:
<223> OTHER INFORMATION: Synthetic Polypeptide

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Leu Ala Val
            580                 585                 590
```

```
Pro Phe Lys Ala Gln Ala Gln Thr Gly Trp Val Gln Asn Gln Gly Ile
            595                 600                 605

Leu Pro Gly Met Val Trp Gln Asp Arg Asp Val Tyr Leu Gln Gly Pro
        610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
            645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
            675                 680                 685

Glu Ile Glu Trp Glu Leu Gln Lys Glu Asn Ser Lys Arg Trp Asn Pro
        690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740

<210> SEQ ID NO 8
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 8

Thr Leu Ala Val Pro Phe Lys
1               5

<210> SEQ ID NO 9
<211> LENGTH: 2232
<212> TYPE: DNA
<213> ORGANISM: Artificial Sequence
<220> FEATURE:
<223> OTHER INFORMATION: Synthetic Polynucleotide

<400> SEQUENCE: 9
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaatacttg acccggcaa cggactcgac      180 aaggggagc cggtcaacgc agcagacgcg gcggccctcg agcacgacaa ggcctacgac     240
cagcagctca aggccggaga caacccgtac ctcaagtaca ccacgccga cgccgagttc     300 caggagcggc tcaaagaaga tacgtctttt gggggcaacc tcgggcgagc agtcttccag     360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
tcagtcccag accctcaacc aatcggagaa cctcccgcag cccctcagg tgtgggatct     600 cttacaatgg cttcaggtgg tggcgcacca gtggcagaca taacgaagg tgccgatgga     660 gtgggtagtt cctcgggaaa ttggcattgc gattccaat ggctggggga cagagtcatc     720
accaccagca cccgaacctg ggccctgccc acctacaaca atcacctcta caagcaaatc     780
```

-continued

| | |
|---|---|
| tccaacagca catctggagg atcttcaaat gacaacgcct acttcggcta cagcaccccc | 840 |
| tgggggtatt ttgacttcaa cagattccac tgccacttct caccacgtga ctggcagcga | 900 |
| ctcatcaaca caactgggga ttccggcct aagcgactca acttcaagct cttcaacatt | 960 |
| caggtcaaag aggttacgga caacaatgga gtcaagacca tcgccaataa ccttaccagc | 1020 |
| acggtccagg tcttcacgga ctcagactat cagctcccgt acgtgctcgg gtcggctcac | 1080 |
| gagggctgcc tcccgccgtt cccagcggac gttttcatga ttcctcagta cgggtatctg | 1140 |
| acgcttaatg atggaagcca ggccgtgggt cgttcgtcct tttactgcct ggaatatttc | 1200 |
| ccgtcgcaaa tgctaagaac gggtaacaac ttccagttca gctacgagtt tgagaacgta | 1260 |
| cctttccata gcagctacgc tcacagccaa agcctggacc gactaatgaa tccactcatc | 1320 |
| gaccaatact tgtactatct ctcaagaact attaacggtt ctggacagaa tcaacaaacg | 1380 |
| ctaaaattca gtgtggccgg acccagcaac atggctgtcc agggaagaaa ctacataacct | 1440 |
| ggacccagct accgcaaaca acgtgtctca accactgtga ctcaaaacaa caacagcgaa | 1500 |
| tttgcttggc ctggagcttc ttcttgggct ctcaatggac gtaatagctt gatgaatcct | 1560 |
| ggacctgcta tggccagcca caaagaagga gaggaccgtt tctttccttt gtctggatct | 1620 |
| ttaatttttg gcaaacaagg aactggaaga gacaacgtgg atgcgacaa agtcatgata | 1680 |
| accaacgaag aagaaattaa aactactaac ccggtagcaa cggagtccta tggacaagtg | 1740 |
| gccacaaacc accagagtgc ccaaactttg gcggtgcctt taaggcaca ggcgcagacc | 1800 |
| ggctgggttc aaaaccaagg aatacttccg ggtatggttt ggcaggacag agatgtgtac | 1860 |
| ctgcaaggac ccatttgggc caaaattcct cacacggacg gcaactttca cccttctccg | 1920 |
| ctgatgggag ggtttggaat gaagcaccccg cctcctcaga tcctcatcaa aaacacacct | 1980 |
| gtacctgcgg atcctccaac ggccttcaac aaggacaagc tgaactcttt catcacccag | 2040 |
| tattctactg gccaagtcag cgtggagatc gagtgggagc tgcagaagga aaacagcaag | 2100 |
| cgctggaacc cggagatcca gtacacttcc aactattaca agtctaataa tgttgaattt | 2160 |
| gctgttaata ctgaaggtgt atatagtgaa ccccgcccca ttggcaccag ataccctgact | 2220 |
| cgtaatctgt aa | 2232 |

<210> SEQ ID NO 10
<211> LENGTH: 249
<212> TYPE: PRT
<213> ORGANISM: Mus musculus

<400> SEQUENCE: 10

Met Tyr Pro Tyr Asp Val Pro Asp Tyr Ala Gly Gly Gly Ser Gly Gly
1               5                   10                  15

Gly Ser Pro Ser Gln Gln Lys Lys Ile Ile Phe Cys Met Ala Gly Val
            20                  25                  30

Leu Ser Phe Leu Cys Ala Leu Gly Val Val Thr Ala Val Gly Thr Pro
        35                  40                  45

Leu Trp Val Lys Ala Thr Ile Leu Cys Lys Thr Gly Ala Leu Leu Val
    50                  55                  60

Asn Ala Ser Gly Lys Glu Leu Asp Lys Phe Met Gly Glu Met Gln Tyr
65                  70                  75                  80

Gly Leu Phe His Gly Glu Gly Val Arg Gln Cys Gly Leu Gly Ala Arg
                85                  90                  95

Pro Phe Arg Phe Ser Phe Pro Asp Leu Val Gln Ala Ile Pro Val
            100                 105                 110

```
Ser Ile His Ile Asn Ile Ile Leu Phe Ser Met Ile Leu Val Val Leu
        115                 120                 125

Thr Met Val Gly Thr Ala Phe Phe Met Tyr Asn Ala Phe Gly Lys Pro
    130                 135                 140

Phe Glu Thr Leu His Gly Pro Leu Gly Leu Tyr Leu Val Ser Phe Ile
145                 150                 155                 160

Ser Gly Ser Cys Gly Cys Leu Val Met Ile Leu Phe Ala Ser Glu Val
                165                 170                 175

Lys Val His Arg Leu Ser Glu Lys Ile Ala Asn Phe Lys Glu Gly Thr
            180                 185                 190

Tyr Ala Tyr Arg Thr Gln Asn Glu Asn Tyr Thr Thr Ser Phe Trp Val
        195                 200                 205

Val Phe Ile Cys Phe Phe Val His Phe Leu Asn Gly Leu Leu Ile Arg
    210                 215                 220

Leu Ala Gly Phe Gln Phe Pro Phe Thr Lys Ser Lys Glu Thr Glu Thr
225                 230                 235                 240

Thr Asn Val Ala Ser Asp Leu Met Tyr
                245

<210> SEQ ID NO 11
<211> LENGTH: 684
<212> TYPE: DNA
<213> ORGANISM: Mus musculus

<400> SEQUENCE: 11
aagaagatca tcttttgcat ggctggcgta ctgagctttc tctgtgctct tggagtggtg      60
acagcagtgg gcaccccact gtgggttaaa gccactatcc tctgcaaaac aggggctctg     120
cttgtcaacg cgtcagggaa ggagctggac aagttcatgg gcgagatgca gtatggcctt     180
ttccacggag aaggcgtaag gcaatgtggg ttaggagcaa ggcctttccg gttctcattc     240
ttcccagatt tggtccaagc catccccgta agcatccaca tcaatattat tctcttctcc     300
atgattcttg tcgtcttaac catggtgggg acagccttct tcatgtacaa tgcttttggc     360
aagccctttg aaactcttca tggaccactg gggctctatc tggtcagctt catttcaggc     420
tcctgtggct gtcttgtcat gatattgttt gcctctgaag tgaaagtcca ccgcctttca     480
gagaaaattg caaattttaa agaagggacc tatgcctaca aacacaaaa cgaaaactat     540 accacctcat tctgggttgt tttcatttgc ttttttgttc attttttgaa tgggctcctg     600
atacgacttg ctggatttca gttcccttc acaaaatcta aagaaacaga gaccactaat     660
gtagcttcag atttaatgta ctga                                            684
```

AAV VECTORS ENCODING CLARIN-1 OR GJB2 AND USES THEREOF

RELATED APPLICATIONS

This application is a national stage filing under 35 U.S.C. § 371 of International PCT Application PCT/US2019/026852, filed Apr. 10, 2019, which claims priority under 35 U.S.C. § 119(e) to U.S. Provisional Application, U.S. Ser. No. 62/655,745, filed Apr. 10, 2018, the entire contents of each of which are incorporated herein by reference.

BACKGROUND OF INVENTION

Hearing loss, congenital or acquired, affects approximately 30 million people in the United States alone. Congenital hearing loss (e.g., Usher syndrome or nonsyndromic hearing loss and deafness) has an incidence of about 1:1,000 births, in which half or more have a defined genetic cause. Although more than 70 such deafness genes have been identified, mutations in just one gene account for ~40% of all cases of non-syndromic, congenital, hereditary hearing loss—nearly 1000 births per year in the United States.

Because the cochlea is a surgically accessible and relatively immune-protected environment, gene therapy using viral vectors is an attractive approach. At present, however, there are no good vectors that transduce all cochlear cells, and there has been no work to identify enhancers that selective drive expression in subsets of cells. Significant challenges remain for clinical translation of AAV-based gene therapy for deafness. First, gene transfer to the cochlea has been performed almost exclusively in neonatal mice, with no reports in non-human primates (NHPs), so the translational potential of various AAVs for cochlear gene therapy in humans is unknown. Second, in many human hereditary deafnesses, the hair cells are thought to degenerate during development, so postnatal gene therapy interventions might have no target (Zhang et al, 2018, *Front. Mol. Neurosci.* 11, 221). Thus, many studies showing rescue of hearing in neonatal mice in models of human deafness do not necessarily apply to humans.

SUMMARY OF INVENTION

The present disclosure, at least in part, relates to the unexpected finding of an rAAV capable of delivering a transgene to all cochlear cells (e.g., inner hair cells, outer hair cells, and fibrocytes) across multiple species (e.g., mouse, rat, or non-human primates), and compositions thereof, in the treatment of hereditary hearing loss, for example, Usher syndrome type 3A or DFNB1.

Aspects of the present disclosure relate to an isolated nucleic acid including: (i) a first region comprising a first adeno-associated virus (AAV) inverted terminal repeat (ITR); and (ii) a second region comprising a transgene encoding clarin-1. In some embodiments, the clarin-1 is a splice form of clarin-1. In some embodiments, the splice form of clarin-1 is isoform 2 of Clarin-1.

In some embodiments, the clarin-1 includes an amino acid sequence at least 90% identical to the amino acid sequence of SEQ ID NO: 1. In some embodiments, the transgene encoding the clarin-1 includes a nucleic acid sequence of SEQ ID NO: 2.

In some embodiments, the transgene encoding clarin-1 further comprises a promoter. Some examples of useful promoters include a hybrid cytomegalovirus (CMV) immediate-early/chicken beta-actin promoter or chicken beta-actin promoter.

In some embodiments, the isolated nucleic acid further includes a third region, which can be a second adeno-associated virus (AAV) inverted terminal repeat (ITR). In some examples, the first region and/or the third region is an AAV2 ITR.

In other aspects, the present disclosure relates to a vector including an isolated nucleic acid described herein. In some embodiments, the vector is a plasmid.

In other aspects, the present disclosure relates to a host cell including an isolated nucleic acid or a vector described herein.

Another aspect of the disclosure provides a recombinant adeno-associated virus (rAAV) comprising: (i) a capsid protein; and (ii) an isolated nucleic acid encoding clarin-1 described herein. In some embodiments, the capsid protein is AAV9 capsid protein, or a variant thereof. In some embodiments, the AAV9 capsid variant is AAV9.PHP.B. In some embodiments, the capsid protein has an amino acid sequence 90% identical to the amino acid sequence of SEQ ID NO: 7.

In some embodiments, AAV9.PHP.B capsid includes a 7mer amino acid sequence at amino acid positions 588-595 of SEQ ID NO: 7. An exemplary amino acid sequence of the 7mer at amino acid positions 588-595 is TLAVPFK.

In some embodiments, the rAAV can be a single-stranded AAV (ssAAV) or a self-complementary AAV (scAAV).

In some embodiments, the rAAV is capable of delivering the transgene to a mammal. For example, the mammal can be a mouse, a rat, a non-human primate, or a human.

In some embodiments, the rAAV is formulated for delivery to the ear or the eye. In some examples, the rAAV is formulated for delivery to outer hair cells (OHC), inner hair cells (IHC), spiral ganglion neurons, stria vascularis, inner sulcus, spiral ligament, vestibular system, photoreceptors or a combination thereof.

In other aspects, the present disclosure provides pharmaceutical compositions, including the rAAV as described herein, and a pharmaceutically acceptable carrier.

In other aspects, the present disclosure provides a method for delivering clarin-1 into a cell, including transfecting the cell with the isolated nucleic acid or vector described herein, or transducing the cell with the rAAV as described herein. In some embodiments, the cell can be an outer hair cell, an inner hair cell fibrocytes or photoreceptors.

In other aspects, the present disclosure provides a method for expressing clarin-1 in a subject in need thereof, including administering to the subject an effective amount of the isolated nucleic acid or the rAAV as described herein, wherein the subject has or is suspected of having hereditary hearing loss and/or vision loss. In some embodiments, the subject is a mammal. In some examples, the mammal can be a mouse, a rat, or a non-human primate. In another example, the mammal can be a human. In some embodiments, the subject is a human, and the subject is diagnosed with Usher Syndrome, Type 3A. In some embodiments, the hearing loss and/or vision loss is associated with Usher syndrome, Type 3A.

In some embodiments, the hearing loss is associated with a mutation in the CLRN1 gene. In some embodiments, the mutation in the CLRN1 gene is a point mutation, a missense mutation, a nonsense mutation, a deletion, an insertion, or a combination thereof. Exemplary mutations in the human CLRN1 gene include, but are not limited to, c. 528T>G, c.149delCAGG/insTGTCCAAT, c.165delC, c.144T>G or a combination thereof. In some embodiments, the mutation in the CLRN1 gene results in sensorineural hearing loss, deafness, and/or progressive vision loss.

In some embodiments, administration results in delivery of the isolated nucleic acid or rAAV encoding clarin-1 to the ear of the subject. In some embodiments, the administration is via injection. In some embodiments, the injection can be through the round window membrane of the inner ear. In some embodiments, the injection can be intravitreal injection to the eye.

Another aspect of the present disclosure relates to an isolated nucleic acid including: (i) a first region comprising a first adeno-associated virus (AAV) inverted terminal repeat (ITR); and (ii) a second region comprising a transgene encoding GBJ2.

In some embodiments, the transgene encoding GJB2 includes an amino acid sequence at least 90% identical to the amino acid sequence of SEQ ID NO: 3 or 5. In some embodiments, the transgene encoding the GBJ2 includes a nucleic acid sequence of SEQ ID NO: 4 or 6.

In some embodiments, the transgene encoding GJB2 further comprises a promoter. In some examples, the promoter can be a hybrid cytomegalovirus (CMV) immediate-early/Chicken beta-actin promoter or Chicken beta-actin promoter.

In some embodiments, the isolated nucleic acid further includes a third region, which can be a second adeno-associated virus (AAV) inverted terminal repeat (ITR). In some examples, the the first region and/or the third region is an AAV2 ITR.

In other aspects, the present disclosure relates to a vector including the isolated nucleic acid described herein. In some embodiment, the vector is a plasmid.

In other aspects, the present disclosure relates to a host cell including the isolated nucleic acid or the vector described herein.

Another aspect of the disclosure provides a recombinant adeno-associated virus (rAAV) comprising: (i) a capsid protein; and (ii) an isolated nucleic acid described herein. In some embodiments, the capsid protein is AAV9 capsid protein or a variant thereof. In some embodiments, the AAV9 capsid variant is AAV9.PHP.B. In some embodiments, the capsid protein has an amino acid sequence 90% identical to amino acid sequence of SEQ ID NO: 7. In some embodiments, AAV9.PHP.B capsid includes a 7mer amino acid sequence at amino acid positions 588-595 of SEQ ID NO: 7. An exemplary amino acid sequence of the 7mer at amino acid positions 588-595 is TLAVPFK.

In some embodiments, the rAAV can be a single-stranded AAV (ssAAV) or a self-complementary AAV (scAAV).

In some embodiments, the rAAV is capable of delivering the transgene to a mammal. In some examples, the mammal can be a mouse, a rat, a non-human primate, or a human. In some embodiments, the rAAV is formulated for delivery to the ear. In some examples, the rAAV is formulated for delivery to the inner ear. In some examples, the the rAAV is formulated for delivery to the cochlea of the inner ear. In one example, the rAAV is formulated for delivery to a fibrocyte lining the fluid space of the cochlea.

In other aspects, the present disclosure provides a pharmaceutical composition, including the rAAV as described herein, and a pharmaceutically acceptable carrier.

In other aspects, the present disclosure provides a method for delivering GJB2 into a cell, the method includes transfecting the cell with the isolated nucleic acid or vector described herein, or transducing the cell with the rAAV as described herein. In some embodiments, the cell can be an outer hair cell or an inner hair cell.

In other aspects, the present disclosure provides a method for expressing GJB2 in a subject in need thereof, the method includes administering to the subject an effective amount of the isolated nucleic acid or the rAAV as described herein, wherein the subject has or is suspected of having hereditary hearing loss. In some embodiments, the subject is a mammal. In some examples, the mammal can be a mouse, a rat, or a non-human primate. In another example, the mammal can be a human. In some embodiments, the subject is a human and the subject is diagnosed with nonsyndromic hearing loss and deafness such as DFNB1. In some embodiments the hearing loss is associated with DFNB1.

In some embodiments, the hearing loss is associated with a mutation of the GJB2 gene. In some examples, the mutation of the GJB2 gene can be a point mutation, a missense mutation, a nonsense mutation, a deletion, an insertion or a combination thereof. Exemplary mutations in human GJB2 gene can be c.35delG, c.235delC, c.167delT or a combination thereof. In some embodiments, the mutation of GJB2 gene results in hearing impairment.

In some embodiments, administration results in delivery of the isolated nucleic acid or rAAV to the ear of the subject. In some examples, the administration is via injection. In some examples, the injection is through the round window membrane of the inner ear.

The details of one or more embodiments of the invention are set forth in the description below. Other features or advantages of the present invention will be apparent from the following drawing and detailed description of certain embodiments, and also from the appended claims.

BRIEF DESCRIPTION OF DRAWINGS

FIG. 1A shows AAV9-PHP.B mediated efficient GFP expression in inner and outer hair cells of sensory epithelium in neonatal P1 mice after round window membrane (RWM) injection. FIG. 1B shows low-magnification images of the cochlea showing the highest transduction level. WT, wild-type. FIG. 1C shows the median transduction (n=15). Animals were injected at P1 with $5 \times 10^{10}$ vector genomes (VGs), and the cochlea was explanted at P5 and cultured for another day (P5+1). The left panel shows GFP staining only; the right panel shows GFP overlaid with phalloidin staining. SGN, spiral ganglion neurons; SE, sensory epithelium; SV, stria vascularis; SL, spiral limbus. FIG. 1D includes high magnification images of different regions of the cochlea with the highest transduction. FIG. 1E includes high-magnification images of the cochlea with median transduction. FIG. 1F and FIG. 1G are quantification of transduction efficiency in inner hair cells (IHCs) and outer hair cells (OHCs). Bars indicate mean±standard error of mean (SEM). To determine the specified regions, we measured the distance from the apex and used the same value for all cochleas. Not all the cochleas had a preserved basal region, so there are fewer data points for the base.

FIG. 2A shows a low-magnification image of a representative injection in CD1 mouse. Animals (n=5) were injected at P1 with $5 \times 10^{10}$ (vector genome) VGs, and cochleas were explanted at P5 and cultured for another day (P5+1). Left panel shows GFP staining only; right panel shows GFP overlaid with phalloidin staining. FIG. 2B is a high-magnification image of the sensory epithelium of mid-apex region from the same cochlea as in FIG. 2A. FIG. 2C is a quantification of transduction efficiency in IHCs and OHCs. Error bars indicate mean±SEM. FIG. 2D shows transduction efficiency in CD1 compared to C57BL/6J mice (unpaired t test, p<0.001 for IHCs, and p<0.009 for OHCs; data are from all regions analyzed).

FIGS. 3A-3B show anti-Human influenza hemagglutinin (HA) immunostaining of injected C57BL/6J mice. Animals were injected at P1 through the RWM with $7.4 \times 10^{10}$ VGs of AAV9-PHP.B-CBA-HA-Clrn1. Cochleas were explanted at P5 and were cultured for another day (P5+1). Hair bundles were counterstained with phalloidin. FIG. 3C includes higher magnification images of IHCs and OHCs at different focal planes. Strong fluorescence labeling was observed in the hair bundle region, cuticular plate, and kinocilium. In the cell body, diffuse cytoplasmic staining was detected. FIG. 3D shows proportion of inner and outer hair cells with HA-positive bundles, (n=6); dashed red traces indicate mean±SEM. FIG. 3E and FIGS. 3G-3J show auditory brainstem response (ABR) of mice injected with AAV9-PHP.B-CBA-Clrn1 (tagless, no HA tag, $1.8 \times 10^{11}$ VGs were injected). An ABR assay was performed at 4 weeks for vector-injected (right panel; n=17) and non-injected (left panel; n=10) animals. In each panel, the ABR from 4-week-old wild-type C57BL/6J animals is indicated for comparison (n=2; mean±SD). FIG. 3F shows ABR testing of AAV9-PHP.B-mediated expression of clarin1 on hearing in wild-type C57BL/6J mice (n=7; mean±SD).

FIG. 4A shows many retinal cells were transduced 8 days post-injection. FIG. 4B shows numerous photoreceptors were GFP positive as well as a few cells in the ganglion cell layer (GCL; small arrowheads) and the inner nuclear layer (INL; large arrowhead). GCL, ganglion cell layer; INL, inner nuclear layer; ONL, outer nuclear layer; IS, inner segment; OS, outer segment.

FIG. 5A shows low-magnification images of the injected ear (top) and non-injected (bottom) ear. Anti-GFP staining was detected with a horseradish-peroxidase-conjugated secondary antibody and developed using diaminobenzidine (brown areas). Slides were counterstained with hematoxylin. FIG. 5B-5C show higher magnification images of the organ of Corti from base to apex. The non-injected ear lacks GFP-specific immunoreactivity. IHCs are indicated with arrowheads; OHCs are indicated with arrows. FIG. 5D-5F show transduction of the lateral wall at high and low magnification and transduction of spiral ganglion neurons. We observed dim but consistent staining in the injected ear (top) but not the non-injected ear (bottom).

Figure 1A:
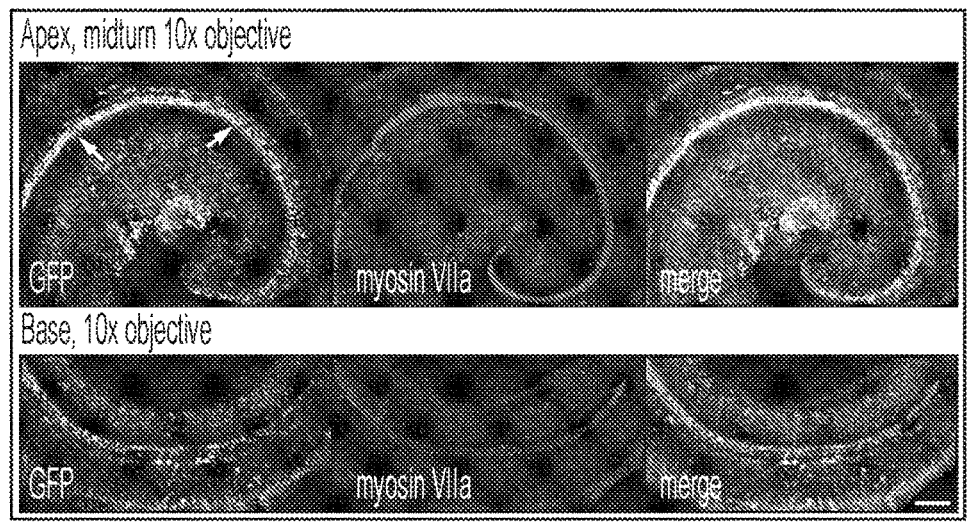
FIGS. 1A-1G are pictures and charts showing AAV9.PHP.B successfully transduced into inner hair cell and outer hair cell to express green fluorescent protein (GFP).

The drawings and examples provided herein are not meant to be limiting.

DETAILED DESCRIPTION OF INVENTION

In some aspects, the disclosure relates to compositions and methods useful for treating certain genetic diseases, for example, autosomal recessive disorder, etc. Autosomal recessive disorders are diseases that result from abnormal expression or function of both alleles of a gene. Examples of autosomal recessive disorder include, but are not limited to, hereditary hearing loss (e.g., Usher syndrome or Nonsyndromic hearing loss and deafness (DFNB1)), Tay-Sachs disease, cystic fibrosis, sickle cell disease, autosomal recessive polycystic kidney disease (ARPKD), and phenylketonuria (PKU).

Adeno-associated virus (AAV) mediated gene therapy is one approach for the treatment of genetic diseases. Recombinant AAV (rAAV) has been developed to treat various genetic disorders. The present disclosure, at least in part, relates to the unexpected finding of an rAAV.PHP.B capable of delivering a transgene to most cochlear cells (e.g., inner hair cells, outer hair cells, and fibrocytes) and cells in the eye (e.g., photoreceptors) across multiple species (e.g., mouse, rat, or non-human primates) and compositions thereof in the treatment of hereditary hearing loss, for example, Usher syndrome type 3A or DFNB1. The disclosure is based, in part, on recombinant AAV vectors (e.g., isolated nucleic acids) and recombinant adeno-associated viruses (rAAVs), e.g., rAAV9.PHP.B, comprising expression cassettes configured for expression of clarin-1 or gap junction beta 2 (GJB2) in the ear of multiple species (e.g., mouse, rat, non-human primate, or human).

I. Isolated Nucleic Acid

In some aspects, the disclosure provides isolated nucleic acids that are useful for expressing human clarin-1 or human GJB2.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulatable by standard techniques known to those of ordinary skill in the art.

The isolated nucleic acids of the invention may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR). The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences (e.g., a promoter), and 5' and 3' AAV inverted terminal repeats (ITRs). The transgene may comprise, as disclosed elsewhere herein, a nucleic acid sequence encoding a protein (e.g., human clarin-1, or human GJB2).

Aspects of the present disclosure relates to an isolated nucleic acid comprising a transgene encoding clarin-1. The CLRN1 gene encodes for clarin-1 protein. Alternative splice forms of clarin-1 have been identified. Isoform 2 of clarin-1, which consists of exons 1, 3 and 4, is the predominant isoform of clarin-1 expressed at all ages. Isoform 3 can also be expressed in the inner ear, but thought to be non-functional due to the lack of a conserved transmembrane domain. Clarin-1 isoform 2 coding sequence is less than 1 kb, which is small enough to be packaged into an AAV genome. Clarin-1 isoform 2 coding sequence encodes a 232-amino acid tetraspan-like glycoprotein. In some embodiments, the transgene encodes clarin-1 isoform 2. Exemplary amino acid sequence of Clarin-1 isoform 2 is set forth in SEQ ID NO: 1. In some embodiments, the transgene encodes for clarin-1 having an amino acid sequence at least 70%, 75%, 80%, 85%, 90%, 91&, 92%, 93%, 94%, 95%, 96%, 97%, 98%, 99%, or 100% identical to amino acid sequence of SEQ ID NO: 1. The nucleic acid sequence encoding clarin-1 isoform 2 is set forth in SEQ ID NO: 2.

```
Clarin-1 isoform 2 amino acid sequence
(SEQ ID NO: 1):
MPSQQKKIIFCMAGVLSFLCALGVVTAVGTPLWVKATILCKTGALLVNAS

GKELDKFMGEMQYGLFHGEGVRQCGLGARPFRFSFFPDLVQAIPVSIHIN

IILFSMILVVLTMVGTAFFMYNAFGKPFETLHGPLGLYLVSFISGSCGCL

VMILFASEVKVHRLSEKIANFKEGTYAYRTQNENYTTSFWVVFICFFVHF

LNGLLIRLAGFQFPFTKSKETETTNVASDLMY

Nucleic acid sequence encoding clarin-1 isoform 2
(SEQ ID NO: 2):
ATGCCAAGCCAGCAGAAGAAGATCATCTTTTGCATGGCTGGCGTACTGAG

CTTTCTCTGTGCTCTTGGAGTGGTGACAGCAGTGGGCACCCCACTGTGGG

TTAAAGCCACTATCCTCTGCAAAACAGGGGCTCTGCTTGTCAACGCGTCA

GGGAAGGAGCTGGACAAGTTCATGGGCGAGATGCAGTATGGCCTTTTCCA

CGGAGAAGGCGTAAGGCAATGTGGGTTAGGAGCAAGGCCTTTCCGGTTCT

CATTCTTCCCAGATTTGGTCCAAGCCATCCCCGTAAGCATCCACATCAAT

ATTATTCTCTTCTCCATGATTCTTGTCGTCTTAACCATGGTGGGGACAGC

CTTCTTCATGTACAATGCTTTTGGCAAGCCCTTTGAAACTCTTCATGGAC

CACTGGGGCTCTATCTGGTCAGCTTCATTTCAGGCTCCTGTGGCTGTCTT

GTCATGATATTGTTTGCCTCTGAAGTGAAAGTCCACCGCCTTTCAGAGAA

AATTGCAAATTTTAAAGAAGGGACCTATGCCTACAGAACACAAACGAAA

ACTATACCACCTCATTCTGGGTTGTTTTCATTTGCTTTTTTGTTCATTTT

TTGAATGGGCTCCTGATACGACTTGCTGGATTTCAGTTCCCTTTCACAAA

ATCTAAAGAAACAGAGACCACTAATGTAGCTTCAGATTTAATGTACTGA
```

In some embodiments, the transgenes encoding a clarin-1 isoform 2 described by the disclosure mediate hair cell synaptic transmission, and are therefore useful for hereditary hearing loss, for example, Usher Syndrome Type 3A. Generally, Usher syndrome refers to a condition characterized by partial or total hearing loss and vision loss that worsens over time. The hearing loss is classified as sensorineural, which means that it is caused by abnormalities of the inner ear. The loss of vision is caused by an eye disease called retinitis pigmentosa (RP), which affects the layer of light-sensitive tissue at the back of the eye (the retina). There are three major types of Usher syndrome, designated as types I, II, and III. These types are distinguished by the severity of hearing loss, the presence or absence of balance problems, and the age at which signs and symptoms appear. The types are further divided into subtypes based on their genetic cause. Usher Syndrome, Type 3A is characterized by post-lingual, progressive hearing loss, variable vestibular dysfunction, and onset of retinitis pigmentosa symptoms, including nyctalopia, constriction of the visual fields, and loss of central visual acuity, usually by the second decade of life. Usher Syndrome, Type 3A is caused by mutations in CLRN encoding clarin-1.

Other aspects of the present disclosure relate to an isolated nucleic acid comprising a transgene encoding a gap junction beta 2 (GJB2). The GJB2 gene encodes for GJB2 protein. In some embodiments, the transgene encodes human GJB2. An exemplary amino acid sequence of human GJB2 is set forth in SEQ ID NO: 3. In some embodiments, the transgene encodes for a GJB2 having an amino acid sequence at least 70%, 75%, 80%, 85%, 90%, 91&, 92%, 93%, 94%, 95%, 96%, 97%, 98%, 99%, or 100% identical to amino acid sequence of SEQ ID NO: 3. The nucleic acid sequence encoding human GJB2 is set forth in SEQ ID NO: 4. In some embodiments, the transgene encodes a mouse GJB2. An exemplary amino acid sequence of mouse GJB2 is set forth in SEQ ID NO: 5. In some embodiments, the transgene encodes for a GJB2 having an amino acid sequence at least 70%, 75%, 80%, 85%, 90%, 91&, 92%, 93%, 94%, 95%, 96%, 97%, 98%, 99%, or 100% identical to amino acid sequence of SEQ ID NO: 5. The nucleic acid sequence encoding mouse GJB2 is set forth in SEQ ID NO: 6.

```
Human GJB2 amino acid sequence (SEQ ID NO: 3):
MDWGTLQTILGGVNKHSTSIGKIWLTVLFIFRIMILVVAAKEVWGDEQAD

FVCNTLQPGCKNVCYDHYFPISHIRLWALQLIFVSTPALLVAMHVAYRRH

EKRKFIKGEIKSEFKDIEEIKTQKVRIEGSLWWTYTSSIFFRVIFEAAFM

YVFYVMYDGFSMQRLVKCNAWPCPNTVDCFVSRPTEKTVFTVFMIAVSGI

CILLNVTELCYLLIRYCSGKSKKPV

Nucleic acid sequence encoding human GJB2
(SEQ ID NO: 4):
ATGGATTGGGGCACGCTGCAGACGATCCTGGGGGGTGTGAACAAACACTC

CACCAGCATTGGAAAGATCTGGCTCACCGTCCTCTTCATTTTTCGCATTA

TGATCCTCGTTGTGGCTGCAAAGGAGGTGTGGGGAGATGAGCAGGCCGAC

TTTGTCTGCAACACCCTGCAGCCAGGCTGCAAGAACGTGTGCTACGATCA

CTACTTCCCCATCTCCCACATCCGGCTATGGGCCCTGCAGCTGATCTTCG

TGTCCACGCCAGCGCTCCTAGTGGCCATGCACGTGGCCTACCGGAGACAT

GAGAAGAAGAGGAAGTTCATCAAGGGGGAGATAAAGAGTGAATTTAAGGA

CATCGAGGAGATCAAAACCCAGAAGGTCCGCATCGAAGGCTCCCTGTGGT

GGACCTACACAAGCAGCATCTTCTTCCGGGTCATCTTCGAAGCCGCCTTC

ATGTACGTCTTCTATGTCATGTACGACGGCTTCTCCATGCAGCGGCTGGT

GAAGTGCAACGCCTGGCCTTGTCCCAACACTGTGGACTGCTTTGTGTCCC

GGCCCACGGAGAAGACTGTCTTCACAGTGTTCATGATTGCAGTGTCTGGA
```

-continued

ATTTGCATCCTGCTGAATGTCACTGAATTGTGTTATTTGCTAATTAGATA

TTGTTCTGGGAAGTCAAAAAAGCCAGTT

Mouse GJB2 amino acid seuquence (SEQ ID NO: 5)
MDWGTLQSILGGVNKHSTSIGKIWLTVLFIFRIMILVVAAKEVWGDEQAD

FVCNTLQPGCKNVCYDHHFPISHIRLWALQLIMVSTPALLVAMHVAYRRH

EKKRKFMKGEIKNEFKDIEEIKTQKVRIEGSLWWTYTTSIFFRVIFEAVF

MYVFYIMYNGFFMQRLVKCNAWPCPNTVDCFISRPTEKTVFTVFMISVSG

ICILLNITELCYLFVRYCSGKSKRPV

Nucleic acid sequence encoding mouse GJB2
(SEQ ID NO: 6)
GACAAGATGGATTGGGGCACACTCCAGAGCATCCTCGGGGGTGTCAACAA

ACACTCCACCAGCATTGGAAAGATCTGGCTCACGGTCCTCTTCATCTTCC

GCATCATGATCCTCGTGGTGGCTGCAAAGGAGGTGTGGGGAGATGAGCAA

GCCGATTTTGTCTGCAACACGTCCAGCCTGGCTGCAAGAATGTATGCTA

CGACCACCACTTCCCCATCTCTCACATCCGGCTCTGGGCTCTGCAGCTGA

TCATGGTGTCCACGCCAGCCCTCCTGGTAGCTATGCATGTGGCCTACGG

AGACATGAAAAGAAACGGAAGTTCATGAAGGGAGAGATAAAGAACGAGTT

TAAGGACATCGAAGAGATCAAAACCCAGAAGGTCCGTATCGAAGGGTCCC

TGTGGTGGACCTACACCACCAGCATCTTCTTCCGGGTCATCTTTGAAGCC

GTCTTCATGTACGTCTTTTACATCATGTACAATGGCTTCTTCATGCAACG

TCTGGTGAAATGCAACGCTTGGCCCTGCCCCAATACAGTGGACTGCTTCA

TTTCCAGGCCCACAGAAAAGACTGTCTTCACCGTGTTTATGATTTCTGTG

TCTGGAATTTGCATTCTGCTAAATATCACAGAGCTGTGCTATTTGTTCGT

TAGGTATTGCTCAGGAAAGTCCAAAAGACCAGTC

In some embodiments, the transgenes encoding a GJB2 described by the disclosure mediate the transport of nutrients, charged atoms (ions), and signaling molecules between adjoining cells. GJB2 also plays a role in maintenance of the proper level of potassium ions in the inner ear and facilitating the maturation of certain cells in the cochlea. GJB2 was recognized as the causative gene for Non-syndromic hearing loss DFNB1-type non-syndromic hearing loss and deafness. Therefore, replacing mutated GJB2 with functional GJB2 can be useful gene therapy for treating DFNB1. Non-syndromic hearing loss is characterized by mild to profound hearing loss that is present before a child learns to speak (prelingual) and does not become more severe over time. More than 100 GJB2 gene mutations were identified to cause nonsyndromic hearing loss and deafness. The GJB2 gene mutations that result in DFNB1 are described as "loss of function" because they lead to an altered or nonfunctional version of GJB2, which appears to disrupt the assembly or function of gap junctions. In the inner ear, the abnormal or missing gap junctions likely alter the levels of potassium ions, which may affect the function and survival of cells that are needed for hearing.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., *Molecular Cloning. A Laboratory Manual,* 2d ed., Cold Spring Harbor Laboratory, New York (1989); and K. Fisher et al., *J. Virol.,* 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid comprises at least one ITR having a serotype selected from AAV1, AAV2, AAV5, AAV6, AAV6.2, AAV7, AAV8, AAV9, AAV10, and AAV11. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ATRS ITR). Without wishing to be bound by any particular theory, a rAAV vector comprising an ITR lacking a functional TRS produces a self-complementary rAAV vector, for example, as described by McCarthy (2008) *Molecular Therapy* 16(10):1648-1656. Any referenced cited in the present disclosure are incorporated by reference in its entirety.

In addition to the major elements identified above for the recombinant AAV vector, the vector also includes conventional control elements which are operably linked with elements of the transgene in a manner that permits its transcription, translation, and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter, and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized. In some embodiments, the transgene comprises a Kozak consensus sequence at the 5' end of the nucleic acid sequence encoding the transgene (e.g., CLRN1 or GJB2).

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein.

A "promoter" refers to a DNA sequence recognized by the synthetic machinery of the cell, or introduced synthetic machinery, required to initiate the specific transcription of a gene. The phrases "operatively positioned," "under control," or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is hybrid cytomegalovirus (CMV) immediate-early/Chicken beta-actin promoter. In some embodiments, a promoter is a chicken beta-actin (CBA) promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the tissue-specific promoter is an eye-specific promoter. Examples of eye-specific promoters include but are not limited to a retinoschisin promoter, K12 promoter, a rhodopsin promoter, a rod-specific promoter, a cone-specific promoter, a rhodopsin kinase promoter, a GRK1 promoter, an interphotoreceptor retinoid-binding protein proximal (IRBP) promoter, and an opsin promoter (e.g., a red opsin promoter, a blue opsin promoter, etc.).

The present disclosure, provides vectors (e.g., AAV vectors) for expressing a transgene (e.g., CLRN1 or GJB2), such vectors include AAV LTRs (e.g., AAV2 LTRs) and a transgene operably linked to a promoter (e.g., chicken beta actin promoter). In addition, the vector can further comprise certain regulatory elements (e.g., enhancers, kozak sequences, and poly adenylation sites).

II. Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa, and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV1, AAV2, AAV3, AAV4, AAV5, AAV6, AAV7, AAV8, AAVrh8, AAV9, AAV10, AAVrh10, and AAV.PHP.B. In some embodiments, an AAV capsid protein is of a serotype derived from a non-human primate, for example, AAVrh8 serotype. In some embodiments, the capsid protein is of AAV serotype 9 (AAV9). In some embodiments, an AAV capsid protein is of a serotype derived from AAV9, for example AAV9.PHP.B. In some embodiments, the AAV capsid protein comprises the sequence at least 60%, 70%, 80%, 85%, 90%, 91%, 92%, 93%, 94%, 95%, 96%, 97%, 98%, 99% or 100% identical to the amino acid sequence set forth in SEQ ID NO: 7. In one example, the AAV9.PHP.B capsid protein comprises a 7mer amino acid insert at amino acid positions of 588-595 of SEQ ID NO: 7 which has an amino acid sequence of TLAVPFK (SEQ ID NO: 8). The present disclosure, at least in part, is based on the unexpected finding that AAV9.PHP.B capsid, which was derived for delivery of transgenes to central nervous system (e.g., neurons), has tropism for cells in the ear (e.g., inner ear cells, out hair cells and fibrocytes) and cells in the eye (e.g., photoreceptors).

```
Exemplary acid sequence of AAV9.PHP.B is set
forth in SEQ ID NO: 7 (7mer amino acid insert
in boldface)
MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS
```

```
-continued
LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSRT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQTLAVPFKAQAQT

GWVQNQGILPGMVWQDRDVYLQGPIWAKIPHTDGNFHPSPLMGGFGMKHP

PPQILIKNTPVPADPPTAFNKDKLNSFITQYSTGQVSVEIEWELQKENSK

RWNPEIQYTSNYYKSNNVEFAVNTEGVYSEPRPIGTRYLTRNL

The nucleic acid sequence encoding the AAV9.PHP.B
is set forth in SEQ ID NO: 9.
ATGGCTGCCGATGGTTATCTTCCAGATTGGCTCGAGGACAACCTTAGTGA

AGGAATTCGCGAGTGGTGGGCTTTGAAACCTGGAGCCCCTCAACCCAAGG

CAAATCAACAACATCAAGACAACGCTCGAGGTCTTGTGCTTCCGGGTTAC

AAATACCTTGGACCCGGCAACGGACTCGACAAGGGGGAGCCGGTCAACGC

AGCAGACGCGGCGGCCCTCGAGCACGACAAGGCCTACGACCAGCAGCTCA

AGGCCGGAGACAACCCGTACCTCAAGTACAACCACGCCGACGCCGAGTTC

CAGGAGCGGCTCAAAGAAGATACGTCTTTTGGGGGCAACCTCGGCGAGC

AGTCTTCCAGGCCAAAAAGAGGCTTCTTGAACCTCTTGGTCTGGTTGAGG

AAGCGGCTAAGACGGCTCCTGGAAAGAAGAGGCCTGTAGAGCAGTCTCCT

CAGGAACCGGACTCCTCCGCGGGTATTGGCAAATCGGGTGCACAGCCCGC

TAAAAAGAGACTCAATTTCGGTCAGACTGGCGACACAGAGTCAGTCCCAG

ACCCTCAACCAATCGGAGAACCTCCCGCAGCCCCCTCAGGTGTGGGATCT

CTTACAATGGCTTCAGGTGGTGGCGCACCAGTGGCAGACAATAACGAAGG

TGCCGATGGAGTGGGTAGTTCCTCGGGAAATTGGCATTGCGATTCCCAAT

GGCTGGGGGACAGAGTCATCACCACCAGCACCCGAACCTGGGCCCTGCCC

ACCTACAACAATCACCTCTACAAGCAAATCTCCAACAGCACATCTGGAGG

ATCTTCAAATGACAACGCCTACTTCGGCTACAGCACCCCCTGGGGGTATT

TTGACTTCAACAGATTCCACTGCCACTTCTCACCACGTGACTGGCAGCGA

CTCATCAACAACAACTGGGGATTCCGGCCTAAGCGACTCAACTTCAAGCT

CTTCAACATTCAGGTCAAAGAGGTTACGGACAACAATGGAGTCAAGACCA

TCGCCAATAACCTTACCAGCACGGTCCAGGTCTTCACGGACTCAGACTAT

CAGCTCCCGTACGTGCTCGGGTCGGCTCACGAGGGCTGCCTCCCGCCGTT

CCCAGCGGACGTTTTCATGATTCCTCAGTACGGGTATCTGACGCTTAATG

ATGGAAGCCAGGCCGTGGGTCGTTCGTCCTTTTACTGCCTGGAATATTTC

CCGTCGCAAATGCTAAGAACGGGTAACAACTTCCAGTTCAGCTACGAGTT

TGAGAACGTACCTTTCCATAGCAGCTACGCTCACAGCCAAAGCCTGGACC

GACTAATGAATCCACTCATCGACCAATACTTGTACTATCTCTCAAGAACT

ATTAACGGTTCTGGACAGAATCAACAAACGCTAAAATTCAGTGTGGCCGG

ACCCAGCAACATGGCTGTCCAGGGAAGAAACTACATACCTGGACCCAGCT
```

-continued

ACCGACAACAACGTGTCTCAACCACTGTGACTCAAAACAACAACAGCGAA

TTTGCTTGGCCTGGAGCTTCTTCTTGGGCTCTCAATGGACGTAATAGCTT

GATGAATCCTGGACCTGCTATGGCCAGCCACAAAGAAGGAGAGGACCGTT

TCTTTCCTTTGTCTGGATCTTTAATTTTTGGCAAACAAGGAACTGGAAGA

GACAACGTGGATGCGGACAAAGTCATGATAACCAACGAAGAAGAAATTAA

AACTACTAACCCGGTAGCAACGGAGTCCTATGGACAAGTGGCCACAAACC

ACCAGAGTGCCCAAACTTTGGCGGTGCCTTTTAAGGCACAGGCGCAGACC

GGCTGGGTTCAAAACCAAGGAATACTTCCGGGTATGGTTTGGCAGGACAG

AGATGTGTACCTGCAAGGACCCATTTGGGCCAAAATTCCTCACACGGACG

GCAACTTTCACCCTTCTCCGCTGATGGGAGGGTTTGGAATGAAGCACCCG

CCTCCTCAGATCCTCATCAAAAACACACCTGTACCTGCGGATCCTCCAAC

GGCCTTCAACAAGGACAAGCTGAACTCTTTCATCACCCAGTATTCTACTG

GCCAAGTCAGCGTGGAGATCGAGTGGGAGCTGCAGAAGGAAAACAGCAAG

CGCTGGAACCCGGAGATCCAGTACACTTCCAACTATTACAAGTCTAATAA

TGTTGAATTTGCTGTTAATACTGAAGGTGTATATAGTGAACCCCGCCCCA

TTGGCACCAGATACCTGACTCGTAATCTGTAA

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., *Molecular Cloning: A Laboratory Manual*, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

In some embodiments, the rAAV is a single stranded AAV (ssAAV). An ssAAV, as used herein, refers to a rAAV with the coding sequence and complementary sequence of the transgene expression cassette on separate strands and are packaged in separate viral capsids. In some embodiments, the rAAV is a self-complementary AAV (scAAV). A scAAV, as used herein, refers to an rAAV with both the coding and complementary sequence of the transgene expression cassette are present on each plus- and minus-strand genome. The coding region of a scAAV was designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription.

In some embodiments, the rAAV as provided herein, is capable of delivering the transgene (e.g., CLRN1 or GJB2) to a mammal. In some examples, the mammal can be a human or a non-human mammal, such as a mouse, a rat, or a non-human primate (e.g., cynomolgus monkey).

In some embodiments, the rAAV, as provided herein, is capable of delivering the transgene (e.g., CLRN1 or GJB2) to the ear. In some instances, the rAAV as provided herein, is capable of delivering the transgene (e.g., CLRN1 or GJB2) to the cells in the inner ear (e.g., cochlear). Non limiting examples of the cells in the cochlear are outer hair cells (OHC), inner hair cells (IHC), spiral ganglion neurons, stria vascularis, inner sulcus, spiral ligament, or vestibular system. In other examples, the cells in the cochlear are fibrocytes lining the inner ear. In other embodiments, the cells can be cells of the eye. In some examples, the cells can be photoreceptors.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a protein (e.g., clarin-1 or GJB2). In some embodiments, the host cell is a mammalian cell (e.g., a human cell), a yeast cell, a bacterial cell, an insect cell, a plant cell, or a fungal cell.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., *Molecular Cloning: A Laboratory Manual*, Cold Spring Harbor Press, Cold Spring Harbor, N.Y. Similarly, methods of generating rAAV virions are well known and the selection of a suitable method is not a limitation on the present disclosure. See, e.g., K. Fisher et al., *J. Virol.*, 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses, such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

The present disclosure, provides a rAAV (e.g., scAAV or ssAAV) comprising a vector (e.g., AAV vectors) for expressing a transgene (e.g., CLRN1 or GJB2), such vectors include AAV LTRs (e.g., AAV2 LTRs) and a transgene operably linked to a promoter (e.g., chicken beta actin promoter). In addition, the vector can further comprise certain regulatory elements (e.g., enhancers, kozak sequences, and poly adenylation sites). In addition, the rAAV can comprise a capsid protein (e.g., AAV9.PHP.B capsid). Such rAAV can deliver transgenes (e.g., CLRN1 or GJB2) to target tissues (e.g., ear or eyes). In some embodiments, such rAAV is capable of delivering transgenes (CLRN1 or GJB2) into specific cells in the target tissue, for example, inner hair cell, out hair cell, fibrocytes of the inner ear, or photoreceptors of the eye, etc.

III. Pharmaceutical Composition for Delivering Transgenes to the Ear

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., cynomolgus monkey).

Delivery of the rAAVs to a mammalian subject may be by, for example, injection to the ear or the eye. In some embodiments, the injection is to the ear through round window membrane of the inner ear or topical administration (e.g., ear drops). In some embodiments, the injection is the eye (e.g., intravitreal injection) or topical administration (e.g., eye drops). In some embodiments, the injection is not topical administration. Combinations of administration methods (e.g., topical administration and injection through round window membrane of the inner ear) can also be used.

The compositions of the disclosure may comprise a rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The *Science* and Practice of Pharmacy 20th Ed. (2000) Lippincott Williams and Wilkins, Ed. K. E. Hoover. For example, one acceptable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

The rAAV containing pharmaceutical composition disclosed herein may further comprise a suitable buffer agent. A buffer agent is a weak acid or base used to maintain the pH of a solution near a chosen value after the addition of another acid or base. In some examples, the buffer agent disclosed herein can be a buffer agent capable of maintaining physiological pH despite changes in carbon dioxide concentration (produced by cellular respiration). Exemplary buffer agents include, but are not limited to, HEPES (4-(2-hydroxyethyl)-1-piperazineethanesulfonic acid) buffer, Dulbecco's phosphate-buffered saline (DPBS) buffer, or Phosphate-buffered Saline (PBS) buffer. Such buffers may comprise disodium hydrogen phosphate and sodium chloride, or potassium dihydrogen phosphate and potassium chloride.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAV containing pharmaceutical composition described herein comprises one or more suitable surface-active agents, such as a surfactant. Surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Suitable surfactants include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

The rAAVs are administered in sufficient amounts to transfect the cells of a desired tissue (e.g., inner hair cells, outer hair cells, fibrocytes in the inner ear or photoreceptors of the eye) and to provide sufficient levels of gene transfer and expression without undue adverse effects. Examples of pharmaceutically acceptable routes of administration include, but are not limited to, direct delivery to the selected organ (e.g., the ear), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of a rAAV is an amount sufficient to target infect an animal (e.g., mouse, rat, non-human primate or human), target a desired tissue (e.g., the inner ear or the eye). The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^9$ rAAV genome copies is effective to target inner ear tissue (e.g., inner hair cells, out hair cells or fibrocytes of the inner ear). In some embodiments, a dose more concentrated than $10^9$ rAAV genome copies is toxic when administered to the eye of a subject. In some embodiments, an effective amount is produced by multiple doses of a rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright et al., *Molecular Therapy* (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to inner ear tissue (e.g., inner hair cells, outer hair cells or fibrocytes of the inner ear). In other embodiments, the target tissue can be an eye. The rAAVs in suitably formulated pharmaceutical compositions disclosed herein are delivered directly to the eye (e.g., photoreceptors). However, in certain circumstances it may be desirable to separately or in addition deliver the rAAV-based therapeutic constructs via another route, e.g., subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

IV. Therapeutic Applications

The present disclosure also provides methods for delivering a transgene to the ear or the eye. In some embodiments, the method is for delivering a transgene to cochlear (e.g., inner hair cells, outer hair cells or fibrocytes of the inner ear) tissue in a subject are provided herein. In other embodiments, the method is for delivering a transgene to the cells in the eye (e.g., photoreceptors). The methods typically involve administering to a subject an effective amount of a rAAV comprising a nucleic acid for expressing a transgene (e.g., CLRN1 or GJB2) in the subject. An "effective amount" of a rAAV is an amount sufficient to infect a sufficient number of cells of a target tissue in a subject. In some embodiments, a target tissue is cochlear (e.g., inner hair cells, outer hair cells or fibrocytes of the inner ear) tissue. An effective amount of a rAAV may be an amount sufficient to have a therapeutic benefit in a subject, e.g., to improve in the subject one or more symptoms of disease, e.g., a symptom of a hereditary hearing loss (e.g., Usher syndrome type 3A or DFNB1). In some cases, an effective amount of a rAAV may be an amount sufficient to produce a stable somatic transgenic animal model. The effective amount will depend on a variety of factors such as, for example, the species, age, weight, health of the subject, and the ocular tissue to be targeted, and may thus vary among subject and tissue.

An effective amount may also depend on the rAAV used. The invention is based, in part on the recognition that rAAV comprising capsid proteins having a particular serotype (e.g., AAV9, and AAV9.PHP.B) mediate more efficient transduction of cochlear (e.g., inner hair cells, out hair cells, or fibrocytes of the inner ear) tissue that rAAV comprising capsid proteins having a different serotype. Thus in some embodiments, the rAAV comprises a capsid protein of an AAV serotype of AAV9 or a variant thereof. In some embodiments, the rAAV comprises a capsid protein of AAV9.PHP.B serotype (SEQ ID NO: 7). In some embodiments, the capsid protein comprises an amino acid sequence that is at least 70%, at least 80%, at least 90%, at least 95%, or at least 99% identical to SEQ ID NO: 7.

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting a cochlear (e.g., inner hair cells, out hair cells, or fibrocytes of the inner ear) tissue by injection through the round window membrane of the inner ear may require different (e.g., higher or lower) doses, in some cases, than targeting an cochlear (e.g., inner hair cells, out hair cells, or fibrocytes of the inner ear) tissue by another method (e.g., systemic administration, topical administration). In other cases, targeting the eye (e.g., photoreceptors) by injection behind the eye (e.g., intravitreal injection) may require different does, in some cases, than targeting the eye (e.g., photoreceptors) by another method (e.g., systemic administration, topical administration). Thus, in some embodiments, the injection is injection through round window membrane of the inner ear. In some embodiments, the administration is via injection, optionally subretinal injection or intravitreal injection. In some embodiments, the injection is topical administration (e.g., topical administration to an ear). In some cases, multiple doses of a rAAV are administered.

Without wishing to be bound by any particular theory, efficient transduction of cochlear (e.g., inner hair cells, out hair cells, or fibrocytes of the inner ear) cells by rAAV described herein may be useful for the treatment of a subject having a hereditary hearing loss (e.g., Usher syndrome type 3A or DFNB1). Accordingly, methods and compositions for treating hereditary hearing loss are also provided herein. In some aspects, the disclosure provides a method for treating a hereditary hearing loss (e.g., Usher syndrome type 3A or DFNB1), the method comprising: administering to a subject having or suspected of having an a hereditary hearing loss an effective amount of rAAV, wherein the rAAV comprises (i) a capsid protein having a serotype of AAV9.PHP.B, and (ii) a nucleic acid comprising a promoter operably linked to a transgene (e.g., a transgene encoding a clarin-1 or GJB2).

In some embodiments, the subject can be a mammal. In some examples, the subject can be a human or a non-human mammal such as mouse, rat, and non-human primate (e.g., cynomolgus monkey).

(i) Methods for Treating Usher Syndrome, Type 3A

Aspects of the invention relate to certain protein-encoding transgenes (e.g., CLRN1) that when delivered to a subject are effective for promoting communication between nerve cells (neurons) in the inner ear and in the retina of the subject. In some embodiments, the subject has or is suspected of having hearing loss and/or vision loss. In some examples, the hearing loss and/or vision loss is associated with a mutation of the CLRN1 gene. In one example, the subject is diagnosed with Usher Syndrome, type 3A.

Accordingly, methods and compositions described by the disclosure are useful, in some embodiments, for the treatment of Usher syndrome, Type 3A associated with mutations or deletions of CLRN1 gene, such as sensorineural hearing loss, deafness, and/or progressive vision loss.

Methods for delivering a transgene (e.g., a gene encoding a clarin-1) to a subject are provided by the disclosure. The methods typically involve administering to a subject an effective amount of an isolated nucleic acid encoding a clarin-1, or a rAAV comprising a nucleic acid for expressing a clarin-1.

In some embodiments, the hearing loss and or vision loss is Usher syndrome type 3A. Generally, a mutation or mutations in CLRN1 account for Usher syndrome, type 3A. In some embodiments, the CLRN1 mutation can be, but are not limited to, point mutations, misssense mutations, nonsense mutations, insertions, or deletions. In some examples, the CLRN1 gene mutations associated with Usher syndrome, type 3A include but are not limited to, c.528T>G, c.149delCAGG/insTGTCCAAT, c.165delC, or c.144T>G, for example, as described by Fields et al. (2002) *Am J Hum Genet.* 71(3):607-617. Mutations in a CLRN1 gene of a subject (e.g., a subject having or suspected of having Usher Syndrome type 3A associated with a deletion or mutation of CLRN1 gene) may be identified from a sample obtained from the subject (e.g., a DNA sample, RNA sample, blood sample, or other biological sample) by any method known in the art. For example, in some embodiments, a nucleic acid (e.g., DNA, RNA, or a combination thereof) is extracted from a biological samples obtained from a subject and nucleic acid sequencing is performed in order to identify a mutation in the CLRN1 gene. Examples of nucleic acids sequencing techniques include but are not limited to Maxam-Gilbert sequencing, pyrosequencing, chain-termination sequencing, massively parallel signature sequencing, single-molecule sequencing, nanopore sequencing, Illumina sequencing, etc. In some embodiments, a mutation in CLRN1 gene is detected indirectly, for example by quantifying clarin-1 protein expression (e.g., by Western blot) or function (e.g., by analyzing structure, function, etc.), or by direct sequencing of the DNA and comparing the sequence obtained to a control DNA sequence (e.g., a wild-type CLRN1 DNA sequence).

In some aspects, the disclosure provides a method for treating an Usher syndrome type 3A in a subject in need thereof, the method comprising administering to a subject having or is suspected of having Usher syndrome type 3A a therapeutically effective amount of an isolated nucleic acid, or a rAAV, through injections to the round window membrane of the inner ear, as described by the disclosure. In other embodiments, the injection is to the eye (e.g., intravitreal injection)

An "effective amount" of a substance is an amount sufficient to produce a desired effect. In some embodiments, an effective amount of an isolated nucleic acid (e.g., an isolated nucleic acid comprising a transgene encoding clarin-1) is an amount sufficient to transfect (or infect in the context of rAAV mediated delivery) a sufficient number of target cells of a target tissue of a subject. In some embodiments, a target tissue is cochlear (e.g., inner hair cells, outer hair cells, etc.). In other embodiments, a target tissue is the eye (e.g., photoreceptors). In some embodiments, an effective amount of an isolated nucleic acid (e.g., which may be delivered via an rAAV) may be an amount sufficient to have a therapeutic benefit in a subject, e.g., to increase or supplement the expression of a gene or protein of interest (e.g., clarin-1), to improve in the subject one or more symptoms of disease (e.g., a symptom of Usher syndrome type 3A), etc. The effective amount will depend on a variety of factors such as, for example, the species, age, weight, health of the subject, and the tissue to be targeted, and may thus vary among subject and tissue as described elsewhere in the disclosure.

(ii) Methods for Treating Nonsyndromic Hearing Loss and Deafness (DFNB1)

Aspects of the invention relate to certain protein-encoding transgenes (e.g., GJB2) that when delivered to a subject are effective for mediate the transport of nutrients, charged atoms (ions), and signaling molecules between adjoining cells in the subject. In some embodiments, the subject has or is suspected of having hearing loss. In some examples, the hearing loss is associated with a mutation of the GJB2 gene. In one example, the subject is diagnosed with Nonsyndromic hearing loss and deafness (DFNB1)

Accordingly, methods and compositions described by the disclosure are useful, in some embodiments, for the treatment of DFNB1 associated with mutations or deletions of GJB2 gene, such as sensorineural hearing loss, deafness, and/or progressive vision loss.

Methods for delivering a transgene (e.g., a gene encoding a GJB2) to a subject are provided by the disclosure. The methods typically involve administering to a subject an effective amount of an isolated nucleic acid encoding a GJB2, or a rAAV comprising a nucleic acid for expressing a GJB2.

In some embodiments, the hearing loss is DFNB1. Generally, a mutation or mutations in GJB2 account for DFNB1. In some embodiments, the GJB2 mutation can be but not limited to point mutations, misssense mutations, nonsense mutations, insertions or deletions. In some examples, the GJB2 gene mutations associated with DFNB1 include but are not limited to c.35delG, c.235delC, or c.167delT. Mutations in a GJB2 gene of a subject (e.g., a subject having or suspected of having DFNB1 associated with a deletion or mutation of GJB2 gene) may be identified from a sample obtained from the subject (e.g., a DNA sample, RNA sample, blood sample, or other biological sample) by any method known in the art. For example, in some embodiments, a nucleic acid (e.g., DNA, RNA, or a combination thereof) is extracted from a biological samples obtained from a subject and nucleic acid sequencing is performed in order to identify a mutation in the GJB2 gene. Examples of nucleic acids sequencing techniques include but are not limited to Maxam-Gilbert sequencing, pyrosequencing, chain-termination sequencing, massively parallel signature sequencing, single-molecule sequencing, nanopore sequencing, Illumina sequencing, etc. In some embodiments, a mutation in GJB2 gene is detected indirectly, for example by quantifying GJB2 protein expression (e.g., by Western blot) or function (e.g., by analyzing structure, function, etc.), or by direct sequencing of the DNA and comparing the sequence obtained to a control DNA sequence (e.g., a wild-type GJB2 DNA sequence).

In some aspects, the disclosure provides a method for treating an DFNB1 in a subject in need thereof, the method comprising administering to a subject having or is suspected of having DFNB1 a therapeutically effective amount of an isolated nucleic acid, or a rAAV, through injections to the round window membrane of the inner ear, as described by the disclosure.

An "effective amount" of a substance is an amount sufficient to produce a desired effect. In some embodiments, an effective amount of an isolated nucleic acid (e.g., an isolated nucleic acid comprising a transgene encoding GJB2) is an amount sufficient to transfect (or infect in the context of rAAV mediated delivery) a sufficient number of target cells of a target tissue of a subject. In some embodiments, a target tissue is cochlear (e.g., fibrocytes of the inner ear, etc.). In some embodiments, an effective amount of an isolated nucleic acid (e.g., which may be delivered via an rAAV) may be an amount sufficient to have a therapeutic benefit in a subject, e.g., to increase or supplement the expression of a gene or protein of interest (e.g., GJB2), to improve in the subject one or more symptoms of disease (e.g., a symptom of DFNB1), etc. The effective amount will depend on a variety of factors such as, for example, the species, age, weight, health of the subject, and the tissue to be targeted, and may thus vary among subject and tissue as described elsewhere in the disclosure.

V. Kits and Related Composition

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid comprising a transgene encoding a clarin-1 (e.g., clarin-1 isoform 2) having the amino acid sequence set forth in SEQ ID NO: 1. In other embodiments, the kit comprising a container housing an isolated nucleic acid comprising a transgene encoding a GJB2 having the amino acid sequence set forth in SEQ ID NO: 3 hair or 5. In some embodiments, the kit further comprises a container housing an isolated nucleic acid encoding an AAV capsid protein, for example, an AAV.PHP.B capsid protein (e.g., SEQ ID NO: 7).

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

Exemplary embodiments of the invention will be described in more detail by the following examples. These embodiments are exemplary of the invention, which one skilled in the art will recognize is not limited to the exemplary embodiments.

VI. General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: AAV9-PHP.B Efficiently Transduces Hair Cells in Neonatal Mice

Figure 1B:
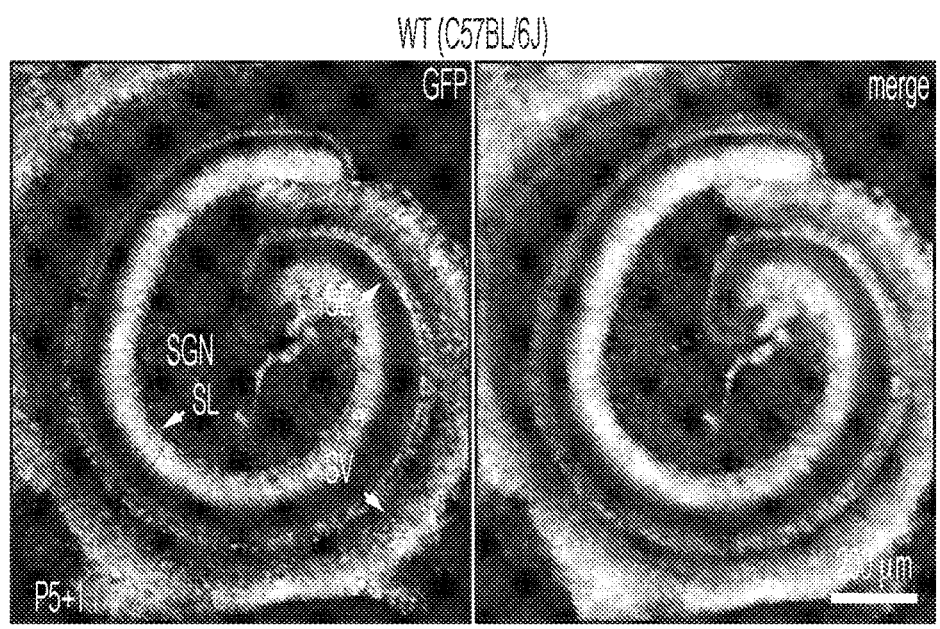
Figure 1C:
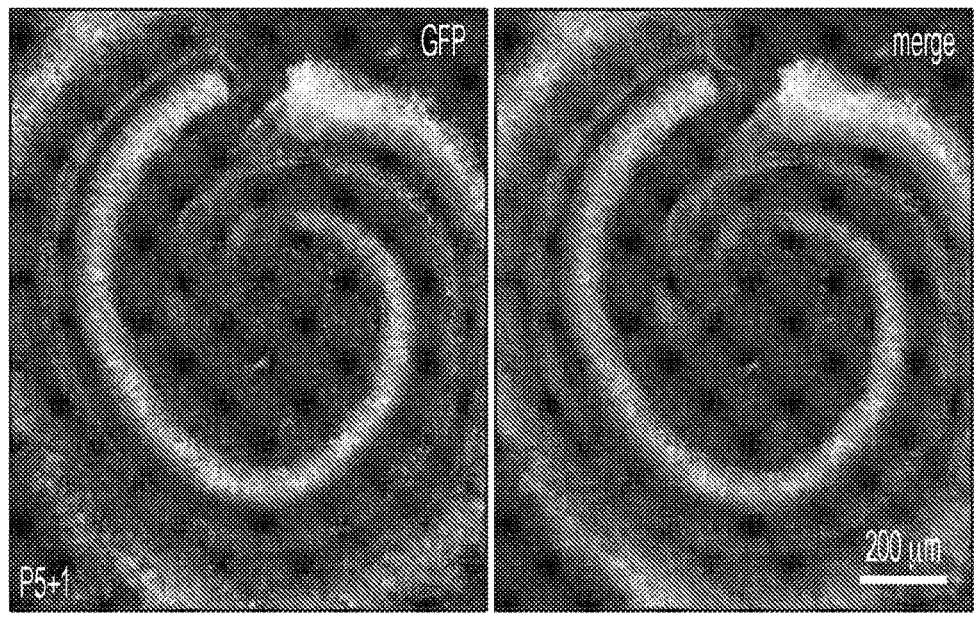
Figure 1D:
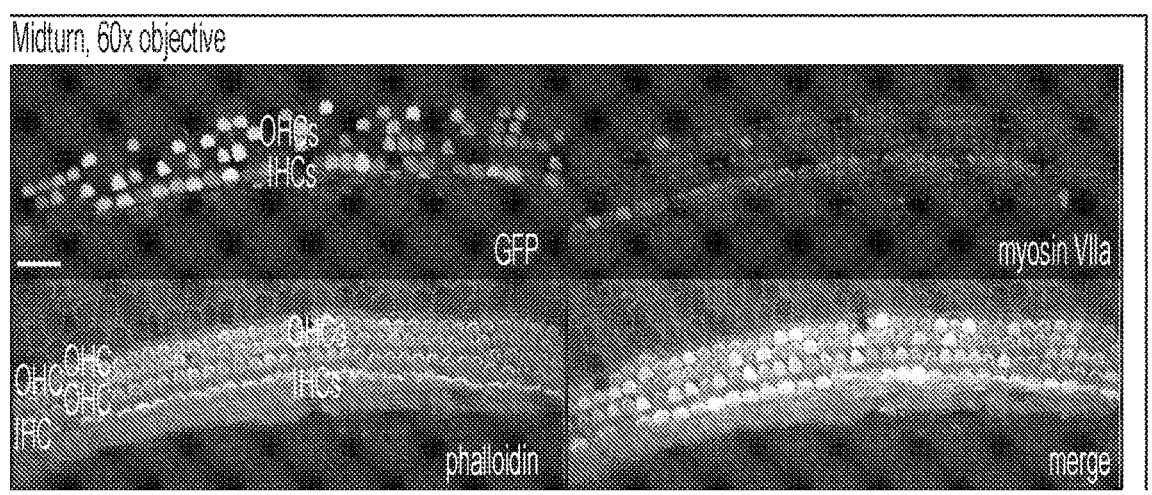
Figure 1E:
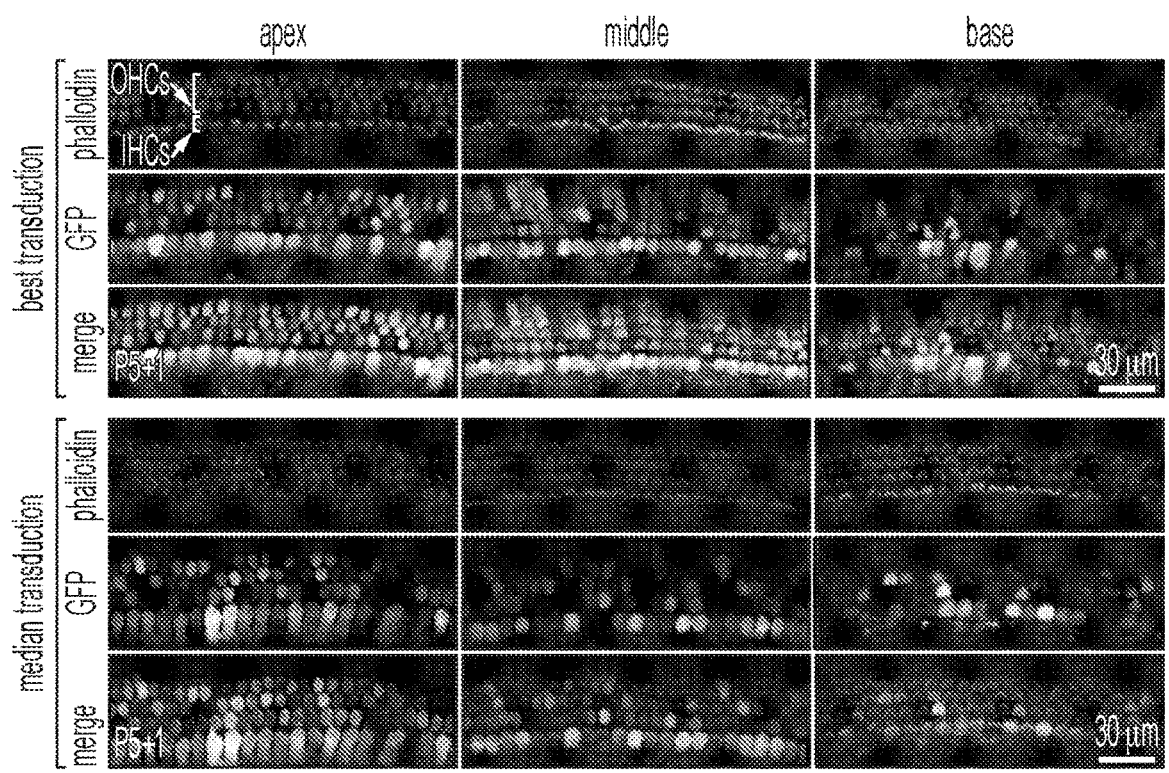
Figure 1F:
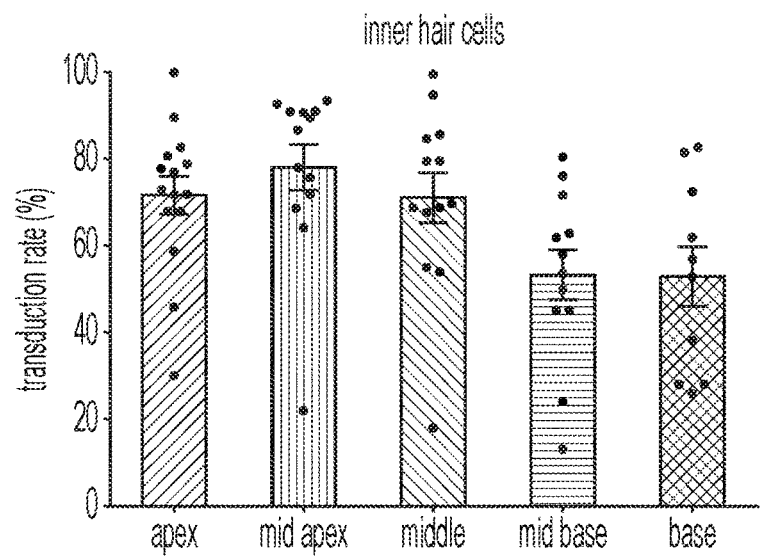
Figure 1G:
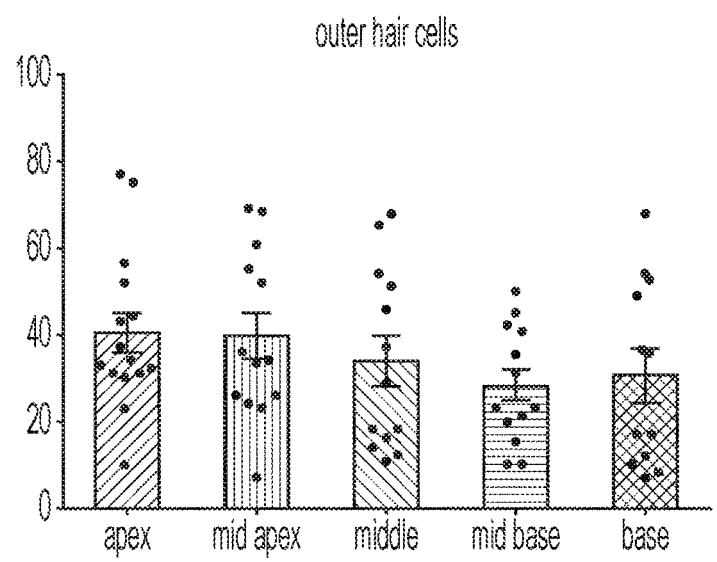

First, the transduction efficiency of AAV9-PHP.B capsid using a single-stranded (ss) AAV transgene expression cassette, with a GFP reporter driven by the chicken beta actin (CBA) promoter was tested. The scalae tympani of the cochleas of neonatal C57BL/6 mice were injected via the RWM at postnatal day 1 (P1) with $5 \times 10^{10}$ vector genomes (VGs) of AAV9-PHP.B-CBA-GFP. Five days later, mice were sacrificed, and cochlear explants were cultured for one additional day before fixation and GFP expression analysis. AAV9-PHP.B mediated efficient transgene expression in inner and outer hair cells of sensory epithelium in neonatal P1 mice after round window membrane (RWM) injection (FIG. 1A). Robust transduction in the spiral ganglion region, sensory epithelium, and lateral wall of the cochlea was observed (FIG. 1B and FIG. 1C). Higher magnification images of the sensory epithelium revealed efficient GFP expression in both IHCs and OHCs (FIG. 1D and FIG. 1E) but not in the supporting cells surrounding the HCs. Transduction efficiency was 60%-80% for IHCs and 30%-40% for OHCs, depending on the location (FIG. 1F and FIG. 1G). For OHCs, there was a significant gradient of transduction from apex to base, with more efficient transduction in the apex (linear regression, R2=0.83, p=0.029), but for IHCs, there was no statistically significant gradient. In one animal (out of five), we observed vector transduction of a few cells in the uninjected contralateral ear. It is possible that some vector diffused through cerebrospinal fluid to the other ear in a neonatal animal.

Figure 2A:
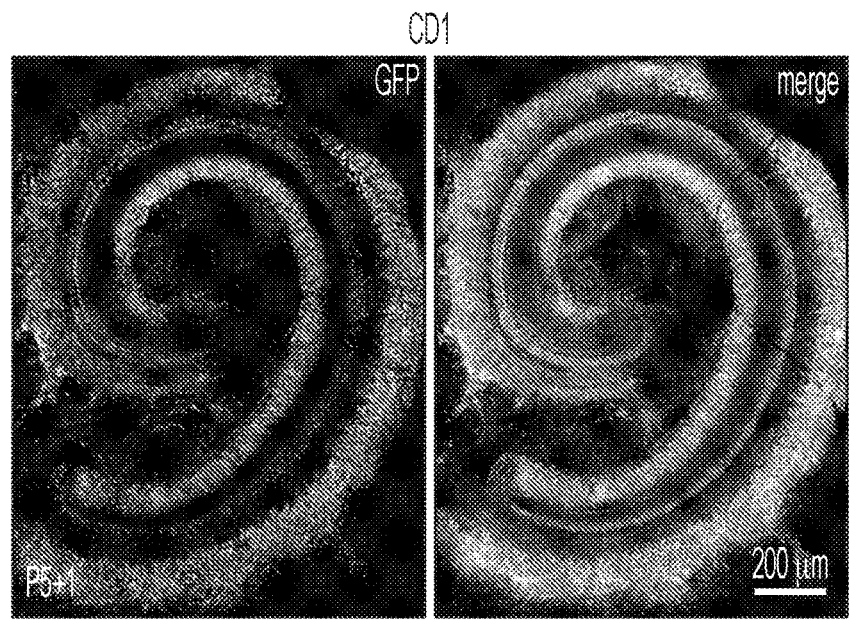
FIGS. 2A-2D are pictures and charts showing transduction efficiency in CD1 mice of AAV9-PHP.B-CBA-GFP after neonatal round window membrane (RWM) injection.
Figure 2B:
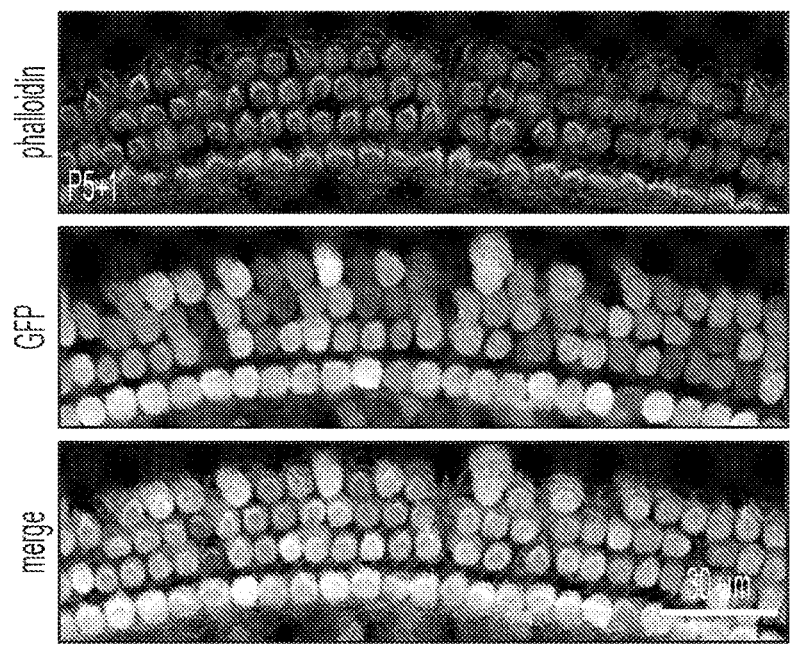
Figure 2C:
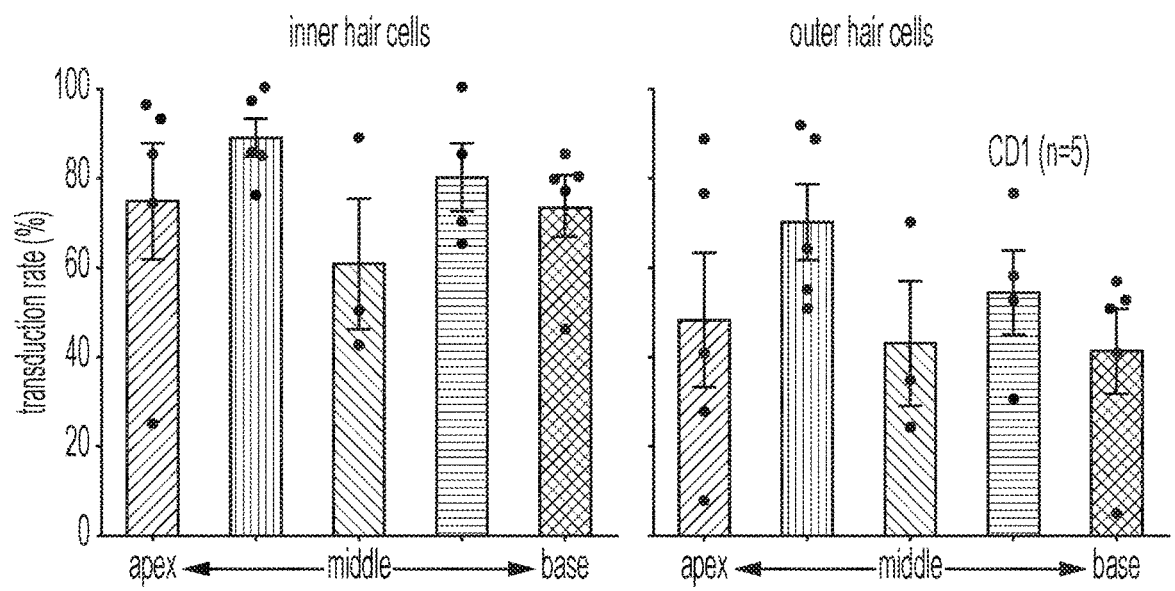
Figure 2D:
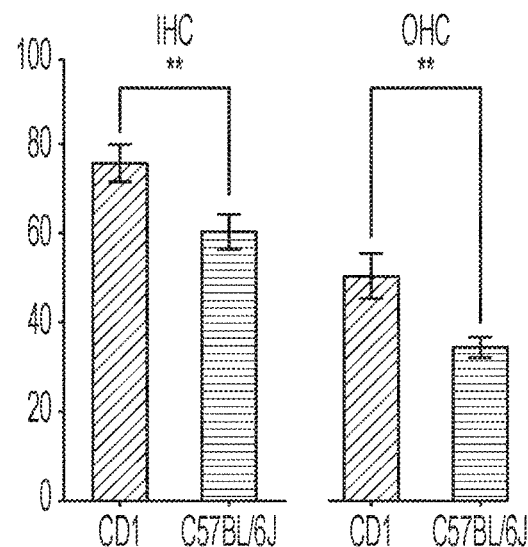

Adult (4-week-old C57BL/6) mice with $2\times10^{10}$ VGs of AAV9-PHP.B-CBA-GFP were injected through the posterior semicircular canal. Although almost all IHCs from apex to base were transduced, no OHC transduction was observed, suggesting that, in mice, AAV9-PHP.B can transduce OHCs only in neonates (at least for the tested delivery routes). Robust transduction of the vestibular system was observed. To investigate whether AAV9-PHP.B efficacy in the neonatal C57BL/6 mouse cochlea would extend to neonatal CD1 mouse cochlea. Injection of AAV9-PHP.B GFP into P1 CD1 mice resulted in robust GFP expression in both IHCs and OHCs in the cochlea (FIG. 2A and FIG. 2B). 60%-80% transduction of IHCs and 40%-70% transduction of OHCs was observed (FIG. 2C). There was significantly higher transduction efficiency in CD1 animals compared to that in C57BL/6 animals (FIG. 2D) (Mann-Whitney test, p<0.04 for IHCs, and p<0.004 for OHCs; data are from all regions analyzed). To investigate whether efficacy translates to another rodent species, Sprague-Dawley rats, two P1 neonatal pups was injected via the RWM at a dose of $1.2\times10^{10}$ VGs. As in neonatal mice, GFP-positive cells in the regions of spiral ganglion, sensory epithelium, and lateral wall were observed. The transduction efficiency was higher in one of the injected rats; higher magnification of the sensory epithelium in that animal revealed robust IHC and OHC transduction.

Taken together, these results confirm that the AAV9-PHP.B capsid is an efficient vector to target neonatal sensory hair cells in two strains of mice as well as in rats.

Example 2: Clrn1 Expression and Function in the Murine Inner Ear

To test AAV9-PHP.B in an animal model of hereditary deafness, a deafness gene for which postnatal treatment is feasible in human was selected. In Usher 3A (caused by mutations in CLRN1), the hearing loss is not profound at birth but is progressive, providing a reasonable window for AAV-mediated gene therapy. Normal Clrn1 expression in the developing inner ear was investigated first. The Shared Harvard Inner-Ear Laboratory Database (SHIELD) revealed highly enriched expression of Clrn1 in cochlear and vestibular HCs relative to non-HCs. Alternative splice forms of Clrn1 have been identified, organs of *Corti* and spiral ganglion regions from embryonic day (E)17 up to P7 in CD1 mice were dissected for RT-PCR analysis with primers in exon 1 and exon 4 of Clrn1. RT-PCR analysis revealed that isoform 2 of Clrn1 (containing exons 1, 3, and 4) was the predominant mRNA species expressed at all ages; however, isoform 3 (containing exons 1 and 4) was also expressed. Based on the predicted tertiary structure of clarin 1 and the fact that the Clrn1 sequence is highly conserved between species, it was expected that isoform 3 would not be functional, as it would lack a conserved transmembrane domain. Isoform 2 was found to be predominant in the retina as well. For therapeutic application, therefore, the mouse codon-optimized cDNA of isoform 2 of Clrn1 was closed into into the AAV expression cassette.

To establish a baseline for rescue, the phenotype of Clrn1$^{-/-}$ mice was evaluated. First, a simple dye loading assay in cochlear explants from heterozygous Clrn1$^{+/-}$ or knockout Clrn1$^{-/-}$ mice was performed. At P5+1, loading of the styryl dye FM1-43 was significantly decreased in both IHCs and OHCs in knockout mice compared to heterozygotes, indicating impaired mechanotransduction and confirming that Clrn1$^{-/-}$ hair bundle morphology revealed loss of orientation and disorganization of hair bundles at P5+1, beginning as early as P0+1.

Figure 3A:
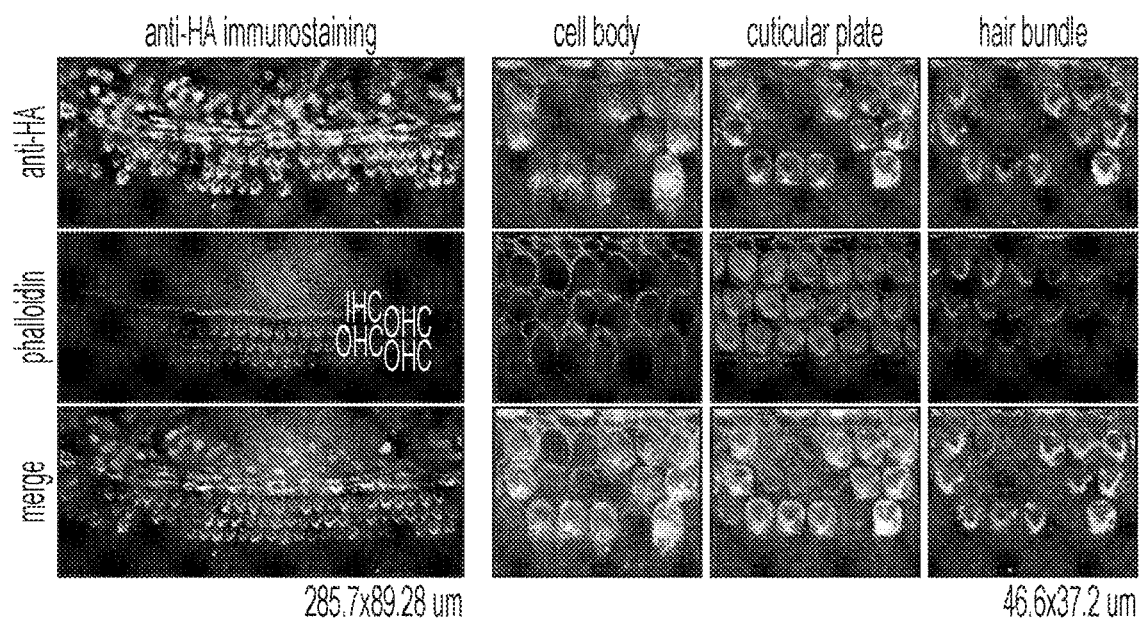
FIG. 3A-3J are pictures and charts showing that AAV-mediated Clrn1 delivery restores protein expression in IHCs and OHCs and rescues hearing in Clrn1 KO animals.
Figure 3B:
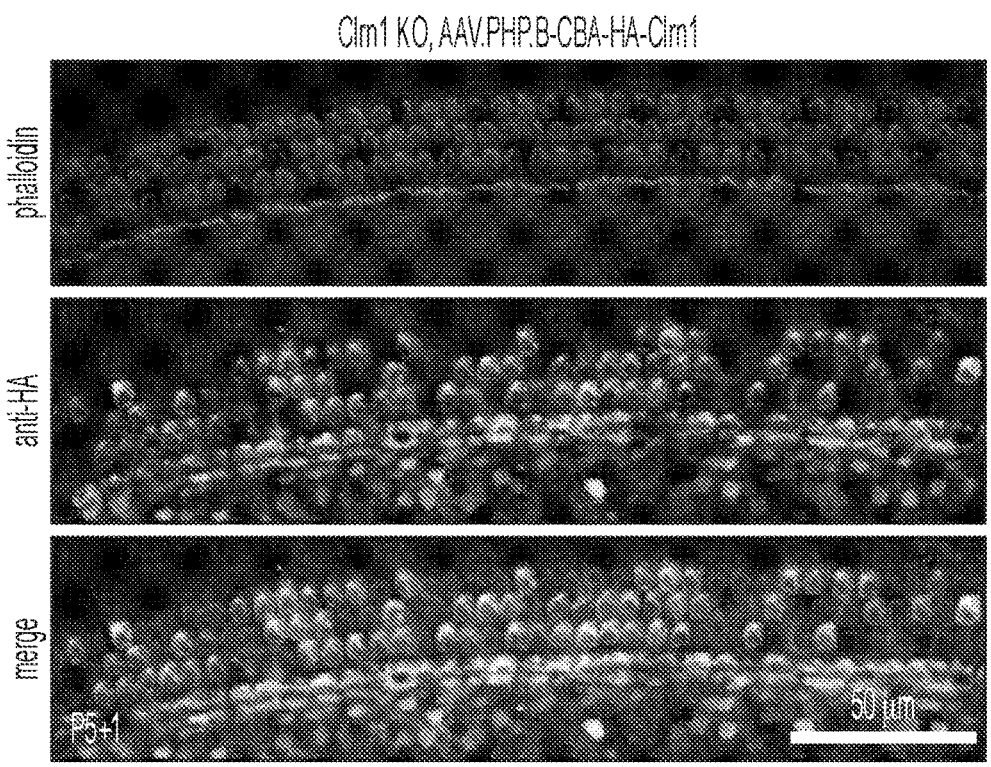
Figure 3C:
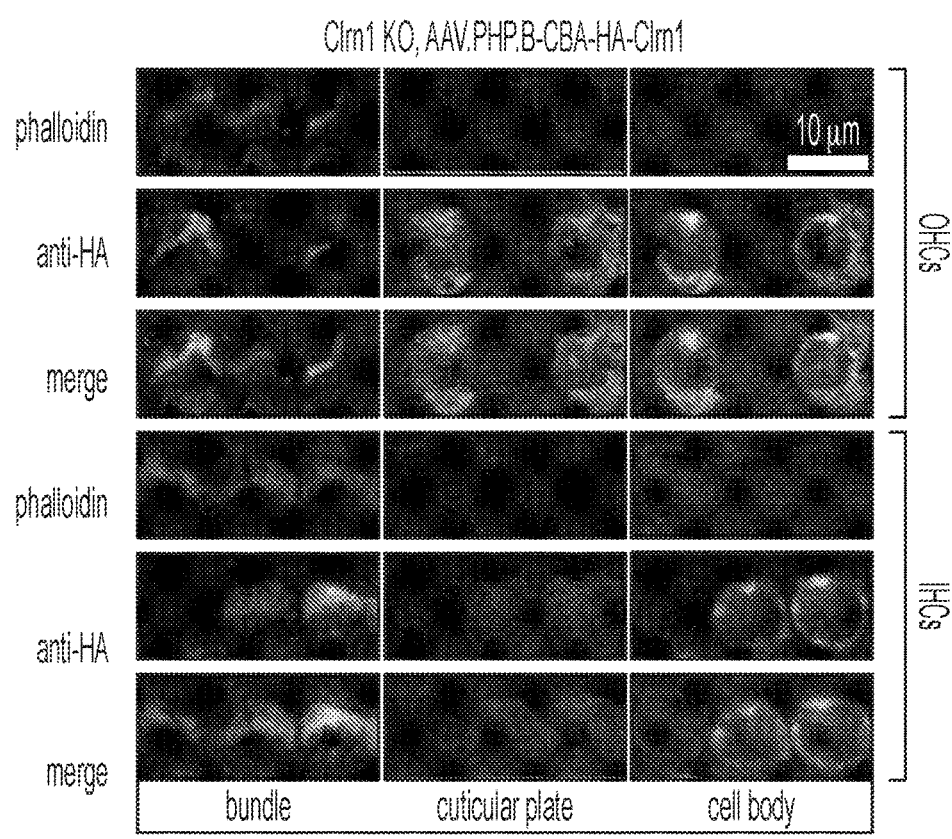
Figure 3D:
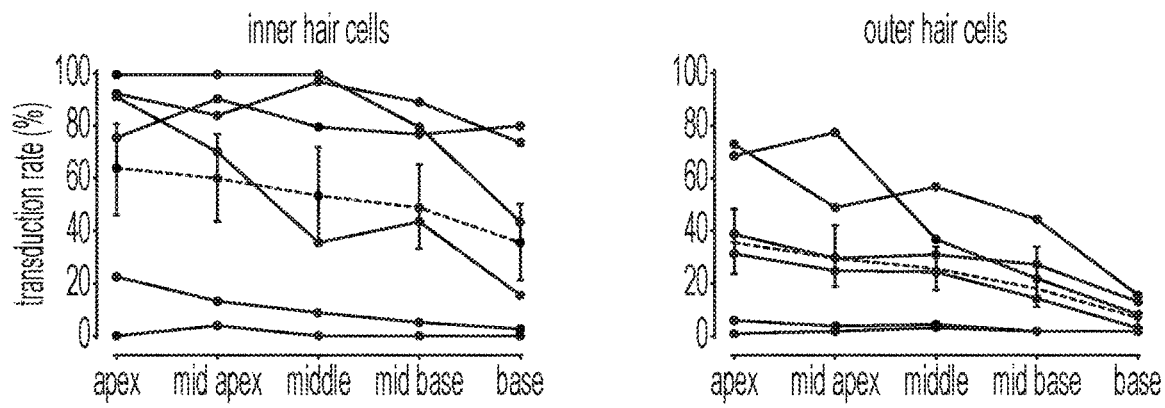
Figure 3E:
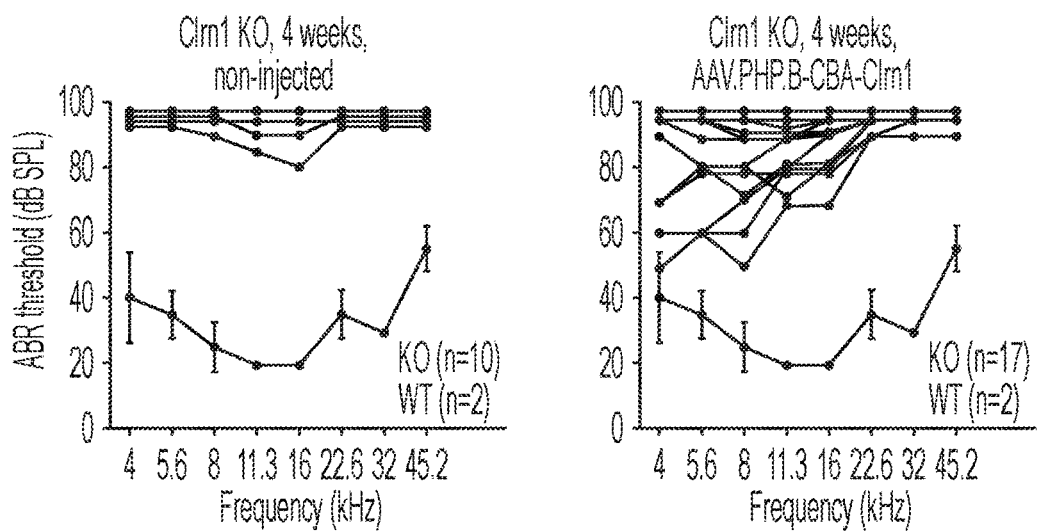

Example 3: AAV9-PHP.B-Mediated Clrn1 Expression in Hair Cells Results in Restoration of Hearing in a Mouse Model of Usher 3A For AAV-mediated Clrn1 expression in HCs, Clrn1 isoform 2 was packaged under the control of the CBA promoter into AAV9-PHP.B (ss genome) with an N-terminal hemagglutinin (HA) tag to allow antibody detection (FIG. 3A). Expression of Clrn1 mRNA by RT-PCR and of clarin-1 protein was observed by immunostaining, after transfection of the plasmid into 293T cells. Next, $7.4\times10^{10}$ VGs of AAV9-PHP.B-CBA-HA-Clrn1 was injected into Clrn1$^{-/-}$ animals at P1. Robust immunostaining with an anti-HA antibody of Clrn1 in the hair bundles of IHCs and OHCs was observed. There was staining also in the kinocilium and cuticular plate region (FIG. 3B and FIG. 3C). Cell bodies showed diffuse immunostaining (FIG. 3C). Importantly, transduction efficiency of vector encoding HA-CLRN1 was similar to that seen with vector encoding GFP, with more efficient transduction in the apex compared to that in the base (FIG. 3D). Finally, to test whether we could rescue hearing in Clrn1$^{-/-}$ mice with gene addition therapy, P1 cochleas was injected through the RWM with $1.8\times10^{11}$ VGs of untagged AAV9-PHP.B-Clrn1 (n=17). Uninjected mice (n=10) were used as controls. Four weeks post-injection, an auditory brainstem response (ABR) recording was performed at different frequencies (FIG. 3E and FIGS. 3G-3J). Measurement of ABRs in uninjected control Clrn1$^{-/-}$ mice (n=10) indicated that they are almost completely deaf by P25, with limited residual hearing in a few animals at 11.3-16 kHz. AAV-injected Clrn1$^{-/-}$ mice showed robust hearing rescue at lower frequencies (4-8 kHz); however, there was little or no rescue at the highest frequencies. The absence of rescue at higher frequencies could be related to the relatively low AAV9-PHP.B-mediated CLRN1 expression in the base (FIG. 3D). The best hearing restoration was a 50-dB reduction in threshold in two animals at 4 and 5.6 kHz. Compared to non-injected animals, hearing restoration was significant at 4, 5.6, 8, and 11 kHz (Wilcoxon test, p<0.05 for all indicated frequencies). Comparison between injected (left) versus non-injected (right) ears reveled significantly lower thresholds in injected ears at 4, 5.6, and 8 kHz (Wilcoxon test, p<0.05 for all indicated animals).

```
The amino acid sequence of clarin-1 isoform 2 with
the HA tag is set forth in SEQ ID NO: 10:
MYPYDVPDYAGGGSGGGSPSQQKKIIFCMAGVLSFLCALGVVTAVGTPLW

VKATILCKTGALLVNASGKELDKFMGEMQYGLFHGEGVRQCGLGARPFRF

SFFPDLVQAIPVSIHINIILFSMILVVLTMVGTAFFMYNAFGKPFETLHG

PLGLYLVSFISGSCGCLVMILFASEVKVHRLSEKIANFKEGTYAYRTQNE

NYTTSFWVVFICFFVHFLNGLLIRLAGFQFPFTKSKETETTNVASDLMY
```

-continued

The nucleic acid sequence encoding clarin-1
isoform 2 with the HA tag is set forth in
SEQ ID NO: 11:
AAGAAGATCATCTTTTGCATGGCTGGCGTACTGAGCTTTCTCTGTGCTCT

TGGAGTGGTGACAGCAGTGGGCACCCCACTGTGGGTTAAAGCCACTATCC

TCTGCAAAACAGGGGCTCTGCTTGTCAACGCGTCAGGGAAGGAGCTGGAC

AAGTTCATGGGCGAGATGCAGTATGGCCTTTTCCACGGAGAAGGCGTAAG

GCAATGTGGGTTAGGAGCAAGGCCTTTCCGGTTCTCATTCTTCCCAGATT

TGGTCCAAGCCATCCCCGTAAGCATCCACATCAATATTATTCTCTTCTCC

ATGATTCTTGTCGTCTTAACCATGGTGGGGACAGCCTTCTTCATGTACAA

TGCTTTTGGCAAGCCCTTTGAAACTCTTCATGGACCACTGGGGCTCTATC

TGGTCAGCTTCATTTCAGGCTCCTGTGGCTGTCTTGTCATGATATTGTTT

GCCTCTGAAGTGAAAGTCCACCGCCTTTCAGAGAAAATTGCAAATTTTAA

AGAAGGGACCTATGCCTACAGAACACAAAACGAAAACTATACCACCTCAT

TCTGGGTTGTTTTCATTTGCTTTTTTGTTCATTTTTTGAATGGGCTCCTG

ATACGACTTGCTGGATTTCAGTTCCCTTTCACAAAATCTAAAGAAACAGA

GACCACTAATGTAGCTTCAGATTTAATGTACTGA

Figure 3F:
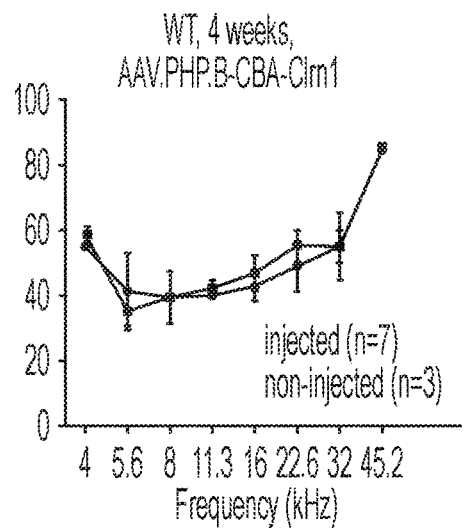
Figure 3G:
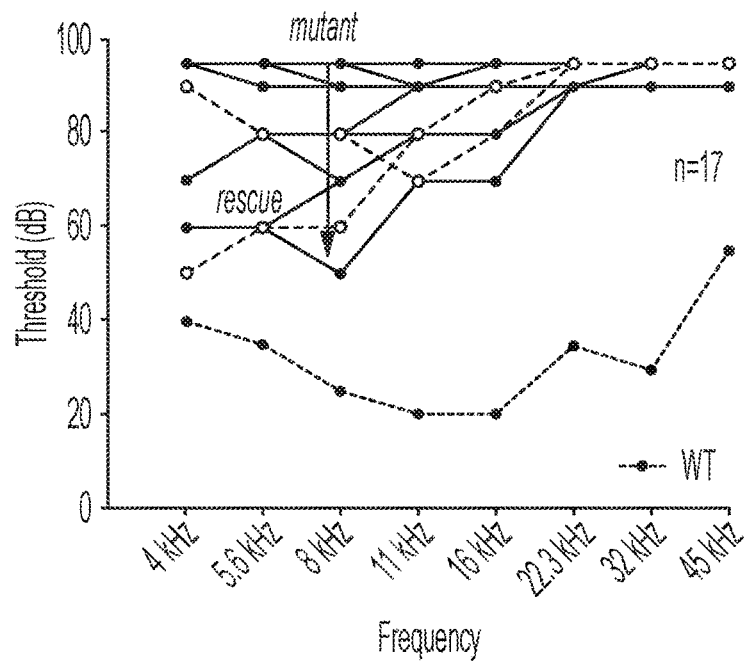
Figure 3H:
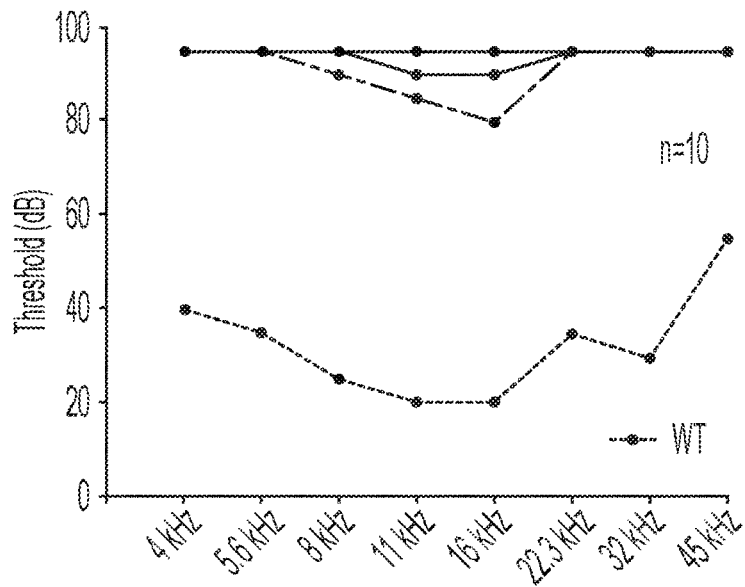
Figure 3I:
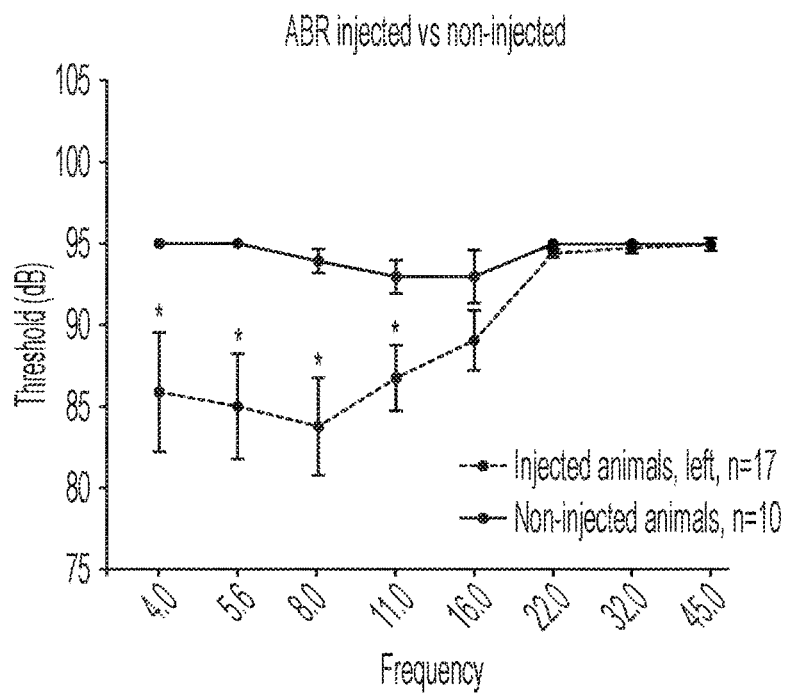
Figure 3J:
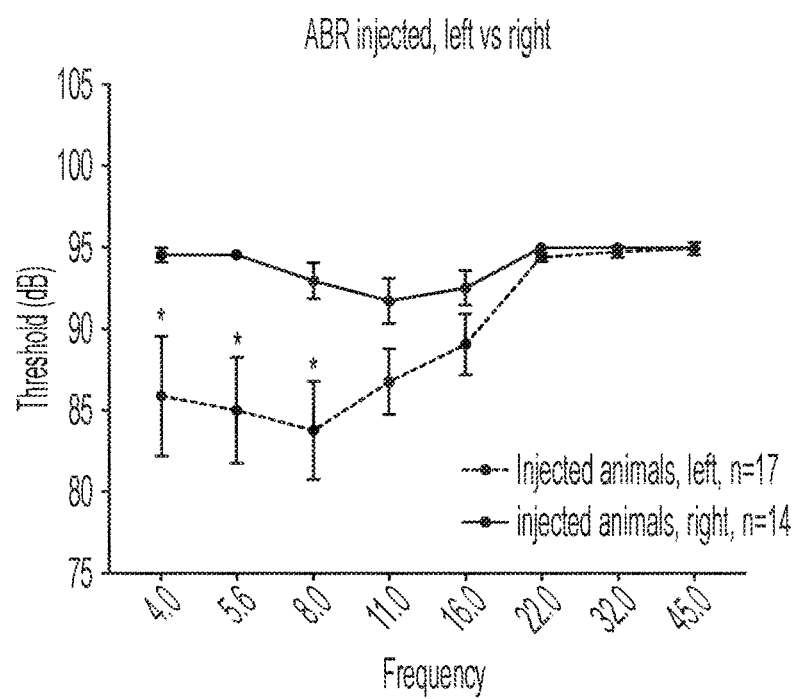

To investigate whether injection of AAV9-PHP.B-Clrn1 would adversely affect the ABR thresholds of normal-hearing mice, a measure of potential vector-related toxicity. P1 wild-type C57BL/6 mice were injected with $4.12 \times 10^{10}$ VGs of AAV9-PHP.B-Clrn1, and 4 weeks later, an ABR assay was performed. No distortion of ABR thresholds in injected mice compared to those in untreated mice, suggesting that the surgery and vector expression was well tolerated (FIG. 3F).

Example 4: AAV9-PHP.B Transduces Retinal Cells in Mice

Figure 4A:
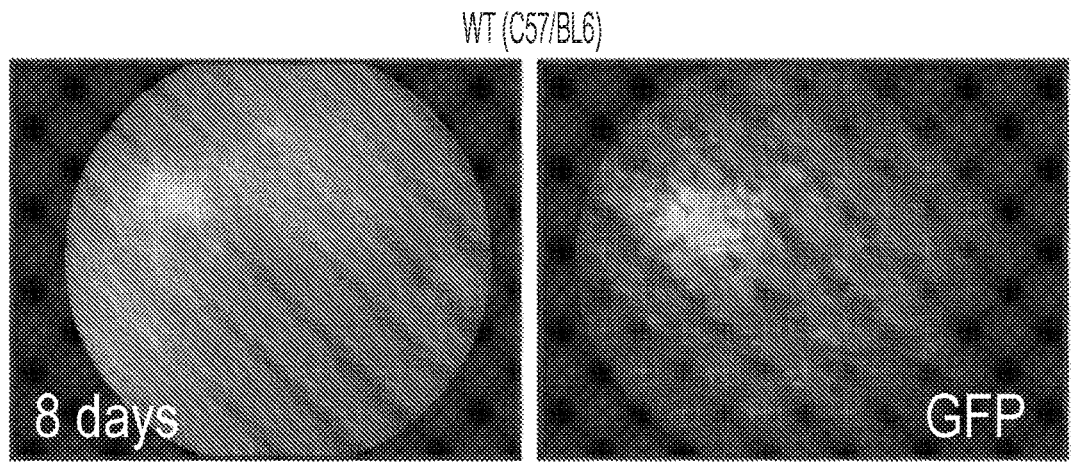
FIG. 4A-4B are pictures showing transduction of mouse retina with AAV9-PHP.B-CBA-GFP. Adult (4.5-month-old) C57/BL6 mice were injected subretinally with $2.1 \times 10^9$ VG (1 mL).
Figure 4B:
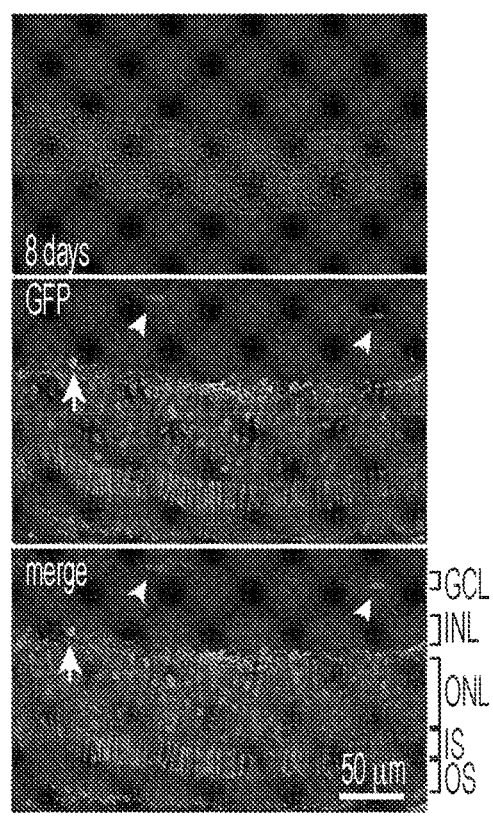

Because Usher 3A patients show late-onset blindness due to retinal degeneration, we tested the ability of AAV9-PHP.B-GFP to transduce retinal cells after subretinal injections (2.1 $35 \times 10^9$ VGs) in adult C57BL/6 mice (n=6 retinas injected). With fundus imaging, widespread retinal transduction was observed 8 days post-injection (FIG. 4A) in 4 of 6 injected eyes (in 2 eyes, the injections failed). Microscopy revealed robust (~70%-80%) photoreceptor transduction at the injection site in AAV9-PHP.B-GFP-injected eyes (FIG. 4B), along with some GFP-positive cells in the inner nuclear layer (INL) and ganglion cell layer (GCL). These results suggest that the AAV-PHP.B capsid can be used to target both inner ear HCs and retinal photoreceptors.

Example 5: AAV9-PHP.B Transduces Cells in NHP Inner Ear after RWM Injection

As a step toward clinical translation to humans, the efficacy of transducing IHCs and OHCs by AAV9-PHP.B in NHPs was evaluated. A male juvenile cynomolgus monkey (animal #1002) was injected in one ear via the RWM with a dose of $3 \times 10^{11}$ VGs of AAV9-PHP.B-GFP in a volume of 10 mL, using a trans-mastoid approach similar to that reported by Dai et al. The contralateral (left) ear was used as a control. Seven weeks later, the animal was sacrificed, the temporal bone was extracted and decalcified over 3 months, and the cochlea was sectioned for histological analysis. H&E examination of the injected and noninjected cochleas indicated little change associated with the surgery and vector injection. We observed small bone fragments in the middle ear, with minimal inflammation and slight fibrous tissue, which is consistent with temporal bone fragments generated during the surgical procedure. Examination of sections of the cochlea in the injected ear revealed mild hemorrhage, which is expected with this surgical procedure. We detected some inflammatory cells in the non-injected cochlea. The HCs, stria vascularis, and spiral ganglion neurons had normal morphology.

Figure 5A:
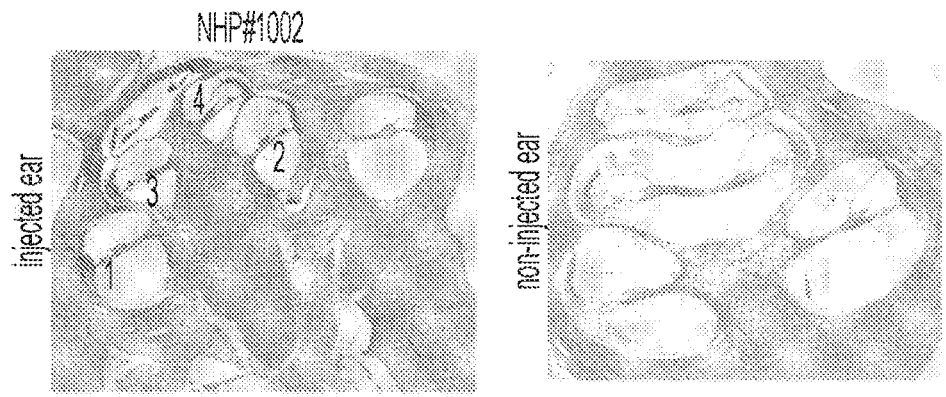
FIG. 5A-5F are pictures showing transduction profile of AAV9-PHP.B-CBA-GFP in the Cynomolgus Monkey (Animal #1002). Vector (10 mL; $3 \times 10^{11}$ VGs) was injected through the RWM of a 2.6-year-old, 4-kg Macaca fascicularis monkey.
Figure 5B:
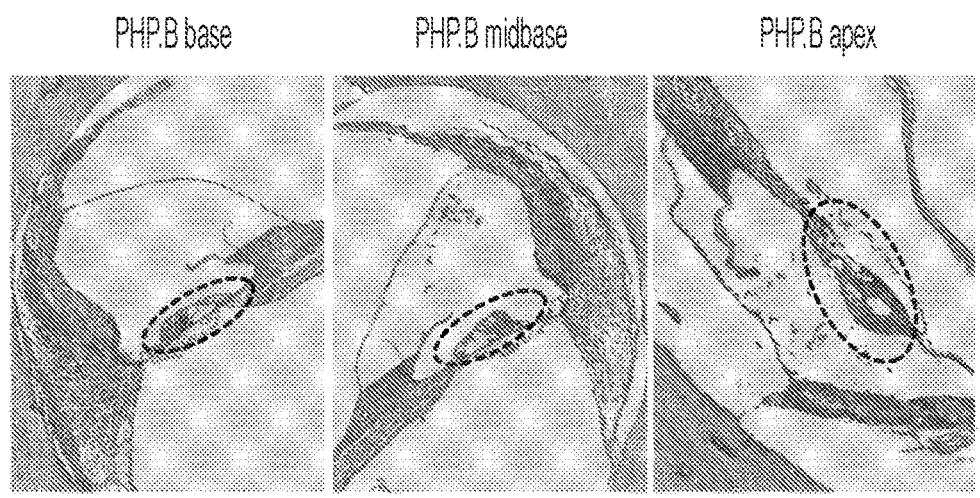
Figure 5C:
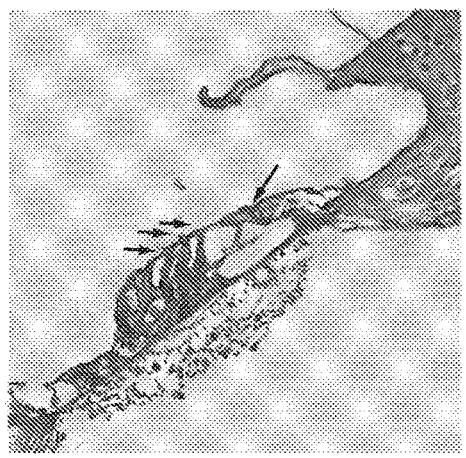
Figure 5C:
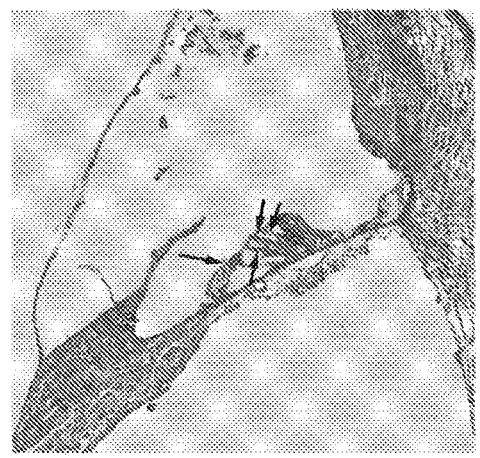
Figure 5D:
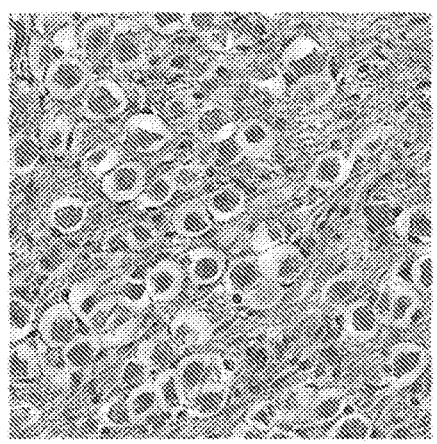
Figure 5D:
Figure 5E:
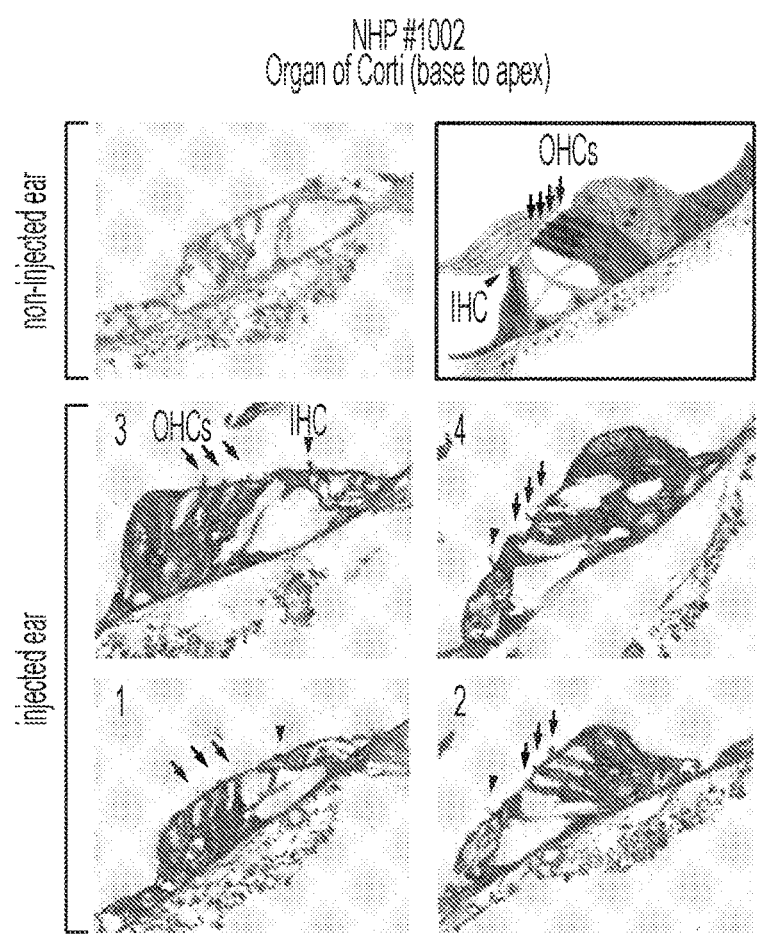
Figure 5F:
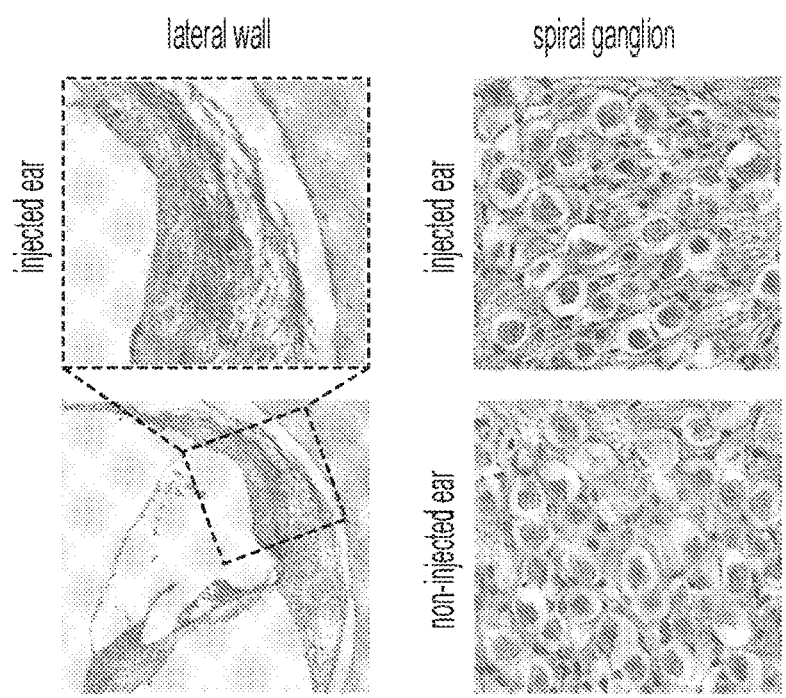

An anti-GFP antibodies to assess GFP expression in both uninjected and injected ears. While no specific staining was observed in the uninjected ear (FIGS. 5A, right, and 5E, top left), we observed robust GFP immunoreactivity throughout the cochlea in the injected ear (FIG. 5A, left). GFP appeared in the organ of *Corti*, spiral ligament, spiral limbus, and stria vascularis, from the base to the apex. Higher magnification revealed GFP expression by HCs in the organ of *Corti* (FIGS. 5B and 5C). Quantitation of GFP immunoreactive HCs in cochlear turns in serial sections revealed 92% transduction of IHCs and 92% of OHCs. Widespread transduction in the lateral wall was observed as well. Additionally, GFP expression was detected with lower intensity in the spiral ganglion neurons (FIG. 5D-5F).

Example 6: AAV1 Expressing GJB2 Transduces Cells in NHP Inner Ear after RWM Injection GJB2 was recognized as the causative gene for DFNB1 in 1997. Over 100 mutations have since been described in patients, but nearly 60% of patients have a single base deletion (35delG) leading to a frameshift and stop. The phenotype was originally described as profound deafness, but it is now recognized that the hearing loss ranges from mild to profound. Profound deafness is probably irreversible even at birth, but milder cases may be treatable with gene therapy. GJB2 is expressed in a network of fibrocytes in the cochlea, but also in several other cell types in the sensory epithelium. In mice, constitutive deletion of Gjb2 is embryonic lethal, so conditional knockouts have been developed to model DFNB1 deafness. Rescue of hearing by AAVS expression of the Gjb2 coding sequence under a CMV promoter was modest at best, with better vectors clearly needed.

Figure 6:
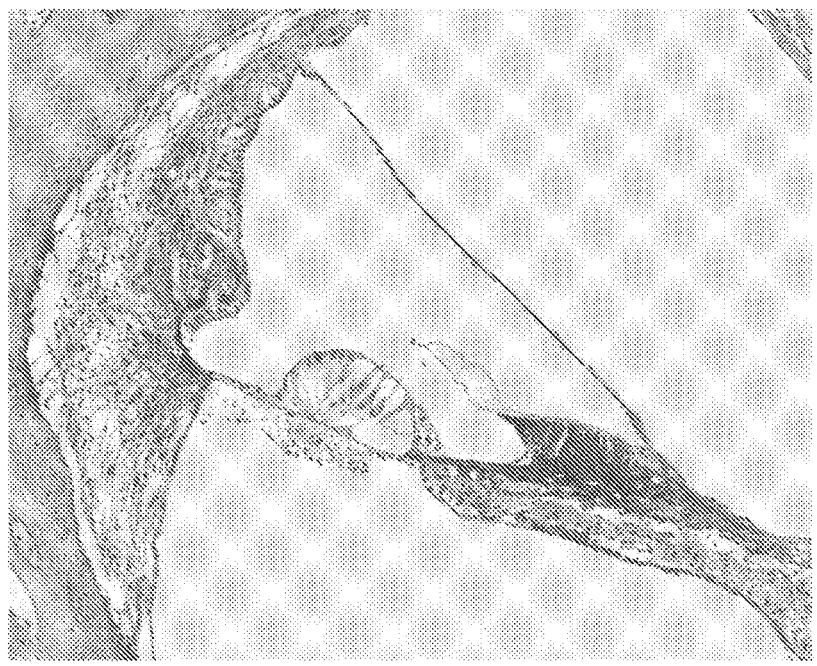
FIG. 6 is a picture showing transduction efficiency of AAV1 encoding GJB2 in fibrocytes of the inner ear.

We have explored several new AAV vector in both mouse and primate, and have achieved substantial rescue of hearing in a mouse lacking the hair-cell gene Lhfp15, using the novel exo-AAV1 (Gyorgy et al., 2017). We have also shown that AAV transduces most cells in the monkey inner ear (FIG. 6).

These and ongoing studies will produce AAV serotypes that are highly efficient at targeting the relevant cell types.

Materials and Methods

AAV Vector Constructs

An AAV transgene plasmid, flanked by AAV2 inverted terminal repeats (ITRs), encoding GFP under the hybrid cytomegalovirus (CMV) immediate-early/CBA promoter, and with a woodchuck hepatitis virus posttranscriptional regulatory element (WPRE) was used. This vector (AAV-CBA-GFP-W) encodes a ss genome. The helper plasmid pAdDF623 was obtained from the Massachusetts General Hospital Vector Core. The pGG-PHP.B plasmid encoding the rep genes of AAV2 and the AAV9 variant, AAV9-PHP.B, was provided by Dr. Miguel Sena Esteves (University of Massachusetts Medical School), who synthesized the capsid sequence based on the published sequence. We constructed an AAV ITR-containing plasmid encoding murine clarin-1. The open reading frame of isoform 2 of Clrn2 was synthesized by GenScript (Piscataway, NJ, USA) and cloned into a ss AAV-expression (AAV-CBA-W) plasmid into the multiple cloning site to generate AAV-CBA-Clrn1-W. We also had HA-tagged Clrn1 constructs synthesized (GenScript) and cloned them similarly into AAV-CBA-W.

To test whether the constructed plasmids expressed CLRN1, HEK293T cells were transiently transfected (calcium phosphate method) with each of the following plasmids in separate wells: AAV-CBA-Clrn1 (no tag), AAV-CBA-HA-Clrn1, and AAV-CBAClrn1-HA. AAV-HA-Lhfp15 was a previously characterized plasmid that we used as a negative control for Clrn1 mRNA detection and a positive control for HA staining. Forty-eight hours post-transfection, a subset of wells was harvested for RNA harvest, while another set was harvested for immunofluorescence staining of the HA tag.

Vector Production and Purification

For each production, we plated ten 15-cm tissue culture dishes with $1.5 \times 10^7$ 293T cells per dish. The next day, cells were transfected using the calcium phosphate method, with the adenovirus helper plasmid (pAdDF6, 26 mg), rep/cap plasmid (pGG-PHP.B for AAV9-PHP.B, 12 mg), and ITR-flanked transgene cassette plasmid (10 mg) to induce production of AAV. The day after transfection, medium was changed to DMEM containing 2% fetal bovine serum (FBS). AAV was purified from the cell lysate using iodixanol density-gradient ultracentrifugation. Buffer exchange to PBS was conducted using Zeba spin columns (7K MWCO; Thermo Fisher Scientific) and further concentration was performed using Amicon Ultra 100-kDa MWCO ultrafiltration centrifugal devices (Millipore). Vectors were stored at −80° C. until use. AAV genomic copies in AAV preparations was quantified using TaqMan qPCR with bovine growth hormone (BGH) poly(A) sequence-specific primers and probe.24 During the course of this study, several independent preparations of AAV9-PHP.B vector were made, with each having slightly different titers. Maximum injectable volume was used in each model (1.2 mL for neonatal mice and 10 mL for macaques), which resulted in differences in the dose between some experiments. All doses used are indicated in the figure legends and/or Results section.

Mouse Housing and Breeding

All experiments were performed in compliance with ethical regulations approved by the Animal Care Committee of Harvard Medical School (HMS). Wild-type pregnant C57BL/6 females were ordered from Charles River Laboratories, and pups were used for AAVCBA-GFP transduction experiments. Clrn1 knockout (KO) animals, in which the first coding exon was deleted, 21 were a generous gift from Dr. Kumar Alagramam (Case Western Reserve University).

Genotyping was done as previously described.22 They were housed and bred at the HMS animal facility.

Mouse RWM Injection in Neonatal Mice

P0-P1 CD1 and C57BL/6 pups were anesthetized by hypothermia and then kept on an ice pack during the procedure. As previously described, 5 a small incision was made underneath the external ear. The incision was enlarged, and soft tissues were pushed apart using an eyelid retractor to expose the bulla. Then the round window niche was localized visually. Covering connective tissue was removed to expose the round window. For GFP expression experiments, we injected 1.0-1.2 mL of AAV9-PHP.B-CBA-GFP vector solution at rate of 60 nL/min. For rescue experiments, 1.0-1.2 mL of the AAV9-PHP.B-CBA-Clrn1 vector was injected into the ear, which encodes clarin-1 without the HA tag. For immunostaining to detect clarin-1 encoded by the AAV, the vector encoding an N-terminal HA-tagged clarin-1 was used. Surgical incisions was closed with 2-3 sutures using a 7-0 Vycril surgical suture. After injection, we waited 5 days before sacrifice to assess vector transduction.

Adult Mouse Injection 4-week-old mice were anesthetized with ketamine (100 mg/kg) and xylazine (20 mg/kg) through an intraperitoneal injection. Both eyes were protected by an application of eye gel (GenTeal lubricant eye gel). The fur behind the left ear was shaved with a sterile razor, and the surgical area was cleansed two times with antiseptic solution, isolated with sterile drapes, and swabbed along the proposed incision with 10% povidone-iodine. a surgical procedure similar to that described by Suzuki et al.18 A small (10- to 15-mm) postauricular skin incision was made. After exposing the facial nerve and the sternocleidomastoid muscle by blunt dissection, the tissue covering the temporal was separated and retracted using the magnetic retractor set. A small hole was made with a microprobe in the exposed bony wall of the posterior canal. After 2-3 min for leakage of perilymph to stop, the tip of a MicroFil 35 G needle was inserted into the hole. The aperture between the MicroFil needle and the hole was sealed with tissue fragments and cyanoacrylate glue (3 M Vetbond Tissue Adhesive) and visually assessed for lack of fluid leakage. 1 mL viral suspension at 155 nL/min was injected using the Nanoliter 2000 Injector (World Precision Instruments). After the injection was completed, the plastic needle remained in the canal for 5 min and then was cut off proximally to the canal. The hole was filled in with tissue and sealed with glue. The wound was closed with 5-0 Vicryl-coated sutures and swabbed with 10% povidone-iodine. The mouse was placed on a heating pad until full recovery. Animals Freceived an intraperitoneal injection of meloxicam (0.01 mL/g body weight) after surgery and once more within the first 24 hr. Injected mice were checked daily for 5 days following surgery.

Mouse Cochlear Immunostaining and Imaging.

For FM1-43 loading, organ of *Corti* epithelium was acutely dissected from P5 mice in L-15 cell culture medium and cultured for an additional day in DMEM supplemented with 5% FBS and ampicillin (10 mg/L). Following tectorial membrane removal and medium aspiration, FM1-43 solution (2 mM in L-15) was applied to the tissue for 30-60 s and then quickly aspirated. The explant was then rinsed once with L-15, and the excessive dye was quenched by a 0.2 mM solution of 4-sulphonate calixarene, sodium salt (SCAS, Biotium), in L-15. The organ of *Corti* was then observed on an upright Olympus FV1000 confocal microscope, equipped with a 60 1.1-NA water-dipping objective lens.

For immunostaining, cochleas were fixed with 4% formaldehyde in PBS for 20 min. Fixed cochleas were washed 3 times with PBS to remove fixative and were blocked with 5% normal goat serum and permeabilized with 0.3% Triton X-100 in PBS for 1 hr at 22 C. Primary antibodies were diluted in 5% normal goat serum (NGS)/0.1% Triton X-100/PBS and incubated overnight at 4 C. To label HCs, rabbit polyclonal anti-myosin VIIa antibody (*Proteus* Biosciences; 1:500 dilution) was used with a goat anti-rabbit immunoglobulin G (IgG) secondary antibody conjugated to Alexa Fluor 647 in a 1:1,000 dilution for 1 hr (Life Technologies). To stain the hair bundle actin, phalloidin conjugated to Alexa Fluor 544 (Life Technologies) (1:50) was used. To detect the HA tag, a rabbit anti-HA antibody (C29F4; Cell Signaling Technology) was used. GFP was detected via its intrinsic fluorescence (i.e., no immunostaining for GFP). Tissues were mounted on a Colorfrost glass slide (Thermo Fisher Scientific) using Prolong Gold Antifade mounting medium (Thermo Fisher Scientific). Imaging for GFP fluorescence was performed with a Zeiss LSM 710 confocal microscope using a PlanApoN 60/1.42-NA oil-immersion objective. For imaging to detect HA staining, an Olympus FluoView 1000 confocal microscope with a 60/1.42-NA oil-immersion objective was used.

Quantification of EGFP Expression in Neonatal Murine HCs and Transduction Efficiency Analysis Whole-mount cochleas, immunostained as described earlier, were imaged on a Zeiss LSM 710 for quantification in five different region (apex, mid-apex, middle, mid-base, and base), each ~250 mm long along the axis of the organ of Corti and ~800 mm apart. The laser intensity was chosen based on the specimen with the strongest EGFP signal to prevent fluorescence saturation, and the same settings were then used for each image of a set. The efficiency of IHC and OHC cell transduction was evaluated by two blinded investigators using the ImageJ program (NIH Image). HCs were identified with immunolabeling for MYO7A. Control samples without AAV were used to exclude autofluorescence. Segments with dissection-related damage were removed from the analysis.

Mouse ABR

The ABR assay was performed using a Tucker Davis Technologies System III workstation. Mice were anesthetized by intraperitoneal injection of a ketamine (100 mg/kg)/xylazine (10 mg/kg) cocktail. Anesthetized mice were then placed on a heating pad, and electrodes were placed subcutaneously in the vertex, underneath the left or right ear, and on the back near the tail. Tone stimuli of 4, 5.6, 8, 11.2, 16, 22, 32, and 45.3 kHz were calibrated with a precision microphone system (PS9200 Kit; ACO Pacific), using the TDT SigCal software package. The recorded signals were band-pass filtered (300 Hz to 3 kHz) and amplified 100,000 times. The number of acquisition trials was set to 500 averages. Maximum stimulus intensity was set to 95 dB peak SPL with attenuation decreasing from 85 dB to 0 dB SPL at 5-dB intervals. Band-pass filters (500-3,000 Hz) were applied to the traces before analysis.

Mouse Retina

Animals were handled in accordance with the statement of the "Animals in Research Committee" of the Association for Research in Vision and Ophthalmology (Rockville, MD, USA), and protocols were approved by the local institutional committee (Service vétérinaire du canton de Vaud, Lausanne, Switzerland). Adult C57BL/6 mice were anesthetized with a reversible anesthetic regimen composed of ketamine and medetomidine (ketamine, 30-60 mg/kg, Parker Davis; medetomidine, 0.5-1 mg/kg, Graeub), and the anesthesia was reversed with the injection of atipamezole (0.5-1 mg/kg, Graeub). For subretinal injections, a transcleral approach was used, and the procedure was visualized in the posterior chamber with a microscope and a coverslip covering the cornea surrounded with Viscotears (Novartis, Basel, Switzerland). AAV9-PHP.B-CBA-GFP vector (1 mL) was injected into the sub-retinal space of adult mice through a Hamilton syringe with a 34 G needle (BGB Analytik).

Scanning Electron Microscopy

Organ of Corti explants were dissected at P1 and P5 in L-15 medium and fixed with 2.5% glutaraldehyde in 0.1 M cacodylate buffer (pH 7.2) supplemented with 2 mM $CaCl_2$) for 1-2 hr at room temperature. For older (P30) animals, after intracardial perfusion with 4% paraformaldehyde and 1% glutaraldehyde, temporal bones were decalcificated overnight in 10% EDTA (pH 7.2-7.4) for 3-4 days at 4 C. After unpeeling cochlear bone and removing the stria vascularis and tectorial membrane, the cochlear coils were isolated; divided into apical, middle, and basal turns; and postfixed with 2.5% glutaraldehyde in 0.1 M cacodylate buffer (pH 7.2) supplemented with 2 mM $CaCl_2$) for 1-2 hr at room temperature. They were rinsed three times in 0.1 M cacodylate buffer (pH 7.2), washed in distilled water, dehydrated in an ascending series of ethanol concentrations, and criticalpoint dried from liquid C02. Samples were then mounted on aluminum stubs with carbon conductive tabs and sputter-coated with 5 nm platinum, and then imaged in a field-emission scanning electron microscope (Hitachi S-4700).

Rat Cochlea

Sprague-Dawley rats (Charles River Laboratories) were injected at P1 through the RWM with 1.2 mL vector (ss AAV9-PHP.B-CBA-GFP) at an injection speed of 60 nL/min. The animals were allowed to recover from the injections; after 3 days, they were euthanized, and their cochleas were dissected. To assess vector transduction, organ of Corti explants were isolated, mounted on glass-bottom dishes, and cultured as previously described.5 Transduction was assessed on the day of the dissections (P4) or after 4 days in culture (P4+4) by visualizing the GFP fluorescence using confocal imaging.

NHP Cochlea

NHP studies were performed at Charles River Laboratories (Montreal, ON, Canada) according to animal use guidelines and approved procedures. The first cynomolgus monkey (*Macaca fascicularis*) (animal #1002) was a male, age 2.6 years, weighing 4 kg. The second animal (animal #3501) was a female, age 3.1 years, weighing 3.2 kg. The animals were anesthetized by intramuscular injection of a cocktail (ketamine, 10 mg/kg; xylazine, 0.6 mg/kg; and glycopyrrolate, 0.01 mg/kg) following overnight food deprivation, intubated, and maintained with oxygen and isoflurane during surgery. During the procedure, the following were administered to improve recovery: warmed lactated Ringer's solution intravenously (10 ml/kg/hr), cefazolin (20 mg/kg every 20-90 min), and topical antibiotics to the surgical site.

The RWM was exposed using a trans-mastoid approach. Beginning with a low microscopic magnification, the temporal muscles were retracted exposing the supramastoid crest and the external cartilaginous portion of the ear canal. En route to the middle ear and with increasing magnification, mastoid air cells were burred very closely to the cartilaginous portion of the ear canal, and the bony portion thinned until the fossa incudis was reached, exposing the incus. A 1- to 2-mm facial recess was then performed with awareness of the horizontal semicircular canal, the facial nerve, and the tympanic membrane. The chorda tympani was retracted and/or resected, since it was not possible to preserve it without damaging the critical surrounding structures while allowing necessary exposure of the round window niche. In this species, the RWM is 0.6 mm in diameter.

Under micromanipulator control, a 29 G injection needle was lowered through the RWM. For the first animal, vector (10 mL) was injected with a pump at 0.5 mL/min for 20 min, delivering $3 \times 10^{11}$ VGs of AAV9-PHP.B-GFP into the right ear. The control left ear was uninjected. The second animal was injected in both ears with 10 mL AAV9-PHP.B-GFP (1 1011 VGs per cochlea). Carprofen (4 mg/kg), Rimadyl (4 mg/kg), buprenorphine (sustained release [SR]: 0.2 mg/kg), and dexamethasone (0.75 mg/kg) were administered at appropriate intervals during the surgical recovery period. Animals were group housed during the observation period and monitored for reaction to treatment and body weight change. Seven (animal #1002) or 8 (animal #3501) weeks post-surgery, the animal was euthanized, and temporal bones were excised. Tissue was fixed in neutral buffered 10% formalin for 48 hr and transferred to an EDTA solution for decalcification. Tissue was transferred to fresh solution and periodically scanned (Faxitron X-ray) until fully decalcified (~12 weeks) and then was embedded in paraffin, sectioned (5-mm sections at 200-mm intervals to reach the midmodiolar cochlea), and mounted on glass slides. Slides were stained with H&E for histopathology evaluation or left unstained for immunohistochemistry. Sections of cochlea were deparaffinized, using xylene followed by 100% and 95% ethanol washes, and then were rehydrated in water. Sections were permeabilized with 0.5% Triton X-100 in PBS for 30 min. Sections were blocked for endogenous peroxidase using 3% hydrogen peroxide for 10 min, washed, and then blocked using 1×Tris-buffered saline-Tween 20 (TBST)/5% normal goat serum for 1 hr at room temperature. Next, sections were incubated overnight at 4 C in primary antibody (anti-GFP antibody: GFP (D5.1) XP Rabbit mAb [monoclonal antibody], #2956, Cell Signaling Technology) at a 1:200 dilution in SignalStain antibody diluent (Cell Signaling Technology), and then they were washed and incubated in SignalStain Boost IHC Detection Reagent (horseradish peroxidase, rabbit #8114, Cell Signaling Technology) for 30 min at room temperature. After three washes, SignalStain diaminobenzidine (DAB) substrate was added to slides for 1-10 min until proper staining intensity had developed (in comparison to a negative control section such as secondary antibody only or uninjected cochlea). Slides were immersed in water and then counterstained with hematoxylin. Sections were washed in water, dehydrated with ethanol and xylene, and mounted using SignalStain mounting medium. Slides were viewed and digitized on an Olympus VS120 Virtual Slide Microscope.

Statistics

To compare two non-related sample groups, we used a t test for two independent samples or a Mann-Whitney U test. For normality testing, we used the Shapiro-Wilk test.

For statistical testing, GraphPad Prism software was used. p values<0.05 were considered statistically significant.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A recombinant adeno-associated virus (rAAV) comprising:
   (i) an AAV PHP.B capsid protein; and
   (ii) an isolated nucleic acid comprising:
      (a) a first region comprising a first AAV inverted terminal repeat (ITR); and
      (b) a second region comprising a transgene encoding Gap Junction beta 2 (GJB2).

2. The rAAV of claim 1, wherein the rAAV is a single-stranded AAV (ssAAV) or a self-complementary AAV (scAAV).

3. The rAAV of claim 1, wherein the rAAV is capable of delivering the transgene to a mammal.

4. The rAAV of claim 1, wherein the rAAV is formulated for delivery to the ear.

5. A pharmaceutical composition comprising the rAAV of claim 1 and a pharmaceutically acceptable carrier.

6. A method for delivering GJB2 protein into a cell comprising: introducing the rAAV of claim 1 into the cell.

7. A method for expressing GJB2 protein in a subject in need thereof comprising administering to the subject an effective amount of the rAAV of claim 1, wherein the subject has or suspected of having hearing loss.

8. The method of claim 7, wherein the subject is a human.

9. The method of claim 7, wherein the subject is diagnosed with Non-syndromic Hearing Loss and Deafness (DFNB1).

10. The method of claim 7, wherein the administration is via injection.

11. The method of claim 10, wherein the injection is through round window membrane of the inner ear.

12. A recombinant adeno-associated virus (rAAV) comprising:
(i) an AAV9.PHP.B capsid protein; and
(ii) an isolated nucleic acid comprising:
(a) a first region comprising a first AAV inverted terminal repeat (ITR); and
(b) a second region comprising a transgene encoding clarin-1.

13. The rAAV of claim 1, wherein GJB2 comprises an amino acid sequence 90% identical to the amino acid sequence of SEQ ID NOs: 3 or 5.

14. The rAAV of claim 1, wherein the transgene encoding GJB2 comprises a nucleic acid sequence of SEQ ID NO: 4 or 6.

15. The rAAV of claim 1, wherein the transgene further comprises a promoter.

16. The rAAV of claim 1, wherein the isolated nucleic acid further comprises a third region comprising a second AAV ITR.

17. A method of treating genetic hearing loss in a subject, the method comprising administering to the subject an effective amount of an rAAV comprising:
(i) an AAV9.PHP.B capsid protein; and
(ii) an isolated nucleic acid comprising:
(a) a first region comprising a first AAV inverted terminal repeat (ITR); and
(b) a second region comprising a transgene.

18. The rAAV of claim 4, wherein the rAAV is formulated for delivery to the cochlea or a fibrocyte lining of the inner ear.

19. A method of treating Non-syndromic Hearing Loss and Deafness (DFNB1) in a subject, the method comprising administering to the subject an effective amount of the rAAV of claim 1.

* * * * *